US006858425B1

(12) United States Patent
Heus

(10) Patent No.: US 6,858,425 B1
(45) Date of Patent: Feb. 22, 2005

(54) HUMAN ACID ALPHA GLUCOSIDASE GENE AND BOVINE ALPHA-S1 CASEIN GENE SEQUENCES

(75) Inventor: Joris Jan Heus, Amsterdam (NL)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/454,466

(22) Filed: Dec. 3, 1999

Related U.S. Application Data

(60) Provisional application No. 60/122,550, filed on Mar. 2, 1999, and provisional application No. 60/110,850, filed on Dec. 4, 1998.

(51) Int. Cl.$^7$ .......................... C07H 21/04; C12N 9/00; C12N 15/00; C12N 9/36

(52) U.S. Cl. ............................ 435/320.1; 435/4; 435/6; 435/69.1; 435/183; 435/195; 435/206; 435/252.1; 536/23.2; 536/24.1 T

(58) Field of Search ............................... 435/4, 6, 69.1, 435/183, 195, 206, 252.1, 320.1; 536/23.2, 24.1 T, 23.1; 702/520

(56) References Cited

U.S. PATENT DOCUMENTS 5,565,334 A * 10/1996 Abe et al.

FOREIGN PATENT DOCUMENTS

WO WO94/16057 A * 7/1994

OTHER PUBLICATIONS

Tzall et al. Identification of the promoter region and gene expression for human acid alpha glucosidase. Biochem. Biophys. Res. Comm., vol. 176(3):1509–1515, 1991.*

GenBank Accession No. X55079, Hoefsloot et al. dated Nov. 14, 1998.*

GenBank Accession No. X59856, Koczan et al. dated Oct. 24, 1991.*

GenBank Accession No. Q66990, Abe et al. dated Jul. 21, 1994.*

* cited by examiner

*Primary Examiner*—Manjunath N. Rao
(74) *Attorney, Agent, or Firm*—Townsend and Townsend and Crew LLP

(57) ABSTRACT

The invention provides polynucleotide sequences from the human acid alpha glucosidase gene and the bovine alpha S1 casein gene. These sequences are useful for designing transgenes for expression of human acid alpha glucosidase in the milk of transgenic animals. The sequences are also useful for design of primers and probes, and for computerized methods of sequence comparison.

5 Claims, 9 Drawing Sheets

SEQUENCE LISTING

<160> NUMBER OF SEQ ID NOS: 5

<210> SEQ ID NO 1
<211> LENGTH: 26167
<212> TYPE: DNA
<213> ORGANISM: Homo sapiens

<400> SEQUENCE: 1

```
gagacggagt ctcgctctgt cgcccaggct ggagtgcagt ggcgcggtct cggctcgctg     60

caagctggaa agggggcttt taatgcccct atgcccctac ccaggaacaa cacctctgtg    120

ttttggtgtg gctccttttg tatttttctg cacatacatt ttattaggca agttaaggtt    180

atactgtgtg ttttttgtat ctcacatgta aaaatgtgct cctcttaatg taagcatttt    240

ctcattttat gaaaaaattc cccctgtgtc agtttaatgt tttctcaatt gtcagtttta    300

tgggttatca caatgttttg attattcctt tctggaataa ctgtgagtta tggagcacac    360

ttaaggactt tccaaatgtt ggctgtttct aacttggcgc tgagcgcctt tggccgcctt    420

tccgatgatg ccctcgggac gcgttggcag gaggaatccc tgggcgcaag gcgcggctgg    480

gccagcccct tacaaagccc tacgagctgc ggggacccag gccggggcag cgggggccac    540

gccccatctc cgaccccacg gggaccgggc cgggactgcg ccagcggggg cctcgccccg    600

tctctgaccc cagaggaacc ggcagcgggc agcacgcgtg ggcctctccc cgcgggacgc    660

cggacgcgca gccagacgcg ctccccaggc cccctccgag agcgaggacg cgcccaggcc    720

cgctctgccg gagccgccac tggggggcgt agcgcggacg cgcacccttg cctcgggcgc    780

ctgcgcggga ggccgcgtca cgtgacccac cgcggccccg ccccgcgacg agctcccgcc    840

ggtcacgtga cccgcctctg cgcgcccccg ggcacgaccc cggagtctcc gcgggcggcc    900

agggcgcgcg tgcgcggagg tgagccgggc cggggctgcg gggcttccct gagcgcgggc    960

cgggtcggtg gggcggtcgg ctgcccgcgc ggcctctcag ttgggaaagc tgaggttgtc   1020

gccggggccg cgggtggagg tcggggatga ggcagcaggt aggacagtga cctcggtgac   1080

gcgaaggacc ccggccacct ctaggttctc ctcgtccgcc cgttgttcag cgagggaggc   1140

tctgcgcgtg ccgcagctga cggggaaact gaggcacgga gcgggtgaga cacctgacgt   1200

ctgccccgcg ctgccggcgg taacatccca gaagcgggtt tgaacgtgcc tagccgtgcc   1260

cccagcctct tcccctgagc ggagcttgag ccccagacct ctagtcctcc cggtctttat   1320

ctgagttcag cttagagatg aacggggagc cgccctcctg tgctgggctt ggggctggag   1380

gctgcatctt cccgtttcta gggtttcctt tccccttttg atcgacgcag tgctcagtcc   1440

tggccgggac ccgagccacc tctcctgctc ctgcaggacg cacatggctg ggtctgaatc   1500

cctggggtga ggagcaccgt ggcctgagag ggggcccctg ggccagctct gaaatctgaa   1560

tgtctcaatc acaaagaccc ccttaggcca ggccaggggt gactgtctct ggtctttgtc   1620

cctggttgct ggcacatagc acccgaaacc cttggaaacc gagtgatgag agagcctttt   1680

gctcatgagg tgactgatga ccggggacac caggtggctt caggatggaa gcagatggcc   1740

agaaagacca aggcctgatg acgggttggg atggaaaagg ggtgaggggc tggagattga   1800

gtgaatcacc agtggcttag tcaaccatgc ctgcacaatg gaaccccgta agaaaccaca   1860

gggatcagag ggcttcccgc cgggttgtgg aacacaccaa ggcactggag ggtggtgcga   1920

gcagagagca cagcatcact gcccccacct cacaccaggc cctacgcatc tcttccatac   1980

ggctgtctga gttttatcct ttgtaataaa ccagcaactg taagaaacgc actttcctga   2040
```

-continued

```
gttctgtgac cctgaagagg gagtcctggg aacctctgaa tttataacta gttgatcgaa   2100
agtacaagtg acaacctggg atttgccatt ggcctctgaa gtgaaggcag tgttgtggga   2160
ctgagccctt aacctgtgga gtctgtgctg actccaggta gtgtcaagat tgaattgaat   2220
tgtaggacac ccagccgtgt ccagaaagtt gcagaattga tgggtgtgag aaaaacccta   2280
cacatttaat gtcagaagtg tgggtaaaat gtttcaccct ccagcccaga gagccctaat   2340
ttaccagtgg cccacggtgg aacaccacgt ccggccgggg gcagagcgtt cccagccaag   2400
ccttctgtaa catgacatga caggtcagac tccctcgggc cctgagttca cttcttcctg   2460
gtatgtgacc agctcccagt accagagaag gttgcacagt cctctgctcc aaggagcttc   2520
actggccagg ggctgctttc tgaaatcctt gcctgcctct gctccaaggc ccgttcctca   2580
gagacgcaga cccctctgat ggctgacttt ggtttgagga cctctctgca tccctccccc   2640
atggccttgc tcctaggaca ccttcttcct cctttccctg gggtcagact tgcctaggtg   2700
cggtggctct cccagccttc cccacgccct ccccatggtg tattacacac accaaaggga   2760
ctcccctatt gaaatccatg catattgaat cgcatgtggg ttccggctgc tcctgggagg   2820
agccaggcta atagaatgtt tgccataaaa tattaatgta cagagaagcg aaacaaaggt   2880
cgttggtact tgttaacctt accagcagaa taatgaaagc gaacccccat atctcatctg   2940
cacgcgacat ccttgttgtg tctgtacccg aggctccagg tgcagccact gttacagaga   3000
ctgtgtttct tccccatgta cctcgggggc cgggaggggt tctgatctgc aaagtcgcca   3060
gaggttaagt cctttctctc ttgtggcttt gccacccctg gagtgtcacc ctcagctgcg   3120
gtgcccagga ttccccactg tggtatgtcc gtgcaccagt caataggaaa gggagcaagg   3180
aaaggtactg ggtcccccta aggacatacg agttgccaga atcacttccg ctgacaccca   3240
gtggaccaag ccgcaccttt atgcagaagt ggggctccca gccaggcgtg gtcactcctg   3300
aaatcccagc acttcggaag gccaaggggg gtggatcact tgagctcagg agttcgagac   3360
cagcctgggt aacatggcaa aatcccgtct ctacaaaaat acagaaaatt agctgggtgc   3420
ggtggtgtgt gcctacagtc ccagctactc aggaggctga agtgggagga ttgcttgagt   3480
ctgggaggtg gaggttgcag tgagccagga tctcaccaca gcactctggc ccaggcgaca   3540
gctgtttggc ctgtttcaag tgtctacctg ccttgctggt cttcctgggg acattctaag   3600
cgtgtttgat ttgtaacatt ttagcagact gtgcaagtgc tctgcactcc cctgctggag   3660
cttttctcgc ccttccttct ggccctctcc ccagtctaga cagcagggca acacccaccc   3720
tggccacctt accccacctg cctgggtgct gcagtgccag ccgcggttga tgtctcagag   3780
ctgctttgag agccccgtga gtgccgcccc tcccgcctcc ctgctgagcc cgctttcttc   3840
tcccgcaggc ctgtaggagc tgtccaggcc atctccaacc atgggagtga ggcacccgcc   3900
ctgctcccac cggctcctgg ccgtctgcgc cctcgtgtcc ttggcaaccg ctgcactcct   3960
ggggcacatc ctactccatg atttcctgct ggttccccga gagctgagtg gctcctcccc   4020
agtcctggag gagactcacc cagctcacca gcagggagcc agcagaccag ggccccggga   4080
tgcccaggca caccccggcc gtcccagagc agtgcccaca cagtgcgacg tccccccaa    4140
cagccgcttc gattgcgccc ctgacaaggc catcacccag gaacagtgcg aggcccgcgg   4200
ctgttgctac atccctgcaa agcaggggct gcagggagcc cagatggggc agccctggtg   4260
cttcttccca cccagctacc ccagctacaa gctggagaac ctgagctcct ctgaaatggg   4320
ctacacggcc accctgaccc gtaccacccc caccttcttc cccaaggaca tcctgaccct   4380
```

-continued

```
gcggctggac gtgatgatgg agactgagaa ccgcctccac ttcacggtgg gcagggcagg   4440
ggcgggggcg gcggccaggg cagagggtgc gcgtggacat cgacacccac gcacctcaca   4500
agggtggggt gcatgttgca ccactgtgtg ctgggccctt gctgggagcg gaggtgtgag   4560
cagacaatgg cagcgcccct cggggagcag tggggacacc acggtgacag gtactccaga   4620
aggcagggct cggggctcat tcatctttat gaaaaggtgg gtcaggtaga gtagggctgc   4680
cagaggttgc gaatgaaaac aggatgccca gtaaacccga attgcagata ccccaggcat   4740
gactttgttt ttttgtgtaa ggatgcaaaa tttgggatgt atttatacta gaaaagctgc   4800
ttgttgttta tctgaaattc agagttatca ggtgttctgt attttacctc catcctgggg   4860
gaggcgtcct cctcctggct ctgcagatga gggagccgag gctcagagag gctgaatgtg   4920
ctgcccatgg tcccacatcc atgtgtggct gcaccaggac ctgacctgtc cttggcgtgc   4980
gggttgttct ctggagagta aggtggctgt ggggaacatc aataaacccc catctcttct   5040
agatcaaaga tccagctaac aggcgctacg aggtgccctt ggagaccccg catgtcccaca   5100
gccgggcacc gtccccactc tacagcgtgg agttctccga ggagcccttc ggggtgatcg   5160
tgcgccggca gctggacggc cgcgtgctgt gagttctggg ctctgtgcca gcatgatggg   5220
gagggcgacg cgcatttctc acacggcagg gagggccaca cgcgtttgtt tctcacacga   5280
tgggcagggc gacacatgtt tgtttctcac acggcgggga gggcgacggg catttctcac   5340
agggcgctcc ctgggtcttt tactcacata ggtctaaatc ccatgtaaac acgtgttcag   5400
gactcaccaa gcccctgctt gtcatttaac tcaggaaaac tctcaggaac gacagcactt   5460
ggatttgcct taatcttaag agaagttgcc ttcggaaatg cgtttttctt tttttgctca   5520
ttcatttact cagtgtccac gcactgaccc tccgtgccgg gtggtttgga tcctgctccc   5580
ggggacagac acacagtgag gggaagccat aagcaagtcc atgcagacac agcgtcaggg   5640
agtggtcatg cagagagcac gctagaagcc agctgtgcag acacggggca gggaggtccc   5700
ctctagaagc cagctgtgca gacgcagggg acagggatgg cctctctgga agccagctgt   5760
gcagatgttg gggcagggg tggcctctct ggaagccagc tgtgcaggag tggggggtgg   5820
ggaggccact ctggaaacca gctgtgcaga tgcaggggac aggggtggcc tctctgagct   5880
gacctctgag tagagagacc caagagaagt ttctcaaagc atcttatcaa gctaggtatg   5940
gtggttcatg tctgcaattc cagcactttg ggaggccaag gcgagagggt cacttgagcc   6000
caggagttca agaccatcct gggcaacata gcaagacccc atctcttaaa aaataaaaat   6060
aaaaaattag ctgggaattg tggcacatgc ctgtggtcgc agctactcag gaggctgagg   6120
caagaggatc ccttgagccc aggggttcga ggttgcagtg aaccatgatt ttgccactgc   6180
acttcagcct tgctgaagac cccgtctcaa aaaacaaaca acaaacaggc atcttatcag   6240
atctcggtct tgaaagcact cagcgcagtc ttgcccaggg gagggtgggt gtggtgtgag   6300
cccgtcctgc gaaattagct gtgctgtgtt aacagaggac gcgtcttcct gtggaccgga   6360
tttatctgcg gctttcattt ctcggaggtg ctgtttgcct tgcacttgat ccccagaaaa   6420
cctcaggggt ccttctgggg catggctggg ctgggatctg ggaggacttt ggccacaagc   6480
tcctaggcct ggaaaggttc tgttcagccc ctgcccagcc ttgcttgggg tcatgggaca   6540
ggcatgtgtg ccagttccgg taccagccag ttcctggagg tcagcccctt gggggcccct   6600
caggggtggt gtgggcccag ccaggcggtg cgccccttct gatatgccct gagagttgat   6660
cacgctggtg ccagggtgcc aagggctgca gggctcggca cggccgcctg tcccagggtc   6720
agtgtgctgc agggctggcc aggccactcc gccctcccag ggcaccaggg cccgggggtg   6780
```

-continued

```
ctctctgggt gctctcaggc tcgtgtggcc ccttgggtgt gagcaagcct ggctggcctc   6840
tgtcccgcag gctgaacacg acggtggcgc ccctgttctt tgcggaccag ttccttcagc   6900
tgtccacctc gctgccctcg cagtatatca caggcctcgc cgagcacctc agtcccctga   6960
tgctcagcac cagctggacc aggatcaccc tgtggaaccg ggaccttgcg cccacggtac   7020
agcagcgggc ggcgggcggc gggcgggggc accgagctgg ggagcgcagg tgctgaagcg   7080
ccgtctcctg catgtcccag cccggtgcga acctctacgg gtctcaccct ttctacctgg   7140
cgctggagga cggcgggtcg gcacacgggg tgttcctgct aaacagcaat gccatgggta   7200
agctgcccac cgcccagcgc ccgggccggg gtctcctccg tgctgcctgc cctggagact   7260
ggaggtccgc atgaggggcc ctgggcacgg tgctgggcct tgtgttttct gggaaatgag   7320
tcctatgggc tgatgcctct cccaactctg gccttctgtg ctcctaagga gggttctggg   7380
gccctgcctg gaggtgggct ggcaccacat atctttccgt cccatgccag gttcctcctg   7440
agtcaggctt agcacggctt ccccaggcca ctctgagctc ctcatgggga gagagcctca   7500
actctctgcc tgtgattggc ccatctgtgg ggtgcagagc cctccaagtg aagaatctgt   7560
cccccaaccc cagagctgct tcccttccag atgtggtcct gcagccgagc cctgccctta   7620
gctggaggtc gacaggtggg atcctggatg tctacatctt cctgggccca gagcccaaga   7680
gcgtggtgca gcagtacctg gacgttgtgg gtagggcctg ctccctggcc gcggcccccg   7740
ccccaaggct ccctcctccc tccctcatga agtcggcgtt ggcctgcagg atacccgttc   7800
atgccgccat actggggcct gggcttccac ctgtgccgct ggggctactc ctccaccgct   7860
atcacccgcc aggtggtgga gaacatgacc agggcccact tcccccctggt gagttggggt   7920
ggtggcaggg gaggcaaggg gctggccggg acgcgtctcc tcaggcccca gcagacggtc   7980
ccgtgttgtg gctgcaggac gtccaatgga acgacctgga ctacatggac tcccggaggg   8040
acttcacgtt caacaaggat ggcttccggg acttcccggc catggtgcag gagctgcacc   8100
agggcggccg gcgctacatg atgatcgtgg tgtgtgcccc cacactgtgg gtctttggga   8160
agggggccgc ccggtgccca gtggctcctt ctctgtgcag cgtcatcctc gtgcctgtgt   8220
ggtcgccgag gatgttttct gagggtcttt gtgatatcga aggaatatca agaagtttgc   8280
aggcttggcc ccagctgtcc agggaggtcg ggtttgaggg tccccagaaa tggccgggtg   8340
ctactcaggg ttctgtcaga tgtaggttac ttgaactgcc ttaaagcaaa aggccagggg   8400
catgataaac tgatgtcacc tggtcctgga aagtggaggg cccggtgggc ctgggcatgg   8460
gtatcgctgg aactgtggag gctccgtgtg ccttctggcc gtgcctctcc ttctggccgg   8520
ctctgaatcc ctggaaagga cggcgtgagt gagggcagct tccagccctc atgctggcac   8580
cacagagcgg agacttcttc ccatcagctc ccatagaaaa gtcccaaagc aggactcttg   8640
agtcacccag cacaaagagg cccttccctg agccagtccc acagccagaa ggatgcagtt   8700
tgggggctgg tccagcccga gtctggtgtc cggcacgatg gccagaggag gaggtgggag   8760
gcagggcgag ctgaaaagat ccaacagttc ctgcccggaa gatccacttc agcagaggaa   8820
gcacagatga gatgtggggc tgtgctgatg ctgcctgttt ccatccctgc cttctgcagg   8880
cagcaaacat tagtagccct taagagcagg agtggaaaca cagacttttt ctttctcaca   8940
tttttttaat tataaaagaa aagtgattac tgtaggacac ttgggaaact ctagaggttt   9000
aaagaaaagg taaagcttcc attccggcgc gcccctcatc agccagctgg tcctgactcg   9060
cccggccctg gctcctctcc aggcaggcgt gtgcaggcat gtgcaggtac acaggcaggc   9120
```

-continued

```
gtgctgtaca cacgcatgat gtcatcccca gcctcatcct ctcactgtct cagttttccc   9180
cgtggctggc gccagggctc tgggccaccc tcaccttgac gggtttccct cttcccagga   9240
tcctgccatc agcagctcgg gccctgccgg gagctacagg ccctacgacg agggtctgcg   9300
gagggggggtt ttcatcacca acgagaccgg ccagccgctg attgggaagg tagggcgagg   9360
gtccagggga cgggggttag aaagcagagg cctccagcca gggggagccg gcagctgctc   9420
aggaagacgg tgggatttga ggagccatca cgcccagtgg gacagctgag aggaatgggc   9480
cacagtggcc cgtgacgatg gtggctccta caaggaatgg ccccgtgagt tcttccatca   9540
gcaggccttt gacttcatgg gcagctgggc ctggcccagg cacaagccct gcagaccctc   9600
agtgaggcct tagggtcctc cttgtcctcc cagcccccca ggggcctcca ggcagggccc   9660
ccgctgaggg agcagctagg gagggtctgg tgcggatgtg aggctgcctg gcagggcttg   9720
cacggggccg tctccgctgc ccttctccct gacgctctct ggttctgcag cccagcccct   9780
gggtggacgt gttgggggtg gcccctcgtt ttcccagggt tgaggcccct tggccccgca   9840
tcagtgcctt gtggagaaag agctgctcat tgacctccag ggtgcaggtc tctcagattt   9900
gcaaatgtgg gcatccacta agagtgaggc tgcccctctg ctcaggctga ggctcagtgg   9960
ggcttccatg caggccctgg gtggggccgg gtctccccac tccagcctct cgttgtccag  10020
gtatggcccg ggtccactgc cttccccgac ttcaccaacc ccacagccct ggcctggtgg  10080
gaggacatgg tggctgagtt ccatgaccag gtgcccttcg acggcatgtg gattgtaagt  10140
gtggcccccct cctgagcatc cccaaggcct ctggggacta ccacaccctc ctcactctgg  10200
gcagagtcac ctaccagcag cgcttctctt gcaggacatg aacgagcctt ccaacttcat  10260
caggggctct gaggacggct gccccaacaa tgagctggag aacccaccct acgtgcctgg  10320
tcagctcgcc ccccacctac cctggggact taatcaaatc agagactccc ttgtctggcc  10380
tgggagactt agcaccctca tctctgagaa gcagatgggc cagcggggaa aggggtgggg  10440
ggggatcccc aggagaaagg ctcaggctgg gagactcagc caagcagtgc agacagggtg  10500
ggtgcagagg cacaggccct gccggaggag acgccgctca caggtgcttg ccagagcaca  10560
gtgaggccga ctcgactcag agccgtctcg ataggcgcag ggaccatgca gcggagacct  10620
acccacccgt ggggagaggt caggcccaac tcgaatgcag cacgggcaag tggatttcta  10680
gccagggagc agggtgggct cagaggtggg aattaccaag aggaagcatg ggggtcaggg  10740
ggattctggc tgaactgacc cagcaggatt cttgctgaag gcaggccagg gtgaccagac  10800
atcgcctgag gggtggtgga ggttggggct tctcgccaaa ctgtcttagc aggaatggca  10860
gaaactgggt tttacaagga agtacaagga tgggcctggg agaaggtttg ggggcctgag  10920
gctatagttt ggcccagcaa agaatcagtg agaggatggg gttttgggct taggtaaaca  10980
ggcaggggag tgcttgaaat gggccaagag acggtggatg tgaagtctgg gggtctgcag  11040
agcccaggct ccagcacccg cccagccctg tcttagaagc agtggagatg attacccagg  11100
ttcccgggta acgccagccc cacagaggcg tggggagcgg ctgcaggtgc acctccaggg  11160
ccagcctgaa gaggcagcga cctgcacagg ggctcctggg aggtgggggg cagggagggc  11220
accttggagc ctgccgggag gaagctccct ggaaaccagc ccccgcctct tccaggggtg  11280
gttgggggga ccctccaggc ggccaccatc tgtgcctcca gccaccagtt tctctccaca  11340
cactacaacc tgcacaacct ctacggcctg accgaagcca tcgcctccca caggtgaggg  11400
ccacatcccg ccccactggg ctctgccctc acagcctgtc ctacaaggtt ggggcctctg  11460
cagggcctca gggaggagga aaagcggagg cccagaccac ccggggcccg ctggcggccc  11520
```

-continued

```
gagtgctctc cccacctgct gcctgcaccc cagcctgaag ctggagcgct ccttcccact  11580
tcatgcctgg ggcttggaga ggaaggaccc tggatgctga caggagtctg catcagcggg  11640
gacctcatga ctcctgtgag gctggggggg gtcctggctc acctacaggc atcaggtggc  11700
ccagacagag gcaactgtgc ccgcagacat gggcagtagc ctcgccgtcc tcctccccag  11760
cctctgcctc atcccagaaa gctccttgct cccagctctg ccctgctggt gacagggttc  11820
ccgagtgacc ccgctccaca cagccctcac ggtgtccccc accaccccag ggcgctggtg  11880
aaggctcggg ggacacgccc atttgtgatc tcccgctcga cctttgctgg ccacggccga  11940
tacgccggcc actggacggg ggacgtgtgg agctcctggg agcagctcgc ctcctccgtg  12000
ccaggtgagc tcctaccagg aggggctgct cagcagagta gagccggggg cctctatggg  12060
aggcttgccg gggcccccca cccacttagc aggtggggct ctgggtcact tggcctgagc  12120
tggctctgct gcagcagcct gaggaccagc ctgactctgc cctcccagaa atcctgcagt  12180
ttaacctgct gggggtgcct ctggtcgggg ccgacgtctg cggcttcctg ggcaacacct  12240
cagaggagct gtgtgtgcgc tggacccagc tgggggcctt ctaccccttc atgcggaacc  12300
acaacagcct gctcagtctg gtagggtggg ggtggcggcg tggcaggtgg gcgatcccac  12360
ccacccaaga ctctcccctg ggaattccgc ccctgctgga gaagcacccc atgctgggtg  12420
gctgagaagt gcagctctcc cgaggcaggg actccagggg accgcggccc cagcacccaa  12480
gtgcttcctt tgcccccgcc tgccctgcag ccccaggagc cgtacagctt cagcgagccg  12540
gcccagcagg ccatgaggaa ggccctcacc ctgcgctacg cactcctccc ccacctctac  12600
acactgttcc accaggccca cgtcgcgggg gagaccgtgg cccggcccct cttcctggag  12660
tgagtgacct aggcaggggc ggtggcccat gtgtgccctg ggggaggggc acgtaactcc  12720
caggcagccc tgtcctgctg tgggctgtgt tccccaggac ccagcaggtt gccgctgagt  12780
gagacaacat ttgggcctgg cttaaggggg aagggcagca agaaaaccca gtaatatccc  12840
ccagacaggc cgtagtacac acgaggagtt cctaacaaca gccctgcaca tcagtgtgtt  12900
gagggaggat tcccagagag taaggtgatt agttaactat ttgcagaagt caatttattt  12960
ttcttgcata ccatagaaac ataagttcca gataaattaa atagttaatg tcaaaaatca  13020
agctgtggag gccaggcacg gtggctaacg cctgtaatcc cagaactttg ggaggctgag  13080
gcgagtggat cacctgaggt caagagttcg aggccagcct ggccaacatg gtgaaaccca  13140
tctctactaa aaatacaaaa attagccgtg catggtggtg ggcgcctgta gtccctgcta  13200
ctcaggaggc tgaggccaga gaatcccttg aacctgggag gaggagattg cagtgagccg  13260
agatcacgcc actgtactcc agcctgtgtg actccatctc aaaaaaaaaa accaagctgt  13320
gaaagactcc acaggaaaag ataagtgaat gtgtatctct ggggaaaggt ttcatttaga  13380
gaaaaaaaaa aaaaaaaggt gaactttatt tgaccatagc agaaaaaaaa atgtaaatct  13440
ctgaatataa acacaaaaag attaaaactg ctctgaacat ggactgtaac agcagagaag  13500
gcattgtcaa taaaacagca aatagctact cttcctaata ggtagagaac tcatacgttg  13560
gtaagaccaa gactaagaac caaattggag gaacactgtt tgcaaaacag gagatacgaa  13620
tggtatccac acattcttca cccggaaatc caagaaacgc aatttgtgtt ttaattacta  13680
ttttaatgac cttgttgttt ctgtcactac actttttttt tttttttag tggttgccct  13740
agggattaca attaacatct taattttagc ctcgttggaa ctgatgccaa cttgctttca  13800
atagcataaa aaagctttgc ttctatgtgg tttccattgc ctctcgttcc tctgtgctgt  13860
```

-continued

```
tacacgtctg tatccatgat gagcccatcc acgcagattt ataatgaccg ccttattcaa  13920
ttatctttta agtcaaatag gagggaaaaa tgggttacaa acaaaaagta catacacact  13980
gtctgccttt tatatttact gatgtagtta cctttaccca tggttttatt tcttcatgtg  14040
gctttgactt cttgtctaac atctttcatt tacagcagaa ggactccctt tagtatttat  14100
tgtagggcag ttctgctagt gatgaattct ctcagttttt gttgacttca gagtctctta  14160
atttctcctt catttttga aagttctgct caacgtaggg ttcttgactg gcggtcgttt  14220
ctctgaacac tttgaacttg tcagcccatg gcctccgtgg tttctgctga gtagcttctg  14280
tcttgcctct tcccagattc tctgtctttg gcctttgaag tcccgatggt gtgtctaggt  14340
gtagatctct gagtttatct tactgggagt ttgttgagct tcttggacgt atgcattgat  14400
gtttttcatc aaacttgggc ggtttttcag ccattacttc ataaaatatt ttttctgccc  14460
ctttctgtct tctactctgg gacttccgtt ccacacattg gtatgcttga cggtgcccag  14520
gggtctttgc agctctgttg actccttcct cgttgtgttt tctttctgtt cttcagactg  14580
cttagtctga ctgccctgtc ttcaaggtca ctgattcttt tttccaccag ttctcatctg  14640
ctgttgagcc cctctagtga acttctcatt ttagttgctc tcttttcaac tccagaattt  14700
ctgtttcatt cctttacgtt tctctcgtta aggatattcc ctatctggtg agtcatgttc  14760
tcacactttc ctttagttct tcagacacgg tttcgctgag ctctttgaac acatttaaag  14820
tagctgacgt aaactctttg tctagtaagt ccaatgtctg ggcttctcta gggacaattt  14880
ttattaacta ctgtcccccc atctgtgggc catactttct tgtttctttg cgtgtctcat  14940
acatttttgt ttcagactgg acattttaaa cgcagctgct gtggtcatca gattccccat  15000
ccccctcagg tctcgttgct attgctgatt gttttgtgac tttcttgagc taattccata  15060
aggtctgtgt tcttcattgt gtgtggccac caaagtctct gcttgactag cttagtggac  15120
agccaataat tggtcagata tccttcacag atggcatccg tgagtctccc agcctttgct  15180
ggggcgaggt ggggagcacc gtcaacactt agctaggcca aggattcttg ctgttcttac  15240
aaagattcag ccattttgtt aaatacatgc tccccagatg gctgcaaacc cttggttagt  15300
ttcaagagtc ctaaaaatgt caactctgac catttttgcc gatgttcctg ttttcacaga  15360
ggagaggatc ttgagagggg cttactccac catcttcact gacatcactc caagaaatgt  15420
attttgcaag aaatattttg aagcagaaag acaccattta ttttgcccat gaattagaat  15480
acattagaga aaataagact atcccttgct ggcaagaaca cagtgacaca gtagggtgga  15540
atataaattg gcacatttgt ggaaagcaac agtacatatc agtcaatgtt tttgagattc  15600
acattgatgc attaatttta caaatagaaa tagggcctaa agaagtcacc tcaaaaggca  15660
tgaacgctcc atgaatgtat ccatgcaggg atcatagctg agcactggat gccccctgca  15720
catccggggg caggaaacag gacagggcag agctgcgtca cagggcagga cagtctccgt  15780
tagacggaga atcctccgta gagctgcttg cacgtgtaca ttcatctttt tgtcagatgt  15840
taattcaagt tgcctttggt tgtgggactg ggaggatctt ttctctttgt tgatactttt  15900
tcgtactttc caaatacttg actgatgagc acatgctgcc ttggttaccg gaggataagt  15960
gagcgagcaa agtgaggcca gtgctgtgtc catcctggtg cctcaagcac aagcccctat  16020
tcctgccctg agcccagctg ccggcatgtc cggggagaag gcttctccca gctccggcat  16080
tgacttctat ctgctggaat catccctgcc cgtctgacct gagtcctcca agtcctccgg  16140
caccttgagc tccagagagc agaattcagc ctcttcctgt gcctccccag ggtgggcata  16200
tgagccagcc ccatcccatt catcacccgt atgcctgtgt gcccatcccc cttgcaggtt  16260
```

-continued

```
ccccaaggac tctagcacct ggactgtgga ccaccagctc ctgtgggggg aggccctgct  16320
catcacccca gtgctccagg ccgggaaggc cgaagtgact ggctacttcc ccttgggcac  16380
atggtacgac ctgcagacgg tgagtctggg gaccctaaac cccggggaga ccctaaaccc  16440
cggggagacg ggagaccaga gcagccctcc cacctgcccc ctccacccag ttggtgtgac  16500
caggtggcgg aaagaggaac gtatgtgttg agtcccggcc atgtgccagg cccccacccg  16560
gctgctccgc acccatcagc ctctccgctc ctcacaccat ccccatttcc cagatgagca  16620
gactgaggcc tgcttgcaga acctggccaa gtcccacggc catcacaggc tgtgcctgtg  16680
ctgagctggc atacccaggc ctctcaggct ctgtccccac tcagtagcca ggagggtccc  16740
tacctacagt gagccctgag tctgcgcctg aagtcacagt tcagcccgtc tgtgccaggc  16800
ctcctaggcc tccacgtgga gccccgggag atggagagcg tggttcctga ggacagcatg  16860
ggggcctcgg cacggcccag aatcctcaaa gcaacatctc cctccaggtg ccaatagagg  16920
cccttggcag cctcccaccc ccacctgcag ctccccgtga gccagccatc cacagcgagg  16980
ggcagtgggt gacgctgccg gccccctgg acaccatcaa cgtccacctc cgggctgggt  17040
acatcatccc cctgcaggta cctgggccag gcggctatgg tgggggtgtg gacagcacac  17100
tgcagagctg ggggaggcac agggagatgg tgggggagag gcccaggtgg ggcttctgag  17160
gggccgcccc ccgcagtgta ggttatcaag gagccagcca ggccagtgag gtggggaggg  17220
cacagcccca caaaggcgtg gagcatggcc ggcaggagct cagtggtctg catggtggag  17280
gttctgccgg gcccggcctc gggcagccgt gggatagcac ttgaggtggg gaaggtcttg  17340
ggtcatcacc acggggttcc agcccctgcg gccggccgca ggtgttcctg cagatcctag  17400
ttactggcag cctggtgctg taccagccta gcattcccgg gccctggagg cctccacctc  17460
caccagggtg gggatgatga catcacgtgt ccttcccttt ccagggccct ggcctcacaa  17520
ccacagagtc ccgccagcag cccatggccc tggctgtggc cctgaccaag ggtggggagg  17580
cccgagggga gctgttctgg gacgatggag agagcctgga agtgctggag cgaggggcct  17640
acacacaggt catcttcctg gccaggaatg tgagtcctgg ggctgctcag gctggtgggc  17700
aggggccggc tcggggttga gaaggggtga ggggacctgg gcttggggggt cccacgatgg  17760
ctacctgcca ctaggacact ctagcaggtg gcctggggtc ctagagtgag cagtggggcc  17820
gtgcactctg ccctttcgtg tacacagagg gaggtcacct ccctgatgcc atcatgagtc  17880
cctgttctca tgggtgttcc tgccccagct gtctgctgac acctccacat tctctgcctt  17940
ttcatctctc tctgctcggc ccagaacacg atcgtgaatg agctggtacg tgtgaccagt  18000
gagggagctg gcctgcagct gcagaaggtg actgtcctgg gcgtggccac ggcgccccag  18060
caggtcctct ccaacggtgt ccctgtctcc aacttcacct acagccccga caccaaggca  18120
agagggccca gagtggcaca gggatcgcgt cccccagccg tggtgcaggg ggcagaaggt  18180
gctgggcgtc ctggtgaccg atgccaggaa cagaggatgc tgggacctcc caagggggtc  18240
tttggggagg agtgggaagg gtcaggccac acaggctgtg cctttcctcc tcctgtgtct  18300
acacgtgggt gatggggcca caatgacgac ctctgagccg tgttgaagca gcaccgtgtt  18360
tctggcgtgc gttaaggtga cccgcactga gagccggggt ccccctgcgc ctgccgggga  18420
ggaaccgggt gcgaagcatc ccagggccag acggagctgc cccctgagcg ccgggcctcg  18480
ctgctgctgg gatctcgggg ccagatggag ccgccttctg agcgctgggg tctcactgct  18540
gctgggatct cgggctgctc catttgtgct ctctcttttt ccaggtcctg gacatctgtg  18600
```

-continued

```
tctcgctgtt gatgggagag cagtttctcg tcagctggtg ttagccgggc ggagtgtgtt  18660
agtctctcca gagggaggct ggttccccag ggaagcagag cctgtgtgcg ggcagcagct  18720
gtgtgcgggc ctggggggttg catgtgtcac ctggagctgg gcactaacca ttccaagccg  18780
ccggcatcgc ttgtttccac ctcctgggcc ggggctctgg cccccaacgt gtctaggaga  18840
gctttctccc tagatcgcac tgtgggccgg ggccctggag ggctgctctg tgttaataag  18900
attgtaaggt ttgccctcct cacctgttgc cggcatgcgg gtagtattag ccaccccccct  18960
ccatctgttc ccagcaccgg agaagggggt gctcaggtgg aggtgtgggg tatgcacctg  19020
agctcctgct tcgcgcctgc tgctctgccc caacgcgacc gctgcccggc tgcccagagg  19080
gctggatgcc tgccggtccc cgagcaagcc tgggaactca ggaaaattca caggacttgg  19140
gagattctaa atcttaagtg caattatttt taataaaagg ggcatttgga atcagcttct  19200
gcgggtctct ctgggattca gggcagggag gatgtatcca ggggccctgg aacagaggta  19260
gctcctttgt cctcagcagg cccccagaca ttcccacagt gggtgtgcgc cgtcctctgt  19320
ctcaagccgg catccatcac gtcatgttcc catgtcacga ggcctgacat cacctcatgt  19380
cctgtcccca tctcacctca catcccgtca cctcatgtcc ccgcatcacc taaagcccca  19440
tgtcaccttt gtgtcccata cccccatctc acatgcctac ctcatgtccc catgtcacct  19500
tcacgtccca tctcacctca cctacctccc cacctacctc ccctcccctc ctcccctccc  19560
ctcctcacct gacctcccct ccccacgtca cctcccttcc cctccccacc tcacctcccc  19620
tccccacctc ccctcccctc cactcctcac ctaccctccc catgtcacct ccccttccct  19680
ccccacctcc cctcccaccc cacctccctt cccctcccct cctcacctga cctccccttc  19740
ccatgtcacc tctcctcccc tcccaacctc ccgtccccat cccacttcac ctcccctcct  19800
cacctgacct cccctcccta tgtcatctct cctcccctcc caccgcacct cccctcccct  19860
cctcccctca cctgacctcc ctaccccacc tcaccccctc tcccctcctc acctcctctc  19920
ctcctctccc cattcatcct cacactcctg cttcccccat ctctaaggtg actggggaat  19980
gtccagtggg tgttaggcat gtggtgggag tgtggccccc agggctgtgt agacaacagg  20040
accctgcaag gaaggggctt tccaacagtg gggcctaaga ctttaggcag aggccagaaa  20100
tctgtcccca agtgatgcag ttagagagga tttcaggccc aggttctccc tggcaagccc  20160
agagaaaggg aaagaagccc attttattga aataacagca ggagaaatca ctgcccttag  20220
ccagtcagac gcttcagttt atcacttaga attaatgcag tggctcacac ctgtaatccc  20280
agcactttgg gaagtccagg cgggcagctc acttgaggtc aagagtttga gagcagcctg  20340
gccaacatgg tgaaacccca tctctactaa aaatacaaaa ttaaggccag gcgcagtggc  20400
tcacgcctgt aatcccagca ctttgggagg ctgaggcagg cggatcacga ggtcaagaga  20460
tggagaccat cctggctaac atggtgaaac cccgtctcta ctgaaaatac aaaaattagc  20520
tgggtgtggt ggcacacacc tgtagtccca gctacttggt ctcgcaaggc tgaggcagga  20580
gaatcgcttg aacccgggag gcggaggttg cagtgagccg agatcgcgcc actgcactcc  20640
agcctgatga cagagcgaga ctgtctcaaa aaaaaaaaaa attaggcatg gtggtgtgtg  20700
cctgtagtcc cagctactca gaaggctgag gcacaagaat cacttgaacc cgggaggcag  20760
aggttgtagt gagccaagat cgtgccactg cactccagcc tgggcgacag agtgagactc  20820
catctcaaaa aaaaaaaaaa aaaaggccag gcgcggtggc tcatgcctgc aattccagca  20880
ctttggtagg ccaaggcagg cggatcacga ggccaggagt ccgagaccag cctgaccaac  20940
gtggcaaaac cccatctcta ctaaaaatac aaaaattagc tgggtgtggt ggcacgcgcc  21000
```

-continued

```
tgtaatctta gctactcagg aggctgagga aggagaattg cttgaatctg ggaggcggag  21060
gctgcagtga gctgagatca cgccactgca gtccagcctg ggcgacagag tgagactcca  21120
tctcaaaaaa aaaacaaaag aagtggccaa ccccgaagtc ctctgcagag cgatggatta  21180
cttttgccac cttcctgaaa accaggagca gaaagtacag tgacttcccc gtggagcagc  21240
atgacatccc tggggggcag tgtgtctacc tgggtgacca gcactattgt cttctgggtc  21300
agcttttgta gaagcggaca ctgctcttct gccatgtcac aggccagggc ctgacccccg  21360
tgtgccactt ttaccatcca gattgacatc actaagtcat ctcgcgccct aaagttcctc  21420
tgtaaggtgg acgtagtagt gacaataaca tatgttactt cctcccctca tcctagtccc  21480
atgtggggtt aagaagcagg aacgtttgtc ttgaggccag cagcgtgcct ggtctcggtg  21540
ctgagggcga cctgccctaa cgctctgcca ggctcgccag gtctgcagtt gacacccaag  21600
acggtcaggg agggttgatg gagcgtggta gcctcggcca gcctggaccg accatcagcg  21660
tcctcacctt ctgtgccacc gcccagcctg gcagggccac tgtagcctta gccccttgta  21720
ggatctgacc cttccttggc tgctgtaacg aaatacccaa gactgggtaa tttataaaca  21780
acagaaatgg atttctcaca gggctggagg ctgggaagtc caagatcgag gcaggttctg  21840
tgtctggtga aggctgctgt ctgtatcata aatggcgcac tctccatcat cgtggtagaa  21900
ggcgaagaca agctcccttg agcgctaaat gccactgatg aggatggagg gccctcagga  21960
ctcatcacct cccaacagcc ccaccacttt tttttttttt ttttttgag accgagtttc  22020
actcttgtca cccaggctgt agtgcaatgg tgcaatcttg gcttattgca acctttgcct  22080
cccaggttca agtgattctc ctgcctcagc ctcccgagga gctaggatta caggcatccg  22140
ccaccatgcc tggctaattg gatctttagt tgtatttgta ttttagttta tttgtatttt  22200
aattgagatg ggatttcacc atgctggcca ggctggtctt gaactcctga cctcaggtta  22260
tctgcctgcc tcagcctctc aaagtgctgg gattacaagc atgaggcact atgtccggcc  22320
agccccacct cttaaaacca tgtcattggg gattaggttt caacaggaat ttggggtggg  22380
ggcaaacctt cagaccatag gacagggcta tcaggagtcc tgagtgagga ggttggcatg  22440
gggtgggaca gtgctccctg tgtgggaagg gacagggtcg gagggggag aggagttgtt  22500
tccatcctct gagaggccag gggtctcctc agggtggtcc aaacggtaca gcccattaca  22560
tgggacgctg gcctgtgggc acctcaaggc agcttcatct gtttctcacc agtgcctgat  22620
acaggccctg cctcagtggg accctattga acttaggtga attttaaagc aataggccag  22680
gtgtggtggc tcacgcctgt aatcccagta ctttgggagg cctaggtggg cggatcacct  22740
gaggttggga gtttgagacc agcctgacca acatggagaa accctgtctc tactaaaaat  22800
acaaaattag ccaggtgtgg tggtgcatgc ctgtaatccc agctactcag gaggctgaga  22860
caggagaatc atttgaaccc gggaggcgga ggttgtggtg agccgagatc acgccactgc  22920
actccagcct aggcaacaag agcgaaagtc catctcaaat aaaaataaag caatgtggat  22980
gtggacccca ggcagcttgc agcggagacg tcttagtgcc ggggagcgtt caagctggca  23040
ccctccgccc tgggagaaga catcctgggg tctcgtggtc agccgtctca tatgtctccc  23100
agctcagtct ctaaaacaag gcctgctgtt ggtgacaaaa cgctcttggc tcatgttctg  23160
ggcaatgagc tactgcgtgt ggtgggccag cttcacaggt gtgacccatc gcaggcccac  23220
aggccccgag ctcagcaggc tgcagctggg tttaatgctc cacggtcacc atgttgaaat  23280
tgtgaataac ttttgaacaa ggggccccac agctttcatt ttgtgacggg ccctcggcaa  23340
```

-continued

```
attctgcggc tggtcctgca aggggtggtg cgttctctcc cgtttacgtt ggtatagatg  23400
aatataaacg cttcctttct ttccttgcct ggtggggaat ggatcagaaa gccagggctg  23460
atgatagaaa ccagcagaga atctccaagt gtaagacatt agtcaaaggc ccggcgtgga  23520
gcccacaggt ccttagcgtt cggaagacga ttgccttccc agcccactcc aaggaagaat  23580
cagtgctgtc tggcagcagc ctccaggtgt gtctccacaa aggcccagct ttcctttttg  23640
caaatcaatg acatcaataa tccgttacat ggcctgcaga gaagccctct ggcggccact  23700
gtggggccct gtgggcctta tgcctgctct tcctgatctg gtggaggctc agagaggagc  23760
taggacaagg gatggtgccc ctataccacc ccaccccac atacgtgcct gcagaaggcc  23820
acatgaccag gattatggtg ggtgagggcc agagggaagg cccaggtgag agggtggaat  23880
gtgaacaggc tggttatttg cgtgccaggg acaagagaga aaaaagctca gcattagcag  23940
agaagacgga cttctgcggt ggcacctaca gctgttccct tggcctccca aacaacccag  24000
gtgtgacgtc gggaaccggg aatgcaggca acagagtgat tccagctgcc tcacaaggaa  24060
gagggtgtgt gggaagagca gagcatccgg gctggaagca gtcagaacca tgcgtgcagc  24120
cggacactca ttgttcttcc ccacgtgtgc tgggcacccg ctctgcgtca ggctctgttc  24180
caggagttgg gtgaaacggt gactgaaata gacagaactc ctgtcggtga tgcccacgtg  24240
agagaatata atcaatggac aatgcaccgc acatatttaa aatgtgcaaa ttgatccgtt  24300
ttgacatgtg aatgtctgtg aaccagctct acagttaaga tggtgaccat ctccatcacc  24360
ctcaaagtct ccagctaccc actgactgga aaccactggt atgtttttttg tcaagatata  24420
tttctttgta ttttatagaa ttttgtataa aggggaattt ttttgtcaca cactactcaa  24480
cataatttct ttgagattta tccatcaata actcatcctt tttagttgct aaatagtttt  24540
ccactgtatg caaatgccac catttcttta tctgtccttt atggatatca gaattgtttt  24600
tgattttttt gtttgtttgt ttaaagacag ggtcttgctg cgcgtggtgc tcacgcctgt  24660
aatcccagca ctttgggagg ctgaggcagg cagatcacct gaggtcagga gttcacggct  24720
agcctggcca acatggggaa accccatctc tactaaaaat acaaaaatta gccgggcgtg  24780
gtggtgggcg cctgtaatcc cagctacttg ggaggctgag gcaggagaat tgcttgaatc  24840
caggaggcgg agtttgctgt gagccgagat cgtgccattg cactccagcg tgggcaacag  24900
agcgagactc catctcaaaa aacaaaacaa aacaaaaaca gggtcttgct ctgtcaccca  24960
agcaggaatg cagtggcacc atcatagctc accatagcct caacctcatg ggtttaattg  25020
atcctcccac cttagcctcc tgagcagcct gggactacag gcatgcacca acacatgtgg  25080
ctaattttta aaatattttg tagagatggt gtctcactgt gtttcccagg cttgtctgga  25140
actcctggcc tcaggtcatc ctcctgcctt ggcctctgaa agtgctggga ttacaaacga  25200
gggccatcac cctcagcccc tctctgcaat ttttggctat tatgaataaa gctgctatga  25260
gcagtcatgg acaagtcttt gacattattt tgtttctctt gggcaaatag caaggatgat  25320
gtggtcagtt catacgggag gtaaactatt cattgtttaa gaggctgcca aactgtttcc  25380
aaatcgctgc accattctgc attcctcccg actgtgcagg ggagttggca ggggctgcgt  25440
atccgggcca gcattggcgt ggtctgtttc cttttagcca ttctagtgac tgtgtatctc  25500
actgtggctc ttacactccc ctaatgacta ttgatgttga acatcttttc acccacttat  25560
ctgtcagcca taaatcttct ttggtaaagt gtctgttcgc ctcttttgcc cattgttaaa  25620
ctgggtcgtt ccttattata gagttataac atacgtcaat tttctagtgc tgccgtaaca  25680
catgaccaca gtttgaggga attaaaataa cacaaatgta tttcatcaca gttccatagg  25740
```

-continued

```
tcagaaattt gatacaaggg ctctcctggc tgaaatcggg gtgtcagcag ggctgccttc  25800

ctttccagaa gctccagggg agaatccgtc tccttgccca catgggctac tggcagaatt  25860

gtttcatgca gttgtagcac tgaggtctct gtttcccttc tgtcagtcag aggtccttct  25920

cagcctacag aggcttcccc catatcttgg ctcatgcctt tttcaacccc agaaatgagg  25980

gacttgagtc cctctcatgc ctgtccttcc ttccatcaca tcattctctg accaaccata  26040

gccaaagaat agtcttgact tttaagggct catgagatta gattgtgtcc acctagataa  26100

tccaggatct cgatcgccat gggaattcgc atgcctcgag aaattcggcc cccggggccg  26160

cggccgc                                                            26167
```

<210> SEQ ID NO 2
<211> LENGTH: 6331
<212> TYPE: DNA
<213> ORGANISM: Bovine

<400> SEQUENCE: 2

```
gcggccgcgg ccccgggggc cgaattcttc aaagatcgtg ttctaataat ggataatttt     60

aaatgagtac ttattttatt tcagttcagt tcagtcactc agtcctgtct gactctttgc    120

gacaccatga accacagcaa gccaggcctc cctgtccatc accaactccc ggagtccacc    180

taaacccatg ttcatcgagt cgatgatgcc atccaaccat ctcatcctct gtcgtcccct    240

tcttctcctg ccctcagtct ttcccagcat cagggtcttt tccaatgagt caactcttcg    300

catcaggtag ccaaagtatt gtagtttcag cttcaacatc agtccttcca atgaacaccc    360

aggactgatc tgctttagga tagactggtt ggatctcctt gcagtccaag ggactctcaa    420

gagtcttctc caacaccaca gttcaaaagc atcaattctt cgtgctcagc cttctttata    480

gtccaactct cacatccata cgtgactact ggaaaaacca tagccttgac tagacggacc    540

tttcttgaca aagtaatgtc tctgcttttt aatatgctgt ctaggttggt cataactttc    600

cttacaagga gtaagcatct taattttatg gctgcaatca ccatctgcag tgaatttgga    660

gcccagaaaa attaagtcag ccactgtgtc cactgtttcc ccatctattt cccatgaagt    720

gatgggacca gatgccatga tcttagtttt ctgaatgttg agctttaagc caactttttc    780

actctcttct ttcactttcc tcaagaggct ctttagttct tcttcacttt ctgccataag    840

ggtggtacca tctgcatatc tgaggttatt gatatttctg ccagcaatct tgattccagc    900

ttgtgcttct tccagcccag cgtttctcat gatgtactct acatagaagt taaataagca    960

gggtgacaat atacagcctt gacgtactcc ttttcctatt tggaaccagt ctgttgttcc   1020

atgtccagtt ctaactgttg cttcctgacc tgcatacagt tttttcaaga ggcagggcag   1080

gtggcctggt attcccatct ctttcagaat tttccatagt ttattgtgat ccacacagtg   1140

aaaggttttg gcatagtcaa taaagcagaa atagatgttt ttctggaact cttttgcttt   1200

ttcgatgatc cagtgggtat tggcaatttg atctctggtt cctctgcctt ttctaaaacc   1260

agctggaaca tctggaggtt cacggttcac gtattgctga agcctttttt tttttttttt   1320

tttttaattt caggcactct tctaagtgtg tgaccttttc cctctcaacc acataggaag   1380

tggatattac taaacagatg ggaacattga gacaaaatga ggttgcaaaa ttacactgct   1440

ggtcattgaa agccagaaat taaacttaca atttgacctt gaagcattgt cttgcaacca   1500

ctacattcta tctctttact taaacaatgc tcacttaaga tttccaaaga ccaattgaca   1560

gagtatcaag ttaaaaagga cactgtttta aatccaaata taaaatctat cataggttcc   1620
```

-continued

```
acatttccag tactatcata tattcagaat ataaaacttc ctgaaaagag ctctgtttta   1680
gttctggata ctaaaattct atttatacaa tatctaagag taatcattaa tgatcttatt   1740
gtgtatcttt tcttagattc caaatggcat atggatttct agagaaaaac agaaatatct   1800
ttcacatttc tcagtaactt tccttctgga aggttgactg tttgttatat aattaagcaa   1860
cactttccta gaagactaat cagtcaaatg ttcctgggag aactttgaca aaccagtttg   1920
aaacttcaaa ttctgaattt ttcactgtct caaacaaagt cagtcctcca aagaggtttg   1980
aatctggact agaatattta gcaacaatgt acataatctt gcaggggata gtgtgtctct   2040
taactcatag ttttttttt caaaaatcta tgtttattac taataatgtt ttttgtatgt   2100
gtgctaattt ttctaataag tttaattttt ttttcattat tgaaatttga aagtcaagaa   2160
agcttagttc tcccttaccc agtctatttc tggtttcatt tctttaggga ttttgttgga   2220
ttttcaaaac aggttgtgat atcactagag tatctatgcc cttgagctct taaattagtc   2280
caatctatat ctattgtttt gttataatta ttaagagtag accctttac tatgataaat   2340
gatcaatgtt agatgaccaa ctttatggtc accccatgta tgactgttac atcagaaaat   2400
taatattttt atttatttac aaggcaaagg cccatttgac tacaaatagt ctaaatatgt   2460
gtctcaaatt taagccttgt ttagtagttg gaagtgaaga attttaagtg ataaagcaaa   2520
ttgaaaatat caatataaat caaataaatg taggctaaca ttttgcatga tttggcatta   2580
tataaatcta caatcctttt cacggatcac aaacttgttg tggtgaaggg ccttgagtaa   2640
ctcaatgaag ctatgagtca tgtcatacaa agctccccaa aatggtcaag tcatactgaa   2700
gagttctgac aaaatgtggt ccactggagg agggaatggc aaaccactgc aatattctta   2760
ccatgagaat cccatgaata gtatgaaaag gcaaaaagat acgacaccag aagatgagct   2820
ccccaagtca gaagatgtcc aatatgctac tagggaagag cagagggcag ttactaatag   2880
ctccagaaag gatggagcag gtgggccaaa gcagaaatga ctggttgtgt ctggtgataa   2940
aagtaaagtc caatgctgta aagaacagta ttgattagga acttagaatg ttaggttcat   3000
gaattaaggc aagttggata tggtcaagca ggaaagaaat cagtgaacta aaattggaca   3060
ggaatgggca atttaattca gattaccatt atatctatta ctgtgggcaa gaatccctta   3120
gaagaaatag agtagtcctc atagtcaaga aaagaatctg aaatgcagtg cttggatgca   3180
atctcaaaaa caatagaatg atctccattt gtttccaagg caaaccattc aacatcacag   3240
taatccaagt ctgtgcccca accactaacg ctgatgatgc tgaagatgac ctggtctaca   3300
aagacctaca agaccttcta gaactgacac cgaataaata aatcaatatc cttttcatca   3360
taggggattg gaatgcaaaa gtagaaagtc aagaaatact tggagtaaca ggaaattttg   3420
ctttggagtt aaaaatgaag caagtcaaag gctaacagtt gtgtcaagag aacacattgg   3480
tcatagtgaa taccctcttc caccaacacg agatgactct gtacatggac atcagcagat   3540
gatcaacact gaaattggat agattatatt ctttgcagcc aaagatggag agactgtata   3600
tagtcagtaa aaaataagac ctggagctga ctgtggctaa gatcttgagc tccttattgc   3660
aaaattcagg cttaaaaaga aaatgaagaa accattgaat ggacattgaa aattgaatgg   3720
acattcacta tgacctaatc aaatccctta tgattataca gtagaggtga tgaatagatt   3780
caaaggatta gatctggcta ttacattgta caggaggcag tgaccaacac tattccaaag   3840
tgggggtggg cggaaatcca gaagttaaag tggttatctg agaaggcttt acaaatagtt   3900
gagaaaagaa gaaagaaaat agaaaaagaa aagaaaagaa agagaagcaa aagacaaaga   3960
caaaggagaa aggggaagct atacccaact gaatgcagag ttccagaaaa tagcaagaga   4020
```

-continued

```
gaatgagaag gccttcttaa atgaacaatg caaagaagta gaggaaaaca atagaatgag   4080
aaagactaga gatctcttca agaaaactac agctgtcgtg ggaatatttc acaagggaat   4140
atttcccact tcccaagacc ttccaccagg gatcttccca acccagatgg gcatgaaaaa   4200
ggagagaaat aaaaaggact taacagaagc agaagaaatt aagaagaggt ggcaagaata   4260
gtattacaga agaactgtat ttaaaagatc ttaatgaccc agatagccac agttgtgtag   4320
tctctcatct acagcttaaa actcaatgtt caaaaaacta agttcatagc atactgcccc   4380
atcacttcat ggaaaatagt gggggagggg gagaaggtgg aagtagtgtc agattttatt   4440
ttcttggact caaaatcact gcagacagtg attatagcca tgaaattaaa tgacgcttac   4500
tccttgaaaa gaaagttctg aaaaacctag acaacatatt aaaaagcagt gacatcactt   4560
tactgataag tgtctttata gtcaaagcta tggtttttcc agtagccatg tacagatgtg   4620
agaattggac tatgaagaag gatgagtgtc aaaggactga tgttttcaaa ttgtggtgga   4680
tacactcctt tgcatgcgtg ctaagtcatt tcagtcatgt ccaactcttt gcaacccagt   4740
ggactgtcgt ctgccaggtt cctctgtcca tgggattctc caggcaagag caacggagtg   4800
ggttgtcatt tcctccacca ggggatcttc ccaatccaga tattgaacct gcatctctaa   4860
tgtttcctgc attggcaggc aggttcttta ccactagtgc cacctggaaa gtccggatac   4920
actcctggga aagacaaaag tagagtatta caatgcagca aggatttttg ttctcagctc   4980
cttgaataaa ttatagtgaa tagaaaacat tagtatcttg ttgaaattga tgtgaaacag   5040
atagtaagga agataatatc taaagaaaac ttcaatatgg gaaattatag tcttttctat   5100
cttcaaagtg gacagcctga acagttttga aatttctttt aatacaaaat aatgttcctg   5160
tcatacaact gtgaatacac tgaaaatatc actatagatt ttttaaagta tataatatga   5220
ttcctttctt ataaacaatg agttgcaatc aacaagtttt taaagctctc acttgtatag   5280
atttattttt agcacataat atttttctac aatgtacaat gccagttaat tctaggagta   5340
caattaagaa ttggagagat aggaattttt ttcttttact tgtttacttt aaaagatgga   5400
aaatcagagt tatggtttat ttttcgcaat atttaaaaat tataattctt gaataactat   5460
taattttaat taaataatct gtaatgagaa tcctcctacc aatgtaggag acgtgagttt   5520
gactcccggg tagggaagat accctgcaga aggaaatggc aacccactcc aatattatta   5580
cttgggaaat cccatggaca gaggagactg gcaggctgca gtccatgggg gtcacaaaga   5640
actggacacg acttagaaac taaacaacaa caatttatac cagaatgaat gaactagtta   5700
ccacaactag tacacccaaa atgaacaaaa aatagcttgg tggtataatt aaaatgccac   5760
caaaatttat acaataatta tattttcttt ttgcaggaaa aagattagac cacatataat   5820
gtaacttatt tcacaaggta aataattata ataaataata tggattaact gagttttaaa   5880
aggtgaaata aataatgaat tcttctcatg gtcttgtatg ttaataaaaa ttgaaaaatt   5940
ttgaagaccc cattttgtcc caagaatttc atttacaggt attgaatttt tcaaaggtta   6000
caaaggaaat tttattgata taataaatgc atgttctcat aataaccata aatctagggt   6060
tttgttgggg tttttttgtt tgttaattta gaacaatgcc attccatttc ctgtataatg   6120
agtcacttct ttgttgtaaa ctctccttag aatttcttgg gagaggaact gaacagaaca   6180
ttgatttcct atgtgagaga attcttagaa tttaaataaa cctgttggtt aaactgaaac   6240
cacaaaatta gcattttact aatcagtagg tttaaatagc ttggaagcaa aagtctgcca   6300
tcaccttgat catcaaccca tcgataggcc t                                  6331
```

-continued

```
<210> SEQ ID NO 3
<211> LENGTH: 6
<212> TYPE: PRT
<213> ORGANISM: Homo sapiens

<400> SEQUENCE: 3

Ala His Pro Gly Arg Pro
  1               5


<210> SEQ ID NO 4
<211> LENGTH: 36
<212> TYPE: DNA
<213> ORGANISM: Artificial Sequence:ClaI EcoRI site
<220> FEATURE:
<223> OTHER INFORMATION: Description of Artificial Sequence:
      illustrative DNA construct

<400> SEQUENCE: 4

ctcgagtatc gattgaattc atctgtcgac gctacc                              36


<210> SEQ ID NO 5
<211> LENGTH: 18
<212> TYPE: DNA
<213> ORGANISM: Artificial Sequence:SphI Xho/SalI* site
<220> FEATURE:
<223> OTHER INFORMATION: Description of Artificial Sequence:
      illustrative DNA construct

<400> SEQUENCE: 5

gcatgcctcg acggtacc                                                  18
```

HUMAN ACID ALPHA GLUCOSIDASE GENE AND BOVINE ALPHA-S1 CASEIN GENE SEQUENCES

CROSS-REFERENCE TO RELATED APPLICATIONS

This application claims the benefit of U.S. Provisional Application No. 60/122,550 filed Mar. 2, 1999, which is incorporated by reference in its entirety for all purposes and U.S. Provisional Application No. 60/110,850, filed Dec. 4, 1998. U.S. application Ser. No. 08/700,760, filed Jul. 29, 1996, now U.S. Pat. No. 6,118,045, Sep. 20, 2000, and U.S. application Ser. No. 60/001,796, filed Aug. 2, 1995 are directed to related subject matter and are incorporated by reference in their entirety for all purposes.

TECHNICAL FIELD

The present invention relates to polynuceotide sequences of the human acid alpha glucosidase gene and bovine alphaS1 casein promoter, and computerized storage and analysis of the same.

BACKGROUND

Like other secretory proteins, lysosomal proteins are synthesized in the endoplasmic reticulum and transported to the Golgi apparatus. However, unlike most other secretory proteins, the lysosomal proteins are not destined for secretion into extracellular fluids but into an intracellular organelle. Within the Golgi, lysosomal proteins undergo special processing to equip them to reach their intracellular destination. Almost all lysosomal proteins undergo a variety of posttranslational modifications, including glycosylation and phosphorylation via the 6' position of a terminal mannose group. The phosphorylated mannose residues are recognized by specific receptors on the inner surface of the Trans Golgi Network. The lysosomal proteins bind via these receptors, and are thereby separated from other secretory proteins. Subsequently, small transport vesicles containing the receptor-bound proteins are pinched off from the Trans Golgi Network and are targeted to their intracellular destination. See generally Kornfeld, Biochem. Soc. Trans. 18, 367–374 (1990).

There are over thirty lysosomal diseases, each resulting from a deficiency of a particular lysosomal protein, usually as a result of genetic mutation. See, e.g., Cotran et al., Robbins Pathologic Basis of Disease (4th ed. 1989) (incorporated by reference in its entirety for all purposes). The deficiency in the lysosomal protein usually results in harmful accumulation of a metabolite. For example, in Hurler's, Hunter's, Morquioes, and Sanfilippo's syndromes, there is an accumulation of mucopolysaccharides; in Tay-Sachs, Gaucher, Krabbe, Niemann-Pick, and Fabry syndromes, there is an accumulation of sphingolipids; and in fucosidosis and mannosidosis, there is an accumulation of fucose-containing sphingolipids and glycoprotein fragments, and of mannose-containing oligosaccharides, respectively.

Glycogen storage disease type II (GSD II; Pompe disease; acid maltase deficiency) is caused by deficiency of the lysosomal enzyme acid α-glucosidase (acid maltase). Three clinical forms are distinguished: infantile, juvenile and adult. Infantile GSD II has its onset shortly after birth and presents with progressive muscular weakness and cardiac failure. This clinical variant is fatal within the first two years of life. Symptoms in adult and juvenile patients occur later in life, and only skeletal muscles are involved. The patients eventually die due to respiratory insufficiency. Patients may exceptionally survive for more than six decades. There is a good correlation between the severity of the disease and the residual acid α-glucosidase activity, the activity being 10–20% of normal in late onset and less than 2% in early onset forms of the disease (see Hirschhorn, The Metabolic and Molecular Bases of Inherited Disease (Scriver et al., eds., 7th ed., McGraw-Hill, 1995), pp. 2443–2464).

Since the discovery of lysosomal enzyme deficiencies as the primary cause of lysosomal storage diseases (see, e.g, Hers, Biochem. J. 86, 11–16 (1963)), attempts have been made to treat patients having lysosomal storage diseases by (intravenous) administration of the missing enzyme, i.e., enzyme therapy. For lysosomal diseases other than Gaucher disease the evidence suggests that enzyme therapy is most effective when the enzyme being administered is phosphorylated at the 6' position of a mannose side chain group. For glycogenesis type II this has been tested by intravenously administering purified acid α-glucosidase in phosphorylated and unphosphorylated forms to mice and analyzing uptake in muscle tissue. The highest uptake was obtained when mannose 6-phosphate-containing enzyme was used (Van der Ploeg et al., Pediat. Res. 28, 344–347 (1990); . Clin. Invest. 87, 513–518 (1991)). The greater accumulation of the phosphorylated form of the enzyme can be explained by uptake being mediated by a mannose6-phosphate receptor present on the surface of muscle and other cells.

Some phosphorylated lysosomal enzymes can, in theory, be isolated from natural sources such as human urine and bovine testis. However, the production of sufficient quantities of enzyme for therapeutic administration is difficult. An alternative way to produce human acid α-glucosidase is to transfect the acid α-glucosidase gene into a stable eukaryotic cell line (e.g., CHO) as a cDNA or genomic construct operably linked to a suitable promoter.

Mammalian cellular expression systems are not entirely satisfactory for production of recombinant proteins because of the expense of propagation and maintenance of such cells. An alternative approach to production of recombinant proteins has been proposed by DeBoer et al., WO 91/08216, whereby recombinant proteins are produced in the milk of a transgenic animal. This approach avoids the expense of maintaining mammalian cell cultures and also simplifies purification of recombinant proteins.

Although the feasibility of expressing several recombinant proteins in the milk of transgenic animals has been demonstrated, it was unpredictable whether this technology could be extended to the expression of lysosomal proteins containing mannose 6-phosphate. Because typical secretory proteins like the milk proteins do not contain mannose groups phosphorylated at the 6' position, it was uncertain whether these cells possessed the necessary complement and activity of enzymes for phosphorylation of substantial amounts of an exogenous lysosomal protein. Further, if such cells did possess the necessary complement of enzymes, it would have appeared likely that phosphorylation would target the phosphorylated lysosomal protein via the mannose 6-phosphate receptor to an intracellular location rather than to an extracellular location. Substantial intracellular accumulation of a lysosomal protein might have been expected to have harmful or fatal consequences to the mammary gland function of the transgenic animal. Notwithstanding the above uncertainties and difficulties, the invention provides inter alia healthy transgenic mammals secreting in their milk active human alpha glucosidase in a form that can be taken up by a cells of a recipient patient. The invention also provides human alpha glucosidase and bovines alpha S1 casein genomic sequences useful for constructing transgenes for obtaining such expression.

SUMMARY OF THE INVENTION

In one aspect, the invention provides an isolated polynucleotide comprising at least 20 bases from a sequence shown in Table I or II (SEQ ID NO: 2) or the complement thereof Some such polynucleotides comprise at least 100 base from an intronic sequence shown in Table I or the complement thereof Some such polynucleotides include a regulatory region, such as an enhancer. Some such polynucleotides are a probe or primer of 20–100 bases. Some such polynucleotides comprise an intronic sequence shown in Table I free of exonic sequences.

The invention further provides an isolated promoter fragment from the alpha-glucosidase polynucleotide shown in Table I, which may be shorter than than 100 bases, optionally shorter than 50 bases. The invention further provides an isolated promoter fragment from the bovine alphaS 1 casein sequence shown in Table II, which likewise may be shorter than 100 bases, optionally shorter than 50 bases.

The invention further provides a computer program product for analyzing a polynucleotide sequence shown in Table I or II. The product comprises (a) code for storing a polynucleotide sequence; (b) code for analyzing the polynucleotide sequence; and (c) a computer readable storage medium for holding the codes.

The invention further provides a system for analyzing a polynucleotide sequence shown in Table I or II, comprising: (a) a memory; (b) a system bus; (c) a processor operatively disposed to: (1) provide a polynucleotide sequence; (2) analyze the polynucleotide sequence; (3) output results of the analysis.

In one aspect, the invention provides transgenic nonhuman mammals producing a lysosomal protein in their milk. The lysosomal protein is phosphorylated at the 6' position of a mannose side chain residue, The transgenic mammals have a transgene in their genome. The transgene comprises a mammary-gland specific promoter, a mammary-gland specific enhancer, a secretory DNA segment encoding a signal peptide functional in mammary secretory cells of the transgenic nonhuman mammal, and a recombinant DNA segment encoding a lysosomal protein, usually an enzyme. The recombinant DNA segment is operably linked to the secretory DNA segment to form a secretory-recombinant DNA segment. The secretory-recombinant DNA segment is in turn operably linked to the promoter and to the enhancer. The transgene, in an adult form of the nonhuman mammal or a female descendant of the nonhuman mammal, is capable of expressing the secretory-recombinant DNA segment in the mammary secretory cells to produce a form of the lysosomal protein that is processed and secreted by the mammary secretory cells into milk as a mannose 6-phosphate containing lysosomal protein. The concentration of the mannose 6-phosphate containing lysosomal protein in the milk is usually at least 100 $\mu$g/ml.

One useful enzyme expressed by such animals is acid α-glucosidase. Preferred animals for use in the invention include mice, rabbits, goats, sheep, porcines or bovines. The recombinant DNA segment can be cDNA, genomic or a hybrid of the two. In some transgenes, the secretory DNA segment is from the lysosomal protein gene encoded by the recombinant DNA segment.

In another aspect, the invention provides methods for producing a mannose 6-phosphate containing lysosomal protein in the milk of a transgenic mammal.

The methods entails recovering milk from the adult form of the transgenic nonhuman mammals described above. Optionally, the mannose 6-phosphate containing protein can be purified from the milk. The purified protein can then be mixed with a pharmaceutical carrier for intravenous, intradermal, intramuscular or oral administration.

In another aspect, the invention provides milk from the transgenic nonhuman mammals described above comprising the mannose 6-phosphate containing lysosomal protein.

DEFINITIONS

Figure 1:
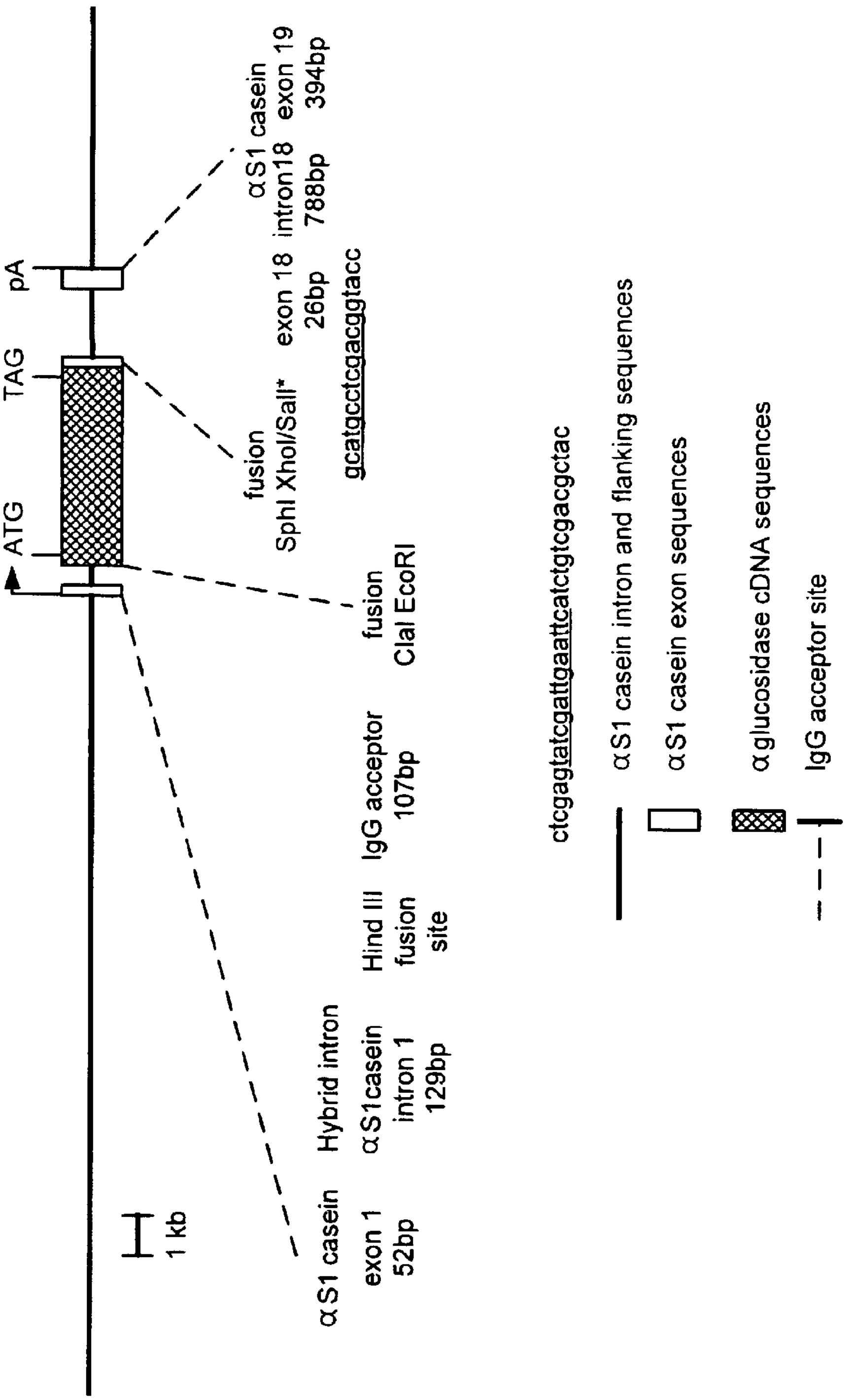
FIG. 1: A transgene containing acid α-glucosidase cDNA. The αs1-casein exons are represented by open boxes; α-glucosidase cDNA is represented by a shaded box. The αs1-casein intron and flanking sequences are represented by a thick line. A thin line represents the IgG acceptor site. The transcription initiation site is marked (□□), the translation initiation site (ATG), the stopcodon (TAG) and the polyadenylation site (pA) ClaI-EcoRI site (SEQ ID NO: 4); SphI-XhoI/SalI*(SEQ ID NO: 5).

The term "substantial identity" or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions which are not identical differ by conservative amino acid substitutions.

The term "substantially pure" or "isolated" means an object species has been identified and separated and/or recovered from a component of its natural environment. Usually, the object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition. Most preferably, the object species is purified to essential homogeneity (contaminant species cannot be detected in the composition by conventional detection methods) wherein the composition consists essentially of derivatives of a single macromolecular species.

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

An exogenous DNA segment is one foreign to the cell, or homologous to a DNA segment of the cell but in an unnatural position in the host cell genome. Exogenous DNA segments are expressed to yield exogenous polypeptides.

In a transgenic mammal, all, or substantially all, of the germline and somatic cells contain a transgene introduced into the mammal or an ancestor of the mammal at an early embryonic stage.

An oligonucleotide can be DNA or RNA, and single- or double-stranded. Oligonucleotides can be naturally occurring or synthetic, but are typically prepared by synthetic means. Preferred oligonucleotides of the invention include segments of DNA, or their complements including any one of the polymorphic sites shown in Table 1. The segments are usually between 5 and 100 bases, and often between 5–10, 5–20, 10–20, 10–50, 15–50, 15–100, 20–50 or 20–100 bases. The polymorphic site can occur within any position of the segment. The segments can be from any of the allelic forms of DNA shown in Table 1.

Hybridization probes are oligonucleotides capable of binding in a base-specific manner to a complementary strand of nucleic acid. Such probes include peptide nucleic acids, as described in Nielsen et al., Science 254, 1497–1500 (1991).

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 59 upstream primer that hybridizes with the 5' end of the DNA sequence to be amplified and a 3', downstream primer that hybridizes with the complement of the 3' end of the sequence to be amplified.

An isolated nucleic acid means an object species invention that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

DETAILED DESCRIPTION

The invention provides transgenic nonhuman mammals secreting a mannose 6-phosphate containing lysosomal protein into their milk. Secretion is achieved by incorporation of a transgene encoding a lysosomal protein and regulatory sequences capable of targeting expression of the gene to the mammary gland. The transgene is expressed, and the expression product posttranslationally modified within the mammary gland, and then secreted in milk. The posttranslational modification includes steps of glycosylation and phosphorylation.

A. Lysosomal Genes

The invention provides transgenic nonhuman mammals expressing DNA segments containing any of the more than 30 known genes encoding lysosomal enzymes and other types of lysosomal proteins, including α-glucosidase, α-L-iduronidase, iduronate-sulfate sulfatase, hexosarninidase A and B, ganglioside activator protein, arylsulfatase A and B, iduronate sulfatase, heparan N-sulfatase, galacto-ceramidase, α-galactosylceramidase A, sphingomyelinase, α-fucosidase, α-mannosidase, aspartylglycosamine amide hydrolase, acid lipase, N-acetyl-α-D-glucosanine-6-sulphate sulfatase, α-and β-galactosidase, β-glucuronidase, β-mannosidase, ceramidase, galactocere-brosidase, α-N-acetylgalactosaminidase, and protective protein and others. Transgenic mammals expressing allelic, cognate and induced variants of any of the known lysosomal protein gene sequences are also included. Such variants usually show substantial sequence identity at the amino acid level with known lysosomal protein genes. Such variants usually hybridize to a known gene under stringent conditions or crossreact with antibodies to a polypeptide encoded by one of the known genes.

DNA clones containing the genomic or cDNA sequences of many of the known genes encoding lysosomal proteins are available. (Scott et al., Am. J. Hum. Genet. 47, 802–807 (1990); Wilson et al., PNAS 87, 8531–8535 (1990); Stein et al., J. Biol. Chem. 264, 1252–1259 (1989); Ginns et al., Biochem. Biophys. Res. Comn. 123, 574–580 (1984); Hoefsloot et al., EMBO J. 7, 1697–1704 (1988); Hoefsloot et al., Biochem. J. 272, 473–479 (1990); Meyerowitz & Proia, PNAS 81, 5394–5398 (1984); Scriver et al., supra, part 12, pages 2427–2882 and references cited therein)) Other examples of genomic and cDNA sequences are available from GenBank. To the extent that additional cloned sequences of lysosomal genes are required, they may be obtained from genomic or cDNA libraries (preferably human) using known lysosomal protein DNA sequences or antibodies to known lysosomal proteins as probes.

B. Conformation of Lysosomal Proteins

Recombinant lysosomal proteins are preferably processed to have the same or similar structure as naturally occurring lysosomal proteins. Lysosomal proteins are glycoproteins that are synthesized on ribosomes bound to the endoplasmic reticulum (RER). They enter this organelle co-translationally guided by an N-terminal signal peptide (Ng et al., Current Opinion in Cell Biology 6, 510–516 (1994)). The N-linked glycosylation process starts in the RER with the en bloc transfer of the high-mannose oligosaccharide precursor Glc3Man9GlcNAc2 from a dolichol carrier. Carbohydrate chain modification starts in the RER and continue in the Golgi apparatus with the removal of the three outermost glucose residues by glycosidases I and II. Phosphorylation is a two-step procedure in which first N-acetyl-gluco-samine-1-phosphate is coupled to select mannose groups by a lysosomal protein specific transferase, and second, the N-acetyl-gluco-samine is cleaved by a diesterase (Goldberg et al., Lysosomes: Their Role in Protein Breakdown (Academic Press Inc., London, 1987), pp. 163–191).

Cleavage exposes mannose 6-phosphate as a recognition marker and ligand for the mannose 6-phosphate receptor mediating transport of most lysosomal proteins to the lysosomes (Kornfeld, Biochem. Soc. Trans. 18, 367–374 (1992)).

In addition to carbohydrate chain modification, most lysosomal proteins undergo proteolytic processing, in which the first event is removal of the signal peptide. The signal peptide of most lysosomal proteins is cleaved after translocation by signal peptidase after which the proteins become soluble. There is suggestive evidence that the signal peptide of acid α-glucosidase is cleaved after the enzyme has left the RER, but before it has entered the lysosome or the secretory pathway (Wisselaar et al., J. Biol. Chem. 268, 2223–2231 (1993)). The proteolytic processing of acid α-glucosidase is complex and involves a series of steps in addition to cleavage of the signal peptide taking place at various subcellular locations. Polypeptides are cleaved off at both the N and C terminal ends, whereby the specific catalytic activity is increased. The main species recognized are a 110/100 kDa precursor, a 95 kDa intermediate and 76 kDa and 70 kDa mature forms. (Hasilik et al., J. Biol. Chem. 255, 49374945 (1980); Oude Elferink et al., Eur. J. Biochem. 139, 489–495 (1984); Reuser et al., J. Biol. Chem. 260, 8336–8341 (1985); Hoefsloot et al., EMBO J. 7, 1697–1704 (1988)). The post translational processing of natural human acid α-glucosidase and of recombinant forms of human acid α-glucosidase as expressed in cultured mammalian cells like COS cells, BHK cells and CHO cells is similar (Hoefsloot et al., (1990) supra; Wisselaar et al., (1993) supra.

Authentic processing to generate lysosomal proteins phosphorylated at the 6' position of the mannose group can be tested by measuring uptake of a substrate by cells bearing a receptor for mannose 6-phosphate. Correctly modified substrates are taken up faster than unmodified substrates, and in a manner whereby uptake of the modified substrate can be competitively inhibited by addition of mannose 6-phosphate.

C. Transgene Design

Transgenes are designed to target expression of a recombinant lysosomal protein to the mammary gland of a transgenic nonhuman mammal harboring the transgene. The basic approach entails operably linking an exogenous DNA segment encoding the protein with a signal sequence, a promoter and an enhancer. The DNA segment can be genomic, minigene (genomic with one or more introns omitted), cDNA, a YAC fragment, a chimera of two different lysosomal protein genes, or a hybrid of any of these. Inclusion of genomic sequences generally leads to higher levels of expression. Very high levels of expression might overload the capacity of the mammary gland to perform posttranslation modifications, and secretion of lysosomal proteins. However, the data presented below indicate that substantial posttranslational modification occurs including the formation of mannose 6-phosphate groups, notwithstanding a high expression level in the mg/ml range. Thus, genomic constructs or hybrid cDNA-genomic constructs are generally preferred.

In genomic constructs, it is not necessary to retain all intronic sequences. For example, some intronic sequences can be removed to obtain a smaller transgene facilitating DNA manipulations and subsequent microinjection. See Archibald et al., WO 90/05188 (incorporated by reference in its entirety for all purposes). Removal of some introns is also useful in some instances to reduce expression levels and thereby ensure that posttranslational modification is substantially complete. It is also possible to delete some or all of noncoding exons. In some transgenes, selected nucleotides in lysosomal protein encoding sequences are mutated to remove proteolytic cleavage sites.

Because the intended use of lysosomal proteins produced by transgenic mammals is usually administration to humans, the species from which the DNA segment encoding a lysosomal protein sequence is obtained is preferably human. Analogously if the intended use were in veterinary therapy (e.g., on a horse, dog or cat), it is preferable that the DNA segment be from the same species.

The promoter and enhancer are from a gene that is exclusively or at least preferentially expressed in the mammary gland (i.e., a mammary-gland specific gene). Preferred genes as a source of promoter and enhancer include β-casein, κ-casein, αS1-casein, αS2-casein, β-lactoglobulin, whey acid protein, and α-lactalbumin. The promoter and enhancer are usually but not always obtained from the same mammary-gland specific gene. This gene is sometimes but not necessarily from the same species of mammal as the mammal into which the transgene is to be expressed. Expression regulation sequences from other species such as those from human genes can also be used. The signal sequence must be capable of directing the secretion of the lysosomal protein from the mammary gland. Suitable signal sequences can be derived from mammalian genes encoding a secreted protein. Surprisingly, the natural signal sequences of lysosomal proteins are suitable, notwithstanding that these proteins are normally not secreted but targeted to an intracellular organelle. In addition to such signal sequences, preferred sources of signal sequences are the signal sequence from the same gene as the promoter and enhancer are obtained. Optionally, additional regulatory sequences are included in the transgene to optimize expression levels. Such sequences include 5' flanking regions, 5' transcribed but untranslated regions, intronic sequences, 3' transcribed but untranslated regions, polyadenylation sites, and 3' flanking regions. Such sequences are usually obtained either from the mammary-gland specific gene from which the promoter and enhancer are obtained or from the lysosomal protein gene being expressed. Inclusion of such sequences produces a genetic milieu simulating that of an authentic mammary gland specific gene and/or that of an authentic lysosomal protein gene. This genetic milieu results in some cases (e.g., bovine αS1-casein) in higher expression of the transcribed gene. Alternatively, 3' flanking regions and untranslated regions are obtained from other heterologous genes such as the β-globin gene or viral genes. The inclusion of 3' and 5' untranslated regions from a lysosomal protein gene, or other heterologous gene can also increase the stability of the transcript.

In some embodiments, about 0.5, 1, 5, 10, 15, 20 or 30 kb of 5' flanking sequence is included from a mammary specific gene in combination with about 1, 5, 10, 15, 20 or 30 kb or 3' flanking sequence from the lysosomal protein gene being expressed. If the protein is expressed from a cDNA sequence, it is advantageous to include an intronic sequence between the promoter and the coding sequence. The intronic sequence is preferably a hybrid sequence formed from a 5' portion from an intervening sequence from the first intron of the mammary gland specific region from which the promoter is obtained and a 3' portion from an intervening sequence of an IgG intervening sequence or lysosomal protein gene. See DeBoer et al., WO 91/08216 (incorporated by reference in its entirety for all purposes).

A preferred transgene for expressing a lysosomal protein comprises a cDNA-genomic hybrid lysosomal protein gene linked 5' to a casein promoter and enhancer. The hybrid gene includes the signal sequence, coding region, and a 3' flanking region from the lysosomal protein gene. Optionally, the cDNA segment includes an intronic sequence between the 5' casein and untranslated region of the gene encoding the lysosomal protein. Of course, corresponding cDNA and genomic segments can also be fused at other locations within the gene provided a contiguous protein can be expressed from the resulting fusion.

Other preferred transgenes have a genomic lysosomal protein segment linked 5' to casein regulatory sequences. The genomic segment is usually contiguous from the 5' untranslated region to the 3' flanking region of the gene. Thus, the genomic segment includes a portion of the lysosomal protein 5' untranslated sequence, the signal sequence, alternating introns and coding exons, a 3' untranslated region, and a 3' flanking region. The genomic segment is linked via the 5' untranslated region to a casein fragment comprising a promoter and enhancer and usually a 5' untranslated region.

DNA sequence information is available for all of the mammary gland specific genes listed above, in at least one, and often several organisms. See, e.g., Richards et al., J. Biol. Chem. 256, 526–532 (1981) (α-lactalbumin rat); Campbell et al., Nucleic Acids Res. 12, 8685–8697 (1984) (rat WAP); Jones et al., J. Biol. Chem. 260, 7042–7050 (1985)) (rat β-casein); Yu-Lee & Rosen, J. Biol. Chem. 258, 10794–10804 (1983) (rat γ-casein)); Hall, Biochem. J. 242, 735–742 (1987) (α-lactalbumin human); Stewart, Nucleic Acids Res. 12, 389 (1984) (bovine αs1 and κ casein cDNAs); Gorodetsky et al., Gene 66, 87–96 (1988) (bovine β casein); Alexander et al., Eur. J. Biochem. 178, 395–401 (1988) (bovine κ casein); Brignon et al., FEBS Lett. 188, 48–55 (1977) (bovine αS2 casein); Jamieson et al., Gene 61, 85–90 (1987), Ivanov et al., Biol. Chem. Hoppe-Seyler 369, 425–429 (1988), Alexander et al., Nucleic Acids Res. 17, 6739 (1989) (bovine β lactoglobulin); Vilotte et al., Biochimie 69, 609–620 (1987) (bovine α-lactalbumin) (incorporated by reference in their entirety for all purposes). The structure and function of the various milk protein genes are reviewed by Mercier & Vilotte, J. Dairy Sci. 76, 3079–3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

General strategies and exemplary transgenes employing αS1-casein regulatory sequences for targeting the expression of a recombinant protein to the mammary gland are described in more detail in DeBoer et al., WO 91/08216 and WO 93/25567 (incorporated by reference in their entirety for all purposes). Examples of transgenes employing regulatory sequences from other mammary gland specific genes have also been described. See, e.g., Simon et al., Bio/Technology 6, 179–183 (1988) and WO88/00239 (1988) (β-lactoglobulin regulatory sequence for expression in sheep); Rosen, EP 279,582 and Lee et al., Nucleic Acids Res. 16, 1027–1041 (1988) (β-casein regulatory sequence for expression in mice); Gordon, Biotechnology 5, 1183 (1987) (WAP regulatory sequence for expression in mice); WO 88/01648 (1988) and Eur. J. Biochem. 186, 43–48 (1989) (α-lactalbumin regulatory sequence for expression in mice) (incorporated by reference in their entirety for all purposes).

The expression of lysosomal proteins in the milk from transgenes can be influenced by co-expression or functional inactivation (i.e., knock-out) of genes involved in post translational modification and targeting of the lysosomal proteins. The data in the Examples indicate that surprisingly mammary glands already express modifying enzymes at sufficient quantities to obtain high level assembly and secretion of human acid alpha glucosidase in appropriate form for catalytic activity and uptake in a recipient patient. However, in some transgenic mammals expressing these proteins at high levels, it is sometimes preferable to supplement endogenous levels of processing enzymes with additional enzyme resulting from transgene expression. Such transgenes are constructed employing similar principles to those discussed above with the processing enzyme coding sequence replacing the lysosomal protein coding sequence in the transgene. It is not generally necessary that posttranslational processing enzymes be secreted. Thus, the secretion signal sequence linked to the lysosomal protein coding sequence is replaced with a signal sequence that targets the processing enzyme to the endoplasmic reticulum without secretion. For example, the signal sequences naturally associated with these enzymes are suitable.

D. Transgenesis

The transgenes described above are introduced into nonhuman mammals. Most nonhuman mammals, including rodents such as mice and rats, rabbits, ovines such as sheep and goats, porcines such as pigs, and bovines such as cattle and buffalo, are suitable. Bovines offer an advantage of large yields of milk, whereas mice offer advantages of ease of transgenesis and breeding. Rabbits offer a compromise of these advantages. A rabbit can yield 100 ml milk per day with a protein content of about 14% (see Buhler et al., Bio/Technology 8, 140 (1990)) (incorporated by reference in its entirety for all purposes), and yet can be manipulated and bred using the same principles and with similar facility as mice. Nonviviparous mammals such as a spiny anteater or duckbill platypus are typically not employed.

In some methods of transgenesis, transgenes are introduced into the pronuclei of fertilized oocytes. For some animals, such as mice and rabbits, fertilization is performed in vivo and fertilized ova are surgically removed. In other animals, particularly bovines, it is preferable to remove ova from live or slaughterhouse animals and fertilize the ova in vitro. See DeBoer et al., WO 91/08216. In vitro fertilization permits a transgene to be introduced into substantially synchronous cells at an optimal phase of the cell cycle for integration (not later than S-phase). Transgenes are usually introduced by microinjection. See U.S. Pat. No. 4,873,292. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. Methods for culturing fertilized oocytes to the pre-implantation stage are described by Gordon et al., Methods Enzymol. 101, 414 (1984); Hogan et al., Manipulation of the Mouse Embryo: A Laboratory Manual, C.S.H.L. N.Y. (1986) (mouse embryo); and Hammer et al., Nature 315, 680 (1985) (rabbit and porcine embryos); Gandolfi et al. J. Reprod. Fert. 81, 23–28 (1987); Rexroad et al., J. Anim. Sci. 66, 947–953 (1988) (ovine embryos) and Eyestone et al. J. Reprod. Fert. 85, 715–720 (1989); Camous et al., J. Reprod. Fert. 72, 779–785 (1984); and Heyman et al. Theriogenology 27, 5968 (1987) (bovine embryos) (incorporated by reference in their entirety for all purposes). Sometimes pre-implantation embryos are stored frozen for a period pending implantation. Pre-implantation embryos are transferred to the oviduct of a pseudopregnant female resulting in the birth of a transgenic or chimeric animal depending upon the stage of development when the transgene is integrated. Chimeric mammals can be bred to form true germline transgenic animals.

Alternatively, transgenes can be introduced into embryonic stem cells (ES). These cells are obtained from preimplantation embryos cultured in vitro. Bradley et al., Nature 309, 255–258 (1984) (incorporated by reference in its entirety for all purposes). Transgenes can be introduced into such cells by electroporation or microinjection. Transformed ES cells are combined with blastocysts from a non-human, animal. The ES cells colonize the embryo and in some embryos form the germline of the resulting chimeric animal. See Jaenisch, Science, 240, 1468–1474 (1988) (incorporated by reference in its entirety for all purposes). Alternatively, ES cells can be used as a source of nuclei for transplantation into an enucleated fertilized oocyte giving rise to a transgenic mammal.

For production of transgenic animals containing two or more transgenes, the transgenes can be introduced simultaneously using the same procedure as for a single transgene. Alternatively, the transgenes can be initially introduced into separate animals and then combined into the same genome by breeding the animals. Alternatively, a first transgenic animal is produced containing one of the transgenes. A second transgene is then introduced into fertilized ova or embryonic stem cells from that animal. In some embodiments, transgenes whose length would otherwise exceed about 50 kb, are constructed as overlapping fragments. Such overlapping fragments are introduced into a fertilized oocyte or embryonic stem cell simultaneously and undergo homologous recombination in vivo. See Kay et al., WO 92/03917 (incorporated by reference in its entirety for all purposes).

E. Characteristics of Transgenic Mammals

Transgenic mammals of the invention incorporate at least one transgene in their genome as described above. The transgene targets expression of a DNA segment encoding a lysosomal protein at least predominantly to the mammary gland. Surprisingly, the mammary glands are capable of expressing proteins required for authentic posttranslation processing including steps of oligosaccharide addition and phosphorylation. Processing by enzymes in the mammary gland can result in phosphorylation of the 6' position of mannose groups.

Lysosomal proteins can be secreted at high levels of at least 10, 50, 100, 500, 1000, 2000, 5000 or 10,000 $\mu$g/ml. Surprisingly, the transgenic mammals of the invention exhibit substantially normal health. Secondary expression of lysosomal proteins in tissues other than the mammary gland does not occur to an extent sufficient to cause deleterious effects. Moreover, exogenous lysosomal protein produced in the mammary gland is secreted with sufficient efficiency that no significant problem is presented by deposits clogging the secretory apparatus.

The age at which transgenic mammals can begin producing milk, of course, varies with the nature of the animal. For transgenic bovines, the age is about two-and-a-half years naturally or six months with hormonal stimulation, whereas for transgenic mice the age is about 5–6 weeks. Of course, only the female members of a species are useful for producing milk. However, transgenic males are also of value for breeding female descendants. The sperm from transgenic males can be stored frozen for subsequent in vitro fertilization and generation of female offspring.

F. Recovery of Proteins from Milk

Transgenic adult female mammals produce milk containing high concentrations of exogenous lysosomal protein. The protein can be purified from milk, if desired, by virtue of its distinguishing physical and chemical properties, and standard purification procedures such as precipitation, ion exchange, molecular exclusion or affinity chromatography. See generally Scopes, Protein Purification (Springer-Verlag, N.Y., 1982)

G. Uses of Recombinant Lysosomal Proteins

The recombinant lysosomal proteins produced according to the invention find use in enzyme replacement therapeutic procedures. A patient having a genetic or other deficiency resulting in an insufficiency of functional lysosomal enzyme can be treated by administering exogenous enzyme to the patient. Patients in need of such treatment can be identified from symptoms (e.g., Hurler's syndrome symptoms include Dwarfism, corneal clouding, hepatosplenomegaly, valvular lesions, coronary artery lesions, skeletal deformities, joint stiffness and progressive mental retardation). Alternatively, or additionally, patients can be diagnosed from biochemical analysis of a tissue sample to reveal excessive accumulation of a characteristic metabolite processed by a particular lysosomal enzyme or by enzyme assay using an artificial or natural substrate to reveal deficiency of a particular lysosomal enzyme activity. For most diseases, diagnosis can be made by measuring the particular enzyme deficiency or by DNA analysis before occurrence of symptoms or excessive accumulation of metabolites (Scriver et al., supra, chapters on lysosomal storage disorders). All of the lysosomal storage diseases are hereditary. Thus, in offspring from families known to have members suffering from lysosomal diseases, it is sometimes advisable to commence prophylactic treatment even before a definitive diagnosis can be made.

In some methods, lysosomal enzymes are administered in purified form together with a pharmaceutical carrier as a pharmaceutical composition. The preferred form depends on the intended mode of administration and therapeutic application. The pharmaceutical carrier can be any compatible, nontoxic substance suitable to deliver the polypeptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions.

The concentration of the enzyme in the pharmaceutical composition can vary widely, i.e., from less than about 0.1% by weight, usually being at least about 1% by weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

A typical composition for intravenous infusion could be made up to contain 100 to 500 ml of sterile 0.9% NaCl or 5% glucose optionally supplemented with a 20% albumin solution and 100 to 500 mg of a enzyme. A typical pharmaceutical compositions for intramuscular injection would be made up to contain, for example, 1 ml of sterile buffered water and 1 to 10 mg of the purified ligand of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

The pharmaceutical compositions of the present invention are usually administered intravenously. Intradermal, intramuscular or oral administration is also possible in some circumstances. The compositions can be administered for prophylactic treatment of individuals suffering from, or at risk of, a lysosomal enzyme deficiency disease. For therapeutic applications, the pharmaceutical compositions are administered to a patient suffering from established disease in an amount sufficient to reduce the concentration of accumulated metabolite and/or prevent or arrest further accumulation of metabolite. For individuals at risk of lysosomal enzyme deficiency disease, the pharmaceutical composition are administered prophylactically in an amount sufficient to either prevent or inhibit accumulation of metabolite. An amount adequate to accomplish this is defined as a "therapeutically-" or "prophylactically-effective dose." Such effective dosages will depend on the severity of the condition and on the general state of the patient's health, but will generally range from about 0.1 to 10 mg of purified enzyme per kilogram of body weight.

Lysosomal proteins produced in the milk of transgenic animals have a number of other uses. For example, α-glucosidase, in common with other α-amylases, is an important tool in production of starch, beer and pharmaceuticals. See Vihinen & Mantsala, Crit. Rev. Biochem. Mol. Biol. 24, 329–401 (1989) (incorporated by reference in its entirety for all purpose). Lysosomal proteins are also useful for producing laboratory chemicals or food products. For example, acid α-glucosidase degrades 1,4 and 1,6 α-glucosidic bounds and can be used for the degradation of various carbohydrates containing these bonds, such as maltose, isomaltose, starch and glycogen, to yield glucose. Acid α-glucosidase is also useful for administration to patients with an intestinal maltase or isomaltase deficiency. Symptoms otherwise resulting from the presence of undigested maltose are avoided. In such applications, the enzyme can be administered without prior fractionation from milk, as a food product derived from such milk (e.g., ice cream or cheese) or as a pharmaceutical composition. Purified recombinant lysosomal enzymes are also useful for inclusion as controls in diagnostic kits for assay of unknown quantities of such enzymes in tissue samples.

1. Sequences of Alpha-glucosidase Gene and Bovine AlphaS1 Casein Promoter

The invention further provides complete sequences for the human acid alpha glucosidase gene (SEQ ID NO:1) and for the bovine alpha S1 casein promoter (SEQ ID NO:2). These sequences are useful for construction of transgenes in which the alpha-glucosidase coding sequence is operably linked to the bovine αS1 casein promoter. Optionally, such transgenes can contain intronic sequences, flanking sequence, or UTR sequences from the alpha-glucosidase gene. Alternatively, a transgene can be constructed including the human alpha glucosidase sequence operably linked to its own promoter. For example, such a transgene can include the entire alpha glucosidase sequence shown below or that sequence lacking the first 53 bases of exon 1. The casein promoter fragment shown can also be used to direct expression of other protein sequences.

The complete genomic sequence of the human alpha glucosidase gene is shown below in Table I (SEQ ID NO:1). The numbering starts arbitrarily at 5503. Bases 5503 to 6278 comprise the genomic α-glucosidase promoter sequence. Bases 6279 to 31599 are the genomic alpha-glucosidase sequence including 6947 bases flanking the AATTAAA poly A signal at the 3' The translationsal start codon (underlined) occurs at bases 9383–9385. The translational stop codon occurs at bases 24144–24146. The poly A signal occupies bases 24674–24679 and the 3' flanking sequence occupies bases 24697–31611.

Bases 31612–31661 are part of a vector polylinker containing restriction sites. A terminal NotI site occupies bases 31662–31669. Exons are indicated in bold; exon and intron lengths are indicated on the right as are homologies to Alu repeat sequences (italics). Alu repeats occur between bases 8783–9043, 11442–11718, 18532–18810, 25762–25886 (half-repeat), 25887–26177, 26187–26336 (half repeat), 26347–26634, 27502–27822, 28177–28466, and 30151–30426. The underlined region 25012–25042 was only sequenced on the upper (CT-rich) strand. The first 53 bp of sequence from exon 1 are omitted in some trangenes for expression of alpha glucosidase.

TABLE I

```
5503   gagacgga gtctcgctct gtcgcccagg ctggagtgca gtggcgcggt ctcggctcgc  48

      tgcaagctgg aaagggggct tttaatgccc ctatgcccct acccaggaac aacacctctg

      tgttttggtg tggctccttt tgtatttttc tgcacataca ttttattagg caagttaagg

      ttatactgtg tgttttttgt atctcacatg taaaaatgtg ctcctcttaa tgtaagcatt

      ttctcatttt atgaaaaaat tccccctgtg tcagtttaat gttttctcaa ttgtcagttt
```

TABLE I-continued

| | | |
|---|---|---|
| 5801 | tatgggttat cacaatgttt tgattattcc tttctggaat aactgtgagt tatggagcac | |
| | acttaaggac tttccaaatg ttggctgttt ctaacttggc gctgagcgcc tttggccgcc | |
| | tttccgatga tgccctcggg acgcgttggc aggaggaatc cctgggcgca aggcgcggct | |
| | gggccagccc cttacaaagc cctacgagct gcggggaccc aggccggggc agcgggggcc | |
| | acgccccatc tccgacccca cggggaccgg gccgggactg cgccagcggg ggcctcgccc | |
| 6101 | cgtctctgac cccagaggaa ccggcagcgg gcagcacgcg tgggcctctc cccgcgggac | |
| | gccggacgcg cagccagacg cgctccccag gccccctccg agagcgagga cgcgcccagg | |
| | cccgctctgc cggagccgcc actgggggc gtagcgcgga cgcgcaccct tgcctcgg**GC** | |
| | **GCCTGCGCGG GAGGCCGCGT CACGTGACcC ACCGCGGCCC cGCCccGCGL CGLGCTCCCG** | |
| | **CCGGTCACGT GACCCGCCTC TGCGCGCCCC CGGGCACGAC CCCGGLGTCT CCGCGGGCGG** | |
| 6401 | **CCAGGGCGCG CGTGCGCGGA GGTGAGCCGG GCCGGGGCTG CGGGGCTTCC CTGLGCGCGG** | |
| | **GCCGGGTCGG TGGGGCGGTC GGCTGCCCGC GCGGCCTCTC AGTTGGGAAA GCTGAGGTTG** | **exon 1** |
| | **TCGCCGGGGC CGCGGGTGGA GGTCGGGGAT GAGGCAGCAG GTAGGACAGT GACCTCGGTG** | **408 bp** |
| | **ACGCGAAGGA CCCCGGCCAC CTCTAGGTTC TCCTCGTCCG CCCGTTGTTC AGCGAGGGAG** | |
| | **GCTCTGCGCG TGCCGCAGCT GACGGGGAAA CTGAGGCACG GAGCGGgtga** gacacctgac | |
| 6701 | gtctgccccg cgctgccggc ggtaacatcc cagaagcggg tttgaacgtg cctagccgtg | |
| | cccccagcct cttcccctga gcggagcttg agccccagac ctctagtcct cccggtcttt | |
| | atctgagttc agcttagaga tgaacgggga gccgccctcc tgtgctgggc ttggggctgg | |
| | aggctgcatc ttcccgtttc tagggtttcc tttcccctttt tgatcgacgc agtgctcagt | intron 1 |
| | cctggccggg acccgagcca cctctcctgc tcctgcagga cgcacatggc tgggtctgaa | |
| 7001 | tccctggggt gaggagcacc gtggcctgag agggggcccc tgggccagct ctgaaatctg | |
| | aatgtctcaa tcacaaagac cccccttaggc caggccaggg gtgactgtct ctggtctttg | |
| | tccctggttg ctggcacata gcacccgaaa cccttggaaa ccgagtgatg agagagcctt | |
| | ttgctcatga ggtgactgat gaccggggac accaggtggc ttcaggatgg aagcagatgg | |
| | ccagaaagac caaggcctga tgacgggttg ggatggaaaa ggggtgaggg gctggagatt | |
| 7301 | gagtgaatca ccagtggctt agtcaaccat gcctgcacaa tggaaccccg taagaaacca | |
| | cagggatcag agggcttccc gccgggttgt ggaacacacc aaggcactgg agggtggtgc | |
| | gagcagagag cacagcatca ctgcccccac ctcacaccag gccctacgca tctcttccat | |
| | acggctgtct gagttttatc ctttgtaata aaccagcaac tgtaagaaac gcactttcct | |
| | gagttctgtg accctgaaga gggagtcctg ggaacctctg aatttataac tagttgatcg | |
| 7601 | aaagtacaag tgacaacctg ggatttgcca ttggcctctg aagtgaaggc agtgttgtgg | |
| | gactgagccc ttaacctgtg gagtctgtgc tgactccagg tagtgtcaag attgaattga | |
| | attgtaggac acccagccgt gtccagaaag ttgcagaatt gatgggtgtg agaaaaaccc | |
| | tacacattta atgtcagaag tgtgggtaaa atgtttcacc ctccagccca gagagcccta | |
| | atttaccagt ggcccacggt ggaacaccac gtccggccgg gggcagagcg ttcccagcca | |
| 7901 | agccttctgt aacatgacat gacaggtcag actccctcgg gccctgagtt cacttcttcc | |
| | tggtatgtga ccagctccca gtaccagaga aggttgcaca gtcctctgct ccaaggagct | |
| | tcactggcca ggggctgctt tctgaaatcc ttgcctgcct ctgctccaag gcccgttcct | |
| | cagagacgca gacccctctg atggctgact ttggtttgag gacctctctg catccctccc | |

TABLE I-continued

| | | |
|---|---|---|
| | ccatggcctt gctcctagga caccttcttc ctcctttccc tggggtcaga cttgcctagg | |
| 8201 | tgcggtggct ctcccagcct tccccacgcc ctccccatgg tgtattacac acaccaaagg | |
| | gactccccta ttgaaatcca tgcatattga atcgcatgtg ggttccggct gctcctggga | |
| | ggagccaggc taatagaatg tttgccataa aatattaatg tacagagaag cgaaacaaag | |
| | gtcgttggta cttgttaacc ttaccagcag aataatgaaa gcgaaccccc atatctcatc | |
| | tgcacgcgac atccttgttg tgtctgtacc cgaggctcca ggtgcagcca ctgttacaga | intron 1 |
| 8501 | gactgtgttt cttccccatg tacctcgggg gccgggaggg gttctgatct gcaaagtcgc | 2664 bp |
| | cagaggttaa gtcctttctc tcttgtggct ttgccacccc tggagtgtca ccctcagctg | |
| | cggtgcccag gattccccac tgtggtatgt ccgtgcacca gtcaatagga aagggagcaa | |
| | ggaaaggtac tgggtccccc taaggacata cgagttgcca gaatcacttc cgctgacacc | |
| | cagtggacca agccgcacct ttatgcagaa gtggggctcc ca*gccaggcg tggtcactcc* | |
| 8801 | *tgaaatccca gcacttcgga aggccaaggg gggtggatca cttgagctca ggagttcgag* | |
| | *accagcctgg gtaacatggc aaaatcccgt ctctacaaaa atacagaaaa ttagctgggt* | *Alu repeat* |
| | *gcggtggtgt gtgcctacag tcccagctac tcaggaggct gaagtgggag gattgcttga* | *(261 bp)* |
| | *gtctgggagg tggaggttgc agtgagccag gatctcacca cagcactctg gcccaggcga* | |
| | *cagc*tgtttg gcctgtttca agtgtctacc tgccttgctg gtcttcctgg ggacattcta | |
| 9101 | agcgtgtttg atttgtaaca ttttagcaga ctgtgcaagt gctctgcact cccctgctgg | |
| | agcttttctc gcccttcctt ctggccctct ccccagtcta gacagcaggg caacacccac | |
| | cctggccacc ttaccccacc tgcctgggtg ctgcagtgcc agccgcggtt gatgtctcag | |
| | agctgctttg agagccccgt gagtgccgcc cctcccgcct ccctgctgag cccgctttct | |
| | tctcccgcag **GCCTGTAGGA GCTGTCCAGG CCATCTCCAA CCATGGGAGT GAGGCACCCG** | **start** |
| 9401 | **CCCTGCTCCC ACCGGCTCCT GGCCGTCTGC GCCCTCGTGT CCTTGGCAAC CGCTGCACTC** | |
| | **CTGGGGCACA TCCTACTCCA TGATTTCCTG CTGGTTCCCC GAGAGCTGAG TGGCTCCTCC** | |
| | **CCAGTCCTGG AGGAGACTCA CCCAGCTCAC CAGCAGGGAG CCAGCAGACC AGGGCCCCGG** | **exon 2** |
| | **GATGCCCAGG CACACCCCGG CCGTCCCAGA GCAGTGCCCA CACAGTGCGA CGTCCCCCCC** | **578 bp** |
| | **AACAGCCGCT TCGATTGCGC CCCTGACAAG GCCATCACCC AGGAACAGTG CGAGGCCCGC** | |
| 9701 | **GGCTGTTGCT ACATCCCTGC AAAGCAGGGG CTGCAGGGAG CCCAGATGGG GCAGCCCTGG** | |
| | **TGCTTCTTCC CACCCAGCTA CCCCAGCTAC AAGCTGGAGA ACCTGAGCTC CTCTGAAATG** | |
| | **GGCTACACGG CCACCCTGAC CCGTACCACC CCCACCTTCT TCCCCAAGGA CATCCTGACC** | |
| | **CTGCGGCTGG ACGTGATGAT GGAGACTGAG AACCGCCTCC ACTTCACG**gt gggcagggca | |
| | ggggcggggg cggcggccag ggcagagggt gcgcgtggac atcgacaccc acgcacctca | |
| 10001 | caagggtggg gtgcatgttg caccactgtg tgctgggccc ttgctgggag cggaggtgtg | |
| | agcagacaat ggcagcgccc ctcgggggagc agtggggaca ccacggtgac aggtactcca | |
| | gaaggcaggg ctcggggctc attcatcttt atgaaaaggt gggtcaggta gagtagggct | intron 2 |
| | gccagaggtt gcgaatgaaa acaggatgcc cagtaaaccc gaattgcaga taccccaggc | 616 bp |
| | atgactttgt ttttttgtgt aaggatgcaa aatttgggat gtatttatac tagaaaagct | |
| 10301 | gcttgttgtt tatctgaaat tcagagttat caggtgttct gtattttacc tccatcctgg | |
| | gggaggcgtc ctcctcctgg ctctgcagat gagggagccg aggctcagag aggctgaatg | |
| | tgctgcccat ggtcccacat ccatgtgtgg ctgcaccagg acctgacctg tccttggcgt | |
| | gcgggttgtt ctctggagag taaggtggct gtggggaaca tcaataaacc cccatctctt | |

TABLE I-continued

| | | |
|---|---|---|
| | ctag**ATCAAA GATCCAGCTA ACAGGCGCTA CGAGGTGCCC TTGGAGACCC CGCATGTCCA** | **exon 3** |
| 10601 | **CAGCCGGGCA CCGTCCCCAC TCTACAGCGT GGAGTTCTCC GAGGAGCCCT TCGGGGTGAT** | **146 bp** |
| | **CGTGCGCCGG CAGCTGGACG GCCGCGTGCT** gtgagttctg ggctctgtgc cagcatgatg | |
| | gggagggcga cgcgcatttc tcacacggca gggagggcca cacgcgtttg tttctcacac | |
| | gatgggcagg gcgacacatg tttgtttctc acacggcggg gagggcgacg ggcatttctc | |
| | acagggcgct ccctgggtct tttactcaca taggtctaaa tcccatgtaa acacgtgttc | |
| 10901 | aggactcacc aagcccctgc ttgtcattta actcaggaaa actctcagga acgacagcac | |
| | ttggatttgc cttaatctta agagaagttg ccttcggaaa tgcgtttttc tttttttgct | |
| | cattcattta ctcagtgtcc acgcactgac cctccgtgcc gggtggtttg gatcctgctc | |
| | ccggggacag acacacagtg aggggaagcc ataagcaagt ccatgcagac acagcgtcag | |
| | ggagtggtca tgcagagagc acgctagaag ccagctgtgc agacacgggg cagggaggtc | intron 3 |
| 11201 | ccctctagaa gccagctgtg cagacgcagg ggacagggat ggcctctctg gaagccagct | |
| | gtgcagatgt tgggggcagg ggtggcctct ctggaagcca gctgtgcagg agtggggggt | 1662 bp |
| | ggggaggcca ctctggaaac cagctgtgca gatgcagggg acaggggtgg cctctctgag | |
| | ctgacctctg agtagagaga cccaagagaa gtttctcaaa gcatcttatc aagctaggta | |
| | *tggtggttca tgtctgcaat tccagcactt tgggaggcca aggcgagagg gtcacttgag* | |
| 11501 | *cccaggagtt caagaccatc ctgggcaaca tagcaagacc ccatctctta aaaaataaaa* | *Alu repeat* |
| | *ataaaaaatt agctgggaat tgtggcacat gcctgtggtc gcagctactc aggaggctga* | *(277 bp)* |
| | *ggcaagagga tcccttgagc ccaggggttc gaggttgcag tgaaccatga ttttgccact* | |
| | *gcacttcagc cttgctgaag accccgtctc aaaaaacaaa* caacaaacag gcatcttatc | |
| | agatctcggt cttgaaagca ctcagcgcag tcttgcccag gggagggtgg gtgtggtgtg | |
| 11901 | agcccgtcct gcgaaattag ctgtgctgtg ttaacagagg acgcgtcttc ctgtggaccg | |
| | gatttatctg cggctttcat ttctcggagg tgctgtttgc cttgcacttg atccccagaa | |
| | aacctcaggg gtccttctgg ggcatggctg ggctgggatc tgggaggact ttggccacaa | |
| | gctcctaggc ctggaaaggt tctgttcagc ccctgcccag ccttgcttgg ggtcatggga | |
| | caggcatgtg tgccagttcc ggtaccagcc agttcctgga ggtcagcccc ttgggggccc | |
| 12101 | ctcaggggtg gtgtgggccc agccaggcgg tgcgcccctt ctgatatgcc ctgagagttg | |
| | atcacgctgg tgccagggtg ccaagggctg cagggctcgg cacggccgcc tgtcccaggg | |
| | tcagtgtgct gcagggctgg ccaggccact ccgccctccc agggcaccag ggcccggggg | |
| | tgctctctgg gtgctctcag gctcgtgtgg ccccttgggt gtgagcaagc ctggctggcc | |
| | tctgtcccgc ag**GCTGAACA CGACGGTGGC GCCCCTGTTC TTTGCGGACC AGTTCCTTCA** | **exon 4** |
| 12401 | **GCTGTCCACC TCGCTGCCCT CGCAGTATAT CACAGGCCTC GCCGAGCACC TCAGTCCCCT** | **146 bp** |
| | **GATGCTCAGC ACCAGCTGGA CCAGGATCAC CCTGTGGAAC CGGGACCTTG** CGCCCACGgt | intron 4 |
| | acagcagcgg gcggcgggcg gcgggcgggg gcaccgagct ggggagcgca ggtgctgaag | 84 bp |
| | cgccgtctcc tgcatgtccc agCCC**GGTGC GAACCTCTAC GGGTCTCACC CTTTCTACCT** | **exon 5** |
| | **GCCGCTGGAG GACGGCGGGT CGGCACACGG GGTGTTCCTG CTAAACAGCA ATGCCATGG**g | 97 bp |
| 12701 | taagctgccc accgcccagc gcccgggccg gggtctcctc cgtgctgcct gccctggaga | |
| | ctggaggtcc gcatgagggg ccctgggcac ggtgctgggc cttgtgtttt ctgggaaatg | |
| | agtcctatgg gctgatgcct ctcccaactc tggccttctg tgctcctaag gagggttctg | intron 5 |

TABLE I-continued

| | | |
|---|---|---|
| | gggccctgcc tggaggtggg ctggcaccac atatctttcc gtcccatgcc aggttcctcc | 353 bp |
| | tgagtcaggc ttagcacggc ttccccaggc cactctgagc tcctcatggg gagagagcct | |
| 13001 | caactctctg cctgtgattg gcccatctgt ggggtgcaga gccctccaag tgaagaatct | |
| | gtcccccaac cccagagctg cttcccttcc ag**ATGTGGTC CTGCAGCCGA GCCCTGCCCT** | **exon 6** |
| | **TAGCTGGAGG TCGAGAGGTG GGATCCTGGA TGTCTACATC TTCCTGGGCC CAGAGCCCAA** | **120 bp** |
| | **GAGCGTGGTG CAGCAGTACC TGGACGTTGT GG**gtagggcc tgctccctgg ccgcggcccc | intron 6 |
| | cgccccaagg ctccctcctc cctccctcat gaagtcggcg ttggcctgca **gGATACCCGT** | 79 bp |
| 13301 | **TCATGCCGCC ATACTGGGGC CTGGGCTTCC ACCTGTGCCG CTGGGGCTAC TCCTCCACCG** | **exon 7** |
| | **CTATCACCCG CCAGGTGGTG GAGAACATGA CCAGGGCCCA CTTCCCCCTG** gtgagttggg | **119 bp** |
| | gtggtggcag gggaggcaag gggctggccg ggacgcgtct cctcaggccc cagcagacgg | intron 7 |
| | tcccgtgttg tggctgcag**G ACGTCCAATG GAACGACCTG GACTACATGG ACTCCCGCAG** | 89 bp |
| | **GGACTTCACG TTCAACAAGG ATGGCTTCCG GGACTTCCCG GCCATGGTGC AGGAGCTGCA** | **exon 8** |
| 13601 | **CCAGGGCGGC CGGCGCTACA TGATGATCGT G**gtgtgtgcc cccacactgt gggtctttgg | **132 bp** |
| | gaagggggcc gcccggtgcc cagtggctcc ttctctgtgc agcgtcatcc tcgtgcctgt | |
| | gtggtcgccg aggatgtttt ctgagggtct ttgtgatatc gaaggaatat caagaagttt | |
| | gcaggcttgg ccccagctgt ccagggaggt cgggtttgag ggtccccaga aatggccggg | |
| | tgctactcag ggttctgtca gatgtaggtt acttgaactg ccttaaagca aaaggccagg | |
| 13901 | ggcatgataa actgatgtca cctggtcctg gaaagtggag ggcccggtgg gcctgggcat | intron |
| | gggtatcgct ggaactgtgg aggctccgtg tgccttctgg ccgtgcctct ccttctggcc | 1109 bp |
| | ggctctgaat ccctggaaag gacggcgtga gtgagggcag cttccagccc tcatgctggc | |
| | accacagagc ggagacttct tcccatcagc tcccatagaa aagtcccaaa gcaggactct | |
| | tgagtcaccc agcacaaaga ggcccttccc tgagccagtc ccacagccag aaggatgcag | |
| 14201 | tttgggggct ggtccagccc gagtctggtg tccggcacga tggccagagg aggaggtggg | |
| | aggcagggcg agctgaaaag atccaacagt tcctgcccgg aagatccact tcagcagagg | |
| | aagcacagat gagatgtggg gctgtgctga tgctgcctgt ttccatccct gccttctgca | |
| | ggcagcaaac attagtagcc cttaagagca ggagtggaaa cacagacttt ttctttctca | |
| | catttttta attataaaag aaaagtgatt actgtaggac acttgggaaa ctctagaggt | |
| 14501 | ttaaagaaaa ggtaaagctt ccattccggc gcgcccctca tcagccagct ggtcctgact | |
| | cgcccggccc tggctcctct ccaggcaggc gtgtgcaggc atgtgcaggt acacaggcag | |
| | gcgtgctgta cacacgcatg atgtcatccc cagcctcatc ctctcactgt ctcagttttc | |
| | cccgtggctg gcgccagggc tctgggccac cctcaccttg acgggtttcc ctcttcccag | |
| | **GATCCTGCCA TCAGCAGCTC GGGCCCTGCC GGGAGCTACA GGCCCTACGA CGAGGGTCTG** | **exon 9** |
| 14801 | **CGGAGGGGGG TTTTCATCAC CAACGAGACC GGCCAGCCGC TGATTGGGAA G**gtagggcga | **111 bp** |
| | gggtccaggg gacgggggtt agaaagcaga ggcctccagc caggggggagc cggcagctgc | |
| | tcaggaagac ggtgggattt gaggagccat cacgcccagt gggacagctg agaggaatgg | |
| | gccacagtgg cccgtgacga tggtggctcc tacaaggaat ggccccgtga gttcttccat | |
| | cagcaggcct ttgacttcat gggcagctgg gcctggccca ggcacaagcc ctgcagaccc | |
| 15101 | tcagtgaggc cttagggtcc tccttgtcct cccagccccc caggggcctc caggcagggc | intron 9 |
| | ccccgctgag ggagcagcta gggagggtct ggtgcggatg tgaggctgcc tggcagggct | 671 bp |
| | tgcacggggc cgtctccgct gcccttctcc ctgacgctct ctggttctgc agcccagccc | |

TABLE I-continued

| | | |
|---|---|---|
| | ctgggtggac gtgttggggg tggcccctcg ttttcccagg gttgaggccc cttggccccg | |
| | catcagtgcc ttgtggagaa agagctgctc attgacctcc agggtgcagg tctctcagat | |
| 15401 | ttgcaaatgt gggcatccac taagagtgag gctgcccctc tgctcaggct gaggctcagt | |
| | ggggcttcca tgcaggccct gggtggggcc gggtctcccc actccagcct ctcgttgtcc | |
| | **agGTATGGCC CGGGTCCACT GCCTTCCCCG ACTTCACCAA CCCCACAGCC CTGGCCTGGT** | **exon 10** |
| | **GGGAGGACAT GGTGGCTGAG TTCCATGACC AGGTGCCCTT CGACGGCATG TGGATT**gtaa | **114 bp** |
| | gtgtggcccc ctcctgagca tccccaaggc ctctggggac taccacaccc tcctcactct | intron 10 |
| 15701 | gggcagagtc acctaccagc agcgcttctc ttgcag**GACA TGAACGAGCC TTCCAACTTC** | 100 bp |
| | **ATCAGGGGCT CTGAGGACGG CTGCCCCAAC AATGAGCTGG AGAACCCACC CTACGTGCCT** | **exon 11** |
| | Ggtcagctcg ccccccacct accctgggga cttaatcaaa tcagagactc ccttgtctgg | **85 bp** |
| | cctgggagac ttagcaccct catctctgag aagcagatgg gccagcgggg aaaggggtgg | |
| | ggggggatcc ccaggagaaa ggctcaggct gggagactca gccaagcagt gcagacaggg | |
| 16001 | tgggtgcaga ggcacaggcc ctgccggagg agacgccgct cacaggtgct tgccagagca | |
| | cagtgaggcc gactcgactc agagccgtct cgataggcgc agggaccatg cagcggagac | |
| | ctacccaccc gtggggagag gtcaggccca actcgaatgc agcacgggca agtggatttc | |
| | tagccaggga gcagggtggg ctcagaggtg ggaattacca agaggaagca tgggggtcag | intron 11 |
| | ggggattctg gctgaactga cccagcagga ttcttgctga aggcaggcca gggtgaccag | 956 bp |
| 16301 | acatcgcctg aggggtggtg gaggttgggg cttctcgcca aactgtctta gcaggaatgg | |
| | cagaaactgg gttttacaag gaagtacaag gatgggcctg ggagaaggtt tgggggcctg | |
| | aggctatagt ttggcccagc aaagaatcag tgagaggatg gggttttggg cttaggtaaa | |
| | caggcagggg agtgcttgaa atgggccaag agacggtgga tgtgaagtct gggggtctgc | |
| | agagcccagg ctccagcacc cgcccagccc tgtcttagaa gcagtggaga tgattaccca | |
| 16601 | ggttcccggg taacgccagc cccacagagg cgtggggagc ggctgcaggt gcacctccag | |
| | ggccagcctg aagaggcagc gacctgcaca ggggctcctg ggaggtgggg ggcagggagg | |
| | gcaccttgga gcctgccggg aggaagctcc ctggaaacca gcccccgcct cttccag**GGG** | |
| | **TGGTTGGGGG GACCCTCCAG GCGGCCACCA TCTGTGCCTC CAGCCACCAG TTTCTCTCCA** | **exon 12** |
| | **CACACTACAA CCTCCACAAC CTCTACGGCC TGACCGAAGC CATCGCCTCC CACAG**gtgag | **118 bp** |
| 16901 | ggccacatcc cgccccactg ggctctgccc tcacagcctg tcctacaagg ttggggcctc | |
| | tgcagggcct cagggaggag gaaaagcgga ggcccagacc acccggggcc cgctggcggc | |
| | ccgagtgctc tccccacctg ctgcctgcac cccagcctga agctggagcg ctccttccca | intron 12 |
| | cttcatgcct ggggcttgga gaggaaggac cctggatgct gacaggagtc tgcatcagcg | 477 bp |
| | gggacctcat gactcctgtg aggctggggg gggtcctggc tcacctacag gcatcaggtg | |
| 17201 | gcccagacag aggcaactgt gcccgcagac atgggcagta gcctcgccgt cctcctcccc | |
| | agcctctgcc tcatcccaga aagctccttg ctcccagctc tgccctgctg gtgacagggt | |
| | tcccgagtga ccccgctcca cacagccctc acggtgtccc ccaccacccc ag**GGCGCTGG** | |
| | **TGAAGGCTCG GGGGACACGC CCATTTGTGA TCTCCCGCTC GACCTTTGCT GGCCACGGCC** | **exon 13** |
| | **GATACGCCGG CCACTGGACG GGGGACGTGT GGAGCTCCTG GGAGCAGCTC GCCTCCTCCG** | **134 bp** |
| 17501 | **TGCCAG**gtga gctcctacca ggagggggctg ctcagcagag tagagccggg ggcctctatg | intron 13 |
| | ggaggcttgc cggggccccc cacccactta gcaggtgggg ctctgggtca cttggcctga | 160 bp |

TABLE I-continued

| | | |
|---|---|---|
| | gctggctctg ctgcagcagc ctgaggacca gcctgactct gccctcccag **AAATCCTGCA** | |
| | **GTTTAACCTG CTGGGGGTGC CTCTGGTCGG GGCCGACGTC TGCGGCTTCC TGGGCAACAC** | **exon 14** |
| | **CTCAGAGGAG CTGTGTGTGC GCTGGACCCA GCTGGGGGCC TTCTACCCCT TCATGCGGAA** | **152 bp** |
| 17801 | **CCACAACAGC CTGCTCAGTC TG**gtagggtg ggggtggcgg cgtggcaggt gggcgatccc | |
| | acccacccaa gactctcccc tgggaattcc gcccctgctg gagaagcacc ccatgctggg | intron 14 |
| | tggctgagaa gtgcagctct cccgaggcag ggactccagg ggaccgcggc cccagcaccc | 190 bp |
| | aagtgcttcc tttgcccccg cctgccctgc ag**CCCCAGGA GCCGTACAGC TTCAGCGAGC** | |
| | **CGGCCCAGCA GGCCATGAGG AAGGCCCTCA CCCTGCGCTA CGCACTCCTC CCCCACCTCT** | **exon 15** |
| 18101 | **ACACACTGTT CCACCAGGCC CACGTCGCGG GGGAGACCGT GGCCCGGCCC CTCTTCCTGG** | **149 bp** |
| | **A**gtgagtgac ctaggcaggg gcggtggccc atgtgtgccc tgggggaggg gcacgtaact | |
| | cccaggcagc cctgtcctgc tgtgggctgt gttccccagg acccagcagg ttgccgctga | |
| | gtgagacaac atttgggcct ggcttaaggg ggaagggcag caagaaaacc cagtaatatc | |
| | ccccagacag gccgtagtac acacgaggag ttcctaacaa cagccctgca catcagtgtg | |
| 18401 | ttgagggagg attcccagag agtaaggtga ttagttaact atttgcagaa gtcaatttat | |
| | ttttcttgca taccatagaa acataagttc cagataaatt aaatagttaa tgtcaaaaat | |
| | caagctgtgg *aggccaggca cggtggctaa cgcccgtaat cccagaactt tgggaggctg* | |
| | *aggcgagtgg atcacctgag gtcaagagtt cgaggccagc ctggccaaca tggtgaaacc* | *Alu repeat* |
| | *catctctact aaaaatacaa aaattagccg tgcatggtgg tgggcgcctg tagtccctgc* | |
| 18701 | *tactcaggag gctgaggcca gagaatccct tgaacctggg aggaggagat tgcagtgagc* | |
| | *cgagatcacg ccactgtact ccagcctgtg tgactccatc tcaaaaaaaa* aaaccaagct | |
| | gtgaaagact ccacaggaaa agataagtga atgtgtatct ctggggaaag gtttcattta | |
| | gagaaaaaaa aaaaaaaaag gtgaacttta tttgaccata gcagaaaaaa aaatgtaaat | |
| | ctctgaatat aaacacaaaa agattaaaac tgctctgaac atggactgta acagcagaga | |
| 19001 | aggcattgtc aataaaacag caaatagcta ctcttcctaa taggtagaga actcatacgt | |
| | tggtaagacc aagactaaga accaaattgg aggaacactg tttgcaaaac aggagatacg | |
| | aatggtatcc acacattctt cacccggaaa tccaagaaac gcaatttgtg ttttaattac | |
| | tattttaatg accttgttgt ttctgtcact acactttttt tttttttttt agtggttgcc | intron 15 |
| | ctagggatta caattaacat cttaatttta gcctcgttgg aactgatgcc aacttgcttt | 3598 bp |
| 19301 | caatagcata aaaaagcttt gcttctatgt ggtttccatt gcctctcgtt cctctgtgct | |
| | gttacacgtc tgtatccatg atgagcccat ccacgcagat ttataatgac cgccttattc | |
| | aattatcttt taagtcaaat aggagggaaa aatgggttac aaacaaaaag tacatacaca | |
| | ctgtctgcct tttatattta ctgatgtagt tacctttacc catggtttta tttcttcatg | |
| | tggctttgac ttcttgtcta acatctttca tttacagcag aaggactccc tttagtattt | |
| 19601 | attgtagggc agttctgcta gtgatgaatt ctctcagttt ttgttgactt cagagtctct | |
| | taatttctcc ttcatttttt gaaagttctg ctcaacgtag ggttcttgac tggcggtcgt | |
| | ttctctgaac actttgaact tgtcagccca tggcctccgt ggtttctgct gagtagcttc | |
| | tgtcttgcct cttcccagat tctctgtctt tggcctttga agtcccgatg gtgtgtctag | |
| | gtgtagatct ctgagtttat cttactggga gtttgttgag cttcttggac gtatgcattg | |
| 19901 | atgtttttca tcaaacttgg gcggtttttc agccattact tcataaaata ttttttctgc | |
| | ccctttctgt cttctactct gggacttccg ttccacacat tggtatgctt gacggtgccc | |

TABLE I-continued

| | | | | | | | |
|---|---|---|---|---|---|---|---|
| | aggggtcttt | gcagctctgt | tgactccttc | ctcgttgtgt | tttctttctg | ttcttcagac | |
| | tgcttagtct | gactgccctg | tcttcaaggt | cactgattct | tttttccacc | agttctcatc | |
| | tgctgttgag | cccctctagt | gaacttctca | ttttagttgc | tctcttttca | actccagaat | |
| 20201 | ttctgtttca | ttcctttacg | tttctctcgt | taaggatatt | ccctatctgg | tgagtcatgt | |
| | tctcacactt | tcctttagtt | cttcagacac | ggtttcgctg | agctctttga | acacatttaa | |
| | agtagctgac | gtaaactctt | tgtctagtaa | gtccaatgtc | tgggcttctc | tagggacaat | |
| | ttttattaac | tactgtcccc | ccatctgtgg | gccatacttt | cttgtttctt | tgcgtgtctc | |
| | atacattttt | gtttcagact | ggacatttta | aacgcagctg | ctgtggtcat | cagattcccc | |
| 20501 | atccccctca | ggtctcgttg | ctattgctga | ttgttttgtg | actttcttga | gctaattcca | |
| | taaggtctgt | gttcttcatt | gtgtgtggcc | accaaagtct | ctgcttgact | agcttagtgg | |
| | acagccaata | attggtcaga | tatccttcac | agatggcatc | cgtgagtctc | ccagcctttg | |
| | ctggggcgag | gtggggagca | ccgtcaacac | ttagctaggc | caaggattct | tgctgttctt | |
| | acaaagattc | agccattttg | ttaaatacat | gctccccaga | tggctgcaaa | cccttggtta | |
| 20801 | gtttcaagag | tcctaaaaat | gtcaactctg | accattttg | ccgatgttcc | tgttttcaca | |
| | gaggagagga | tcttgagagg | ggcttactcc | accatcttca | ctgacatcac | tccaagaaat | |
| | gtattttgca | agaaatattt | tgaagcagaa | agacaccatt | tattttgccc | atgaattaga | |
| | atacattaga | gaaaataaga | ctatcccttg | ctggcaagaa | cacagtgaca | cagtagggtg | |
| | gaatataaat | tggcacattt | gtggaaagca | acagtacata | tcagtcaatg | tttttgagat | |
| 21101 | tcacattgat | gcattaattt | tacaaataga | aatagggcct | aaagaagtca | cctcaaaagg | |
| | catgaacgct | ccatgaatgt | atccatgcag | ggatcatagc | tgagcactgg | atgccccctg | |
| | cacatccggg | ggcaggaaac | aggacagggc | agagctgcgt | cacagggcag | gacagtctcc | |
| | gttagacgga | gaatcctccg | tagagctgct | tgcacgtgta | cattcatctt | tttgtcagat | |
| | gttaattcaa | gttgcctttg | gttgtgggac | tgggaggatc | ttttctcttt | gttgatactt | |
| 21401 | tttcgtactt | tccaaatact | tgactgatga | gcacatgctg | ccttggttac | cggaggataa | |
| | gtgagcgagc | aaagtgaggc | cagtgctgtg | tccatcctgg | tgcctcaagc | acaagcccct | |
| | attcctgccc | tgagcccagc | tgccggcatg | tccggggaga | aggcttctcc | cagctccggc | |
| | attgacttct | atctgctgga | atcatccctg | cccgtctgac | ctgagtcctc | caagtcctcc | |
| | ggcaccttga | gctccagaga | gcagaattca | gcctcttcct | gtgcctcccc | agggtgggca | |
| 21701 | tatgagccag | ccccatccca | ttcatcaccc | gtatgcctgt | gtgcccatcc | cccttgcag**G** | |
| | **TTCCCCAAGG** | **ACTCTAGCAC** | **CTGGACTGTG** | **GACCACCAGC** | **TCCTGTGGGG** | **GGAGGCCCTG** | **exon 16** |
| | **CTCATCACCC** | **CAGTGCTCCA** | **GGCCGGGAAG** | **GCCGAAGTGA** | **CTGGCTACTT** | **CCCCTTGGGC** | **142 bp** |
| | **ACATGGTACG** | **ACCTGCAGAC** | **G**gtgagtctg | gggaccctaa | accccgggga | gaccctaaac | |
| | cccggggaga | cgggagacca | gagcagccct | cccacctgcc | ccctccaccc | agttggtgtg | |
| 22001 | accaggtggc | ggaaagagga | acgtatgtgt | tgagtcccgg | ccatgtgcca | ggcccccacc | |
| | cggctgctcc | gcacccatca | gcctctccgc | tcctcacacc | atccccattt | cccagatgag | intron 16 |
| | cagactgagg | cctgcttgca | gaacctggcc | aagtcccacg | gccatcacag | gctgtgcctg | 508 bp |
| | tgctgagctg | gcatacccag | gcctctcagg | ctctgtcccc | actcagtagc | caggagggtc | |
| | cctacctaca | gtgagccctg | agtctgcgcc | tgaagtcaca | gttcagcccg | tctgtgccag | |
| 22301 | gcctcctagg | cctccacgtg | gagccccggg | agatggagag | cgtggttcct | gaggacagca | |

TABLE I-continued

| | | |
|---|---|---|
| | tggggggcctc ggcacggccc agaatcctca aagcaacatc tccctccagG TGCCAATAGA | |
| | GGCCCTTGGC AGCCTCCCAC CCCCACCTGC AGCTCCCCGT GAGCCAGCCA TCCACAGCGA | exon 17 |
| | GGGGCAGTGG GTGACGCTGC CGGCCCCCCT GGACACCATC AACGTCCACC TCCGGGCTGG | 150 bp |
| | GTACATCATC CCCCTGCAGg tacctgggcc aggcggctat ggtgggggtg tggacagcac | |
| 22601 | actgcagagc tgggggaggc acagggagat ggtgggggag aggcccaggt ggggcttctg | |
| | aggggccgcc ccccgcagtg taggttatca aggagccagc caggccagtg aggtggggag | intron 17 |
| | ggcacagccc cacaaaggcg tggagcatgg ccggcaggag ctcagtggtc tgcatggtgg | 447 bp |
| | aggttctgcc gggcccggcc tcgggcagcc gtgggatagc acttgaggtg gggaaggtct | |
| | tgggtcatca ccacggggtt ccagcccctg cggccggccg caggtgttcc tgcagatcct | |
| 22901 | agttactggc agcctggtgc tgtaccagcc tagcattccc gggccctgga ggcctccacc | |
| | tccaccaggg tggggatgat gacatcacgt gtccttccct ttccagGGCC CTGGCCTCAC | |
| | AACCACAGAG TCCCGCCAGC AGCCCATGGC CCTGGCTGTG GCCCTGACCA AGGGTGGGGA | exon 18 |
| | GGCCCGAGGG GAGCTGTTCT GGGACGATGG AGAGAGCCTG GAAGTGCTGG AGCGAGGGGC | 165 bp |
| | CTACACACAG GTCATCTTCC TGGCCAGGAA Tgtgagtcct ggggctgctc aggctggtgg | |
| 23201 | gcaggggccg gctcggggtt gagaaggggt gaggggacct gggcttgggg gtcccacgat | |
| | ggctacctgc cactaggaca ctctagcagg tggcctgggg tcctagagtg agcagtgggg | intron 18 |
| | ccgtgcactc tgccctttcg tgtacacaga gggaggtcac ctccctgatg ccatcatgag | 295 bp |
| | tccctgttct catgggtgtt cctgccccag ctgtctgctg acacctccac attctctgcc | |
| | ttttcatctc tctctgctcg gcccagAACA CGATCGTGAA TGAGCTGGTA CGTGTGACCA | exon 19 |
| 23501 | GTGAGGGAGC TGGCCTGCAG CTGCAGAAGG TGACTGTCCT GGGCGTGGCC ACGGCGCCCC | 153 bp |
| | AGCAGGTCCT CTCCAACGGT GTCCCTGTCT CCAACTTCAC CTACAGCCCC GACACCAAGg | |
| | caagagggcc cagagtggca cagggatcgc gtcccccagc cgtggtgcag ggggcagaag | |
| | gtgctgggcg tcctggtgac cgatgccagg aacagaggat gctgggacct cccaaggggg | |
| | tctttgggga ggagtgggaa gggtcaggcc acacaggctg tgcctttcct cctcctgtgt | intron 19 |
| 23801 | ctacacgtgg gtgatggggc cacaatgacg acctctgagc cgtgttgaag cagcaccgtg | 467 bp |
| | tttctggcgt gcgttaaggt gacccgcact gagagccggg gtccccctgc gcctgccggg | |
| | gaggaaccgg gtgcgaagca tcccagggcc agacggagct gcccccctgag cgccgggcct | |
| | cgctgctgct gggatctcgg ggccagatgg agccgccttc tgagcgctgg ggtctcactg | |
| | ctgctgggat ctcgggctgc tccatttgtg ctctctcttt ttccagGTCC TGGACATCTG | |
| 24101 | TGTCTCGCTG TTGATGGGAG AGCAGTTTCT CGTCAGCTGG TGTTAGCCGG GCGGAGTGTG | stopcodon |
| | TTAGTCTCTC CAGAGGGAGG CTGGTTCCCC AGGGAAGCAG AGCCTGTGTG CGGGCAGCAG | |
| | CTGTGTGCGG GCCTGGGGGT TGCATGTGTC ACCTGGAGCT GGGCACTAAC CATTCCAAGC | |
| | CGCCGGCATC GCTTGTTTCC ACCTCCTGGG CCGGGGCTCT GGCCCCCAAC GTGTCTAGGA | exon 20 |
| | GAGCTTTCTC CCTAGATCGC ACTGTGGGCC GGGGCCCTGG AGGGCTGCTC TGTGTTAATA | 610 bp |
| 24401 | AGATTGTAAG GTTTGCCCTC CTCACCTGTT GCCGGCATGC GGGTAGTATT AGCCACCCCC | |
| | CTCCATCTGT TCCCAGCACC GGAGAAGGGG GTGCTCAGGT GGAGGTGTGG GGTATGCACC | |
| | TGAGCTCCTG CTTCGCGCCT GCTGCTCTGC CCCAACGCGA CCGCTGCCCG GCTGCCCAGA | |
| | GGGCTGGATG CCTGCCGGTC CCCGAGCAAG CCTGGGAACT CAGGAAAATT CACAGGACTT | |
| | GGGAGATTCT AAATCTTAAG TGCAATTATT TTTAATAAAA GGGGCATTTG GAATCAgctt | poly A |
| 24701 | ctgcgggtct ctctgggatt cagggcaggg aggatgtatc caggggccct ggaacagagg | |

TABLE I-continued

| | | |
|---|---|---|
| | tagctccttt gtcctcagca ggccccccaga cattcccaca gtgggtgtgc gccgtcctct | |
| | gtctcaagcc ggcatccatc acgtcatgtt cccatgtcac gaggcctgac atcacctcat | |
| | gtcctgtccc catctcacct cacatcccgt cacctcatgt ccccgcatca cctaaagccc | |
| | catgtcacct ttgtgtccca tacccccatc tcacatgcct acctcatgtc cccatgtcac | |
| 25001 | cttcacgtcc catctcacct cacctacctc cccacctacc tccccctcccc tcctcccctc | |
| | ccctcctcac ctgacctccc ctccccacgt cacctccctt cccctcccca cctcacctcc | |
| | cctccccacc tcccctcccc tccactcctc acctaccctc cccatgtcac ctccccttcc | |
| | ctccccacct cccctcccac cccacctccc ttcccctccc ctcctcacct gacctcccct | |
| | tcccatgtca cctctcctcc cctcccaacc tcccgtcccc atcccacttc acctcccctc | |
| 25301 | ctcacctgac ctcccctccc tatgtcatct ctcctcccct cccaccgcac ctcccctccc | |
| | ctcctcccct cacctgacct ccctacccca cctcaccccc tctcccctcc tcacctcctc | |
| | tcctcctctc cccattcatc ctcacactcc tgcttccccc atctctaagg tgactgggga | |
| | atgtccagtg ggtgttaggc atgtggtggg agtgtggccc ccagggctgt gtagacaaca | |
| | ggaccctgca aggaaggggc tttccaacag tggggcctaa gactttaggc agaggccaga | |
| 25601 | aatctgtccc caagtgatgc agttagagag gatttcaggc ccaggttctc cctggcaagc | |
| | ccagagaaag ggaaagaagc ccattttatt gaaataacag caggagaaat cactgcccctt | |
| | agccagtcag acgcttcagt ttatcactta gaattaatgc *agtggctcac acctgtaatc* | |
| | *ccagcacttt gggaagtcca ggcgggcagc tcacttgagg tcaagagttt gagagcagcc* | *half Alu* |
| | *tggccaacat ggtgaaaccc catctctact aaaaatacaa aattaaggcc aggcgcagtg* | *(125 bp)* |
| 25901 | *gctcacgcct gtaatcccag cactttggga ggctgaggca ggcggatcac gaggtcaaga* | |
| | *gatggagacc atcctggcta acatggtgaa accccgtctc tactgaaaat acaaaaatta* | *Alu repeat* |
| | *gctgggtgtg gtggcacaca cctgtagtcc cagctacttg gtctcgcaag gctgaggcag* | *(291 bp)* |
| | *gagaatcgct tgaacccggg aggcggaggt tgcagtgagc cgagatcgcg ccactgcact* | |
| | *ccagactgat gacagagcga gactgtctca aaaaaaaaaa aaattaggca tggtggtgtg* | |
| 26201 | *tgcctgcagt cccagctact cagaaggctg aggcacaaga atcacttgaa cccgggaggc* | *half Alu* |
| | *agaggttgta gtgagccaag atcgtgccac tgcactccag cctgggcgac agagtgagac* | *(150 bp)* |
| | *tccatctcaa aaaaaaaaaa aaaaaaggcc aggcgcggtg gctcatgcct gcaattccag* | |
| | *cactttggta ggccaaggca ggcggatcac gaggccagga gtccgagacc agcctgacca* | |
| | *acgtggcaaa accccatctc tactaaaaat acaaaaatta gctgggtgtg gtggcacgcg* | *Alu repeat* |
| 26501 | *cctgtaatct tagctactca ggaggctgag gaaggagaat tgcttgaatc tgggaggcgg* | *(288 bp)* |
| | *aggctgcagt gagctgagat cacgccactg cagtccagcc tgggcgacag agtgagactc* | |
| | *catctcaaaa aaaaaacaaa* agaagtggcc aaccccgaag tcctctgcag agcgatggat | |
| | tacttttgcc accttcctga aaaccaggag cagaaagtac agtgacttcc ccgtggagca | |
| | gcatgacatc cctgggggggc agtgtgtcta cctgggtgac cagcactatt gtcttctggg | |
| 26801 | tcagcttttg tagaagcgga cactgctctt ctgccatgtc acaggccagg gcctgacccc | |
| | cgtgtgccac ttttaccatc cagattgaca tcactaagtc atctcgcgcc ctaaagttcc | |
| | tctgtaaggt ggacgtagta gtgacaataa catatgttac ttcctcccct catcctagtc | |
| | ccatgtgggg ttaagaagca ggaacgtttg tcttgaggcc agcagcgtgc ctggtctcgg | |
| | tgctgagggc gacctgccct aacgctctgc caggctcgcc aggtctgcag ttgacaccca | |

TABLE I-continued

| | | |
|---|---|---|
| 27101 | agacggtcag ggagggttga tggagcgtgg tagcctcggc cagcctggac cgaccatcag | |
| | cgtcctcacc ttctgtgcca ccgcccagcc tggcagggcc actgtagcct tagccccttg | |
| | taggatctga cccttccttg gctgctgtaa cgaaataccc aagactgggt aatttataaa | |
| | caacagaaat ggatttctca cagggctgga ggctgggaag tccaagatcg aggcaggttc | |
| | tgtgtctggt gaaggctgct gtctgtatca taaatggcgc actctccatc atcgtggtag | |
| 27401 | aaggcgaaga caagctccct tgagcgctaa atgccactga tgaggatgga gggccctcag | |
| | gactcatcac ctcccaacag ccccaccact tttttttttt *ttttttttg agaccgagtt* | |
| | *tcactcttgt cacccaggct gtagtgcaat ggtgcaatct tggcttattg caacctttgc* | |
| | *ctcccaggtt caagtgattc tcctgcctca gcctcccgag gagctaggat tacaggcatc* | |
| | *cgccaccatg cctggctaat tggatcttta gttgtatttg tattttagtt tatttgtatt* | *Alu repeat* |
| *27701* | *ttaattgaga tgggatttca ccatgctggc caggctggtc ttgaactcct gacctcaggt* | *(320 bp)* |
| | *tatctgcctg cctcagcctc tcaaagtgct gggattacaa gcatgaggca ctatgtccgg* | |
| | *cc*agccccac ctcttaaaac catgtcattg gggattaggt ttcaacagga atttggggtg | |
| | ggggcaaacc ttcagaccat aggacagggc tatcaggagt cctgagtgag gaggttggca | |
| | tggggtggga cagtgctccc tgtgtgggaa gggacagggt cggagggggg agaggagttg | |
| 28001 | tttccatcct ctgagaggcc aggggtctcc tcagggtggt ccaaacggta cagcccatta | |
| | catgggacgc tggcctgtgg gcacctcaag gcagcttcat ctgtttctca ccagtgcctg | |
| | atacaggccc tgcctcagtg ggaccctatt gaacttaggt gaattttaaa gcaata*ggcc* | |
| | *aggtgtggtg gctcacgcct gtaatcccag tactttggga ggcctaggtg ggcggatcac* | |
| | *ctgaggttgg gagtttgaga ccagcctgac caacatggag aaaccctgtc tctactaaaa* | |
| 28301 | *atacaaaatt agccaggtgt ggtggtgcat gcctgtaatc ccagctactc aggaggctga* | *Alu repeat* |
| | *gacaggagaa tcatttgaac ccgggaggcg gaggttgtgg tgagccgaga tcacgccact* | *(290 bp)* |
| | *gcactccagc ctaggcaaca agagcgaaag tccatctcaa ataaaaataa* agcaatgtgg | |
| | atgtggaccc caggcagctt gcagcggaga cgtcttagtg ccggggagcg ttcaagctgg | |
| | caccctccgc cctgggagaa gacatcctgg ggtctcgtgg tcagccgtct catatgtctc | |
| 28601 | ccagctcagt ctctaaaaca aggcctgctg ttggtgacaa aacgctcttg gctcatgttc | |
| | tgggcaatga gctactgcgt gtggtgggcc agcttcacag gtgtgaccca tcgcaggccc | |
| | acaggccccg agctcagcag gctgcagctg ggtttaatgc tccacggtca ccatgttgaa | |
| | attgtgaata acttttgaac aaggggcccc acagctttca ttttgtgacg ggccctcggc | |
| | aaattctgcg gctggtcctg caaggggtgg tgcgttctct cccgtttacg ttggtataga | |
| 28901 | tgaatataaa cgcttccttt ctttccttgc ctggtgggga atggatcaga aagccagggc | |
| | tgatgataga aaccagcaga gaatctccaa gtgtaagaca ttagtcaaag gcccggcgtg | |
| | gagcccacag gtccttagcg ttcggaagac gattgccttc ccagccccact ccaaggaaga | |
| | atcagtgctg tctggcagca gcctccaggt gtgtctccac aaaggcccag ctttcctttt | |
| | tgcaaatcaa tgacatcaat aatccgttac atggcctgca gagaagccct ctggcggcca | |
| 29201 | ctgtggggcc ctgtgggcct tatgcctgct cttcctgatc tggtggaggc tcagagagga | |
| | gctaggacaa gggatggtgc ccctatacca ccccaccccc acatacgtgc ctgcagaagg | |
| | ccacatgacc aggattatgg tgggtgaggg ccagagggaa ggcccaggtg agagggtgga | |
| | atgtgaacag gctggttatt tgcgtgccag ggacaagaga gaaaaaagct cagcattagc | |
| | agagaagacg gacttctgcg gtggcaccta cagctgttcc cttggcctcc caaacaaccc | |

TABLE I-continued

| | | |
|---|---|---|
| 29501 | aggtgtgacg tcgggaaccg ggaatgcagg caacagagtg attccagctg cctcacaagg | |
| | aagagggtgt gtgggaagag cagagcatcc gggctggaag cagtcagaac catgcgtgca | |
| | gccggacact cattgttctt ccccacgtgt gctgggcacc cgctctgcgt caggctctgt | |
| | tccaggagtt gggtgaaacg gtgactgaaa tagacagaac tcctgtcggt gatgcccacg | |
| | tgagagaata taatcaatgg acaatgcacc gcacatattt aaaatgtgca aattgatccg | |
| 29801 | ttttgacatg tgaatgtctg tgaaccagct ctacagttaa gatggtgacc atctccatca | |
| | ccctcaaagt ctccagctac ccactgactg gaaaccactg gtatgttttt tgtcaagata | |
| | tatttctttg tattttatag aattttgtat aaaggggaat ttttttgtca cacactactc | |
| | aacataattt ctttgagatt tatccatcaa taactcatcc tttttagttg ctaaatagtt | |
| | ttccactgta tgcaaatgcc accatttctt tatctgtcct ttatggatat cagaattgtt | |
| 30101 | tttgattttt ttgtttgttt gtttaaagac agggtcttgc tgcgcgtggt *gctcacgcct* | |
| | *gtaatcccag cactttggga ggctgaggca ggcagatcac ctgaggtcag gagttcacgg* | |
| | *ctagcctggc caacatgggg aaaccccatc tctactaaaa atacaaaaat tagccgggcg* | |
| | *tggtggtggg cgcctgtaat cccagctact tgggaggctg aggcaggaga attgcttgaa* | *Alu repeat* |
| | *tccaggaggc ggagtttgct gtgagccgag atcgtgccat tgcactccag cgtgggcaac* | *(276 bp)* |
| 30401 | *agagcgagac tccatctcaa aaaacaaaac* aaaacaaaaa cagggtcttg ctctgtcacc | |
| | caagcaggaa tgcagtggca ccatcatagc tcaccatagc ctcaacctca tgggtttaat | |
| | tgatcctccc accttagcct cctgagcagc ctgggactac aggcatgcac caacacatgt | |
| | ggctaatttt taaaatattt tgtagagatg gtgtctcact gtgtttccca ggcttgtctg | |
| | gaactcctgg cctcaggtca tcctcctgcc ttggcctctg aaagtgctgg gattacaaac | |
| 30701 | gagggccatc accctcagcc cctctctgca atttttggct attatgaata aagctgctat | |
| | gagcagtcat ggacaagtct ttgacattat tttgtttctc ttgggcaaat agcaaggatg | |
| | atgtggtcag ttcatacggg aggtaaacta ttcattgttt aagaggctgc caaactgttt | |
| | ccaaatcgct gcaccattct gcattcctcc cgactgtgca ggggagttgg caggggctgc | |
| | gtatccgggc cagcattggc gtggtctgtt tccttttagc cattctagtg actgtgtatc | |
| 31001 | tcactgtggc tcttacactc ccctaatgac tattgatgtt gaacatcttt tcacccactt | |
| | atctgtcagc cataaatctt ctttggtaaa gtgtctgttc gcctcttttg cccattgtta | |
| | aactgggtcg ttccttatta tagagttata acatacgtca attttctagt gctgccgtaa | |
| | cacatgacca cagtttgagg gaattaaaat aacacaaatg tatttcatca cagttccata | |
| | ggtcagaaat ttgatacaag ggctctcctg gctgaaatcg gggtgtcagc agggctgcct | |
| 31301 | tcctttccag aagctccagg ggagaatccg tctccttgcc cacatgggct actggcagaa | |
| | ttgtttcatg cagttgtagc actgaggtct ctgtttccct tctgtcagtc agaggtcctt | |
| | ctcagcctac agaggcttcc cccatatctt ggctcatgcc tttttcaacc ccagaaatga | |
| | gggacttgag tccctctcat gcctgtcctt ccttccatca catcattctc tgaccaacca | |
| | tagccaaaga atagtcttga cttttaaggg ctcatgagat tagattgtgt ccacctagat | |
| 31601 | aatccaggat ctcgatcgcc atgggaattc gcatgcctcg agaaattcgg cccccggggc | |
| | cgcggccgc | |

The complement sequence of the bovine alphasS1 promoter region is shown below in Table II. In the sequence that follows nucleotides 1–21 are part of a vector polylinker containing restriction sites. Bases 22–6299 are the alpha S1-casein promoter fragment. Bases 6300–6320 are the first 21 bp of alphaS 1-casein exon 1. Bases 6320–6331 are a synthetic linker containing restriction sites

TABLE II

| | | | | | | |
|---|---|---|---|---|---|---|
| 0 | gcggccgcg | gccccggggg | ccGAATTCTT | CAAAGATCGT | GTTCTAATAA | TGGATAATTT |
| | TAAATGAGTA | CTTATTTTAT | TTCAGTTCAG | TTCAGTCACT | CACTCCTGTC | TGACTCTTTG |
| | CGACACCATG | AACCACAGCA | AGCCAGGCCT | CCCTGTCCAT | CACCAACTCC | CGGAGTCCAC |
| | CTAAACCCAT | GTTCATCGAG | TCGATGATGC | CATCCAACCA | TCTCATCCTC | TGTCGTCCCC |
| | TTCTTCTCCT | GCCCTCAGTC | TTTCCCAGCA | TCAGGGTCTT | TTCCAATGAG | TCAACTCTTC |
| 300 | GCATCAGGTA | GCCAAAGTAT | TGTAGTTTCA | GCTTCAACAT | CAGTCCTTCC | AATGAACACC |
| | CAGGACTGAT | CTGCTTTAGG | ATAGACTGGT | TGGATCTCCT | TGCAGTCCAA | GGGACTCTCA |
| | AGAGTCTTCT | CCAACACCAC | AGTTCAAAAG | CATCAATTCT | TCGTGCTCAG | CCTTCTTTAT |
| | AGTCCAACTC | TCACATCCAT | ACGTGACTAC | TGGAAAAACC | ATAGCCTTGA | CTAGACGGAC |
| | CTTTCTTGAC | AAAGTAATGT | CTCTGCTTTT | TAATATGCTG | TCTAGGTTGG | TCATAACTTT |
| 600 | CCTTACAAGG | AGTAAGCATC | TTAATTTTAT | GGCTGCAATC | ACCATCTGCA | GTGAATTTGG |
| | AGCCCAGAAA | AATTAAGTCA | GCCACTGTGT | CCACTGTTTC | CCCATCTATT | TCCCATGAAG |
| | TGATGGGACC | AGATGCCATG | ATCTTAGTTT | TCTGAATGTT | GAGCTTTAAG | CCAACTTTTT |
| | CACTCTCTTC | TTTCACTTTC | CTCAAGAGGC | TCTTTAGTTC | TTCTTCACTT | TCTGCCATAA |
| | GGGTGGTACC | ATCTGCATAT | CTGAGGTTAT | TGATATTTCT | GCCAGCAATC | TTGATTCCAG |
| 900 | CTTGTGCTTC | TTCCAGCCCA | GCGTTTCTCA | TGATGTACTC | TACATAGAAG | TTAAATAAGC |
| | AGGGTGACAA | TATACAGCCT | TGACGTACTC | CTTTTCCTAT | TTGGAACCAG | TCTGTTGTTC |
| | CATGTCCAGT | TCTAACTGTT | GCTTCCTGAC | CTGCATACAG | TTTTTTCAAG | AGGCAGGGCA |
| | GGTGGCCTGG | TATTCCCATC | TCTTTCAGAA | TTTTCCATAG | TTTATTGTGA | TCCACACAGT |
| | GAAAGGTTTT | GGCATAGTCA | ATAAAGCAGA | AATAGATGTT | TTTCTGGAAC | TCTTTTGCTT |
| 1200 | TTTCGATGAT | CCAGTGGGTA | TTGGCAATTT | GATCTCTGGT | TCCTCTGCCT | TTTCTAAAAC |
| | CAGCTGGAAC | ATCTGGAGGT | TCACGGTTCA | CGTATTGCTG | AAGCCTTTTT | TTTTTTTTTT |
| | TTTTTTAATT | TCAGGCACTC | TTCTAAGTGT | GTGACCTTTT | CCCTCTCAAC | CACATAGGAA |
| | GTGGATATTA | CTAAACAGAT | GGGAACATTG | AGACAAAATG | AGGTTGCAAA | ATTACACTGC |
| | TGGTCATTGA | AAGCCAGAAA | TTAAACTTAC | AATTTGACCT | TGAAGCATTG | TCTTGCAACC |
| 1500 | ACTACATTCT | ATCTCTTTAC | TTAAACAATG | CTCACTTAAG | ATTTCCAAAG | ACCAATTGAC |
| | AGAGTATCAA | GTTAAAAAGG | ACACTGTTTT | AAATCCAAAT | ATAAAATCTA | TCATAGGTTC |
| | CACATTTCCA | GTACTATCAT | ATATTCAGAA | TATAAAACTT | CCTGAAAAGA | GCTCTGTTTT |
| | AGTTCTGGAT | ACTAAAATTC | TATTTATACA | ATATCTAAGA | GTAATCATTA | ATGATCTTAT |
| | TGTGTATCTT | TTCTTAGATT | CCAAATGGCA | TATGGATTTC | TAGACAAAAA | CAGAAATATC |
| 1800 | TTTCACATTT | CTCAGTAACT | TTCCTTCTGG | AAGGTTGACT | GTTTGTTATA | TAATTAAGCA |
| | ACACTTTCCT | AGAAGACTAA | TCAGTCAAAT | GTTCCTGGGA | GAACTTTGAC | AAACCAGTTT |
| | GAAACTTCAA | ATTCTGAATT | TTTCACTGTC | TCAAACAAAG | TCAGTCCTCC | AAAGAGGTTT |
| | GAATCTGGAC | TAGAATATTT | AGCAACAATG | TACATAATCT | TGCAGGGGAT | AGTGTGTCTC |
| | TTAACTCATA | GTTTTTTTTT | TCAAAAATCT | ATGTTTATTA | CTAATAATGT | TTTTTGTATG |

TABLE II-continued

| | | | | | | |
|---|---|---|---|---|---|---|
| 2100 | TGTGCTAATT | TTTCTAATAA | GTTTAATTTT | TTTTTCATTA | TTGAAATTTG | AAAGTCAAGA |
| | AAGCTTAGTT | CTCCCTTACC | CAGTCTATTT | CTGGTTTCAT | TTCTTTAGGG | ATTTTGTTGG |
| | ATTTTCAAAA | CAGGTTGTGA | TATCACTAGA | GTATCTATGC | CCTTGAGCTC | TTAAATTAGT |
| | CCAATCTATA | TCTATTGTTT | TGTTATAATT | ATTAAGAGTA | GACCCTTTTA | CTATGATAAA |
| | TGATCAATGT | TAGATGACCA | ACTTTATGGT | CACCCCATGT | ATGACTGTTA | CATCAGAAAA |
| 2400 | TTAATATTTT | TATTTATTTA | CAAGGCAAAG | GCCCATTTGA | CTACAAATAG | TCTAAATATG |
| | TGTCTCAAAT | TTAAGCCTTG | TTTAGTAGTT | GGAAGTGAAG | AATTTTAAGT | GATAAAGCAA |
| | ATTGAAAATA | TCAATATAAA | TCAAATAAAT | GTAGGCTAAC | ATTTTGCATG | ATTTGGCATT |
| | ATATAAATCT | ACAATCCTTT | TCACGGATCA | CAAACTTGTT | GTGGTGAAGG | GCCTTGAGTA |
| | ACTCAATGAA | GCTATGAGTC | ATGTCATACA | AAGCTCCCCA | AAATGGTCAA | GTCATACTGA |
| 2400 | AGAGTTCTGA | CAAAATGTGG | TCCACTGGAG | GAGGGAATGG | CAAACCACTG | CAATATTCTT |
| | ACCATGAGAA | TCCCATGAAT | AGTATGAAAA | GGCAAAAAGA | TACGACACCA | GAAGATGAGC |
| | TCCCCAAGTC | AGAAGATGTC | CAATATGCTA | CTAGGGAAGA | GCAGAGGGCA | GTTACTAATA |
| | GCTCCAGAAA | GGATGGAGCA | GGTGGGCCAA | AGCAGAAATG | ACTGGTTGTG | TCTGGTGATA |
| | AAAGTAAAGT | CCAATGCTGT | AAAGAACAGT | ATTGATTAGG | AACTTAGAAT | GTTAGGTTCA |
| 3000 | TGAATTAAGG | CAAGTTGGAT | ATGGTCAAGC | AGGAAAGAAA | TCAGTGAACT | AAAATTGGAC |
| | AGGAATGGGC | AATTTAATTC | AGATTACCAT | TATATCTATT | ACTGTGGGCA | AGAATCCCTT |
| | AGAAGAAATA | GAGTAGTCCT | CATAGTCAAG | AAAAGAATCT | GAAATGCAGT | GCTTGGATGC |
| | AATCTCAAAA | ACAATAGAAT | GATCTCCATT | TGTTTCCAAG | GCAAACCATT | CAACATCACA |
| | GTAATCCAAG | TCTGTGCCCC | AACCACTAAC | GCTGATGATG | CTGAAGATGA | CCTGGTCTAC |
| 3300 | AAAGACCTAC | AAGACCTTCT | AGAACTGACA | CCGAATAAAT | AAATCAATAT | CCTTTTCATC |
| | ATAGGGGATT | GGAATGCAAA | AGTAGAAAGT | CAAGAAATAC | TTGGAGTAAC | AGGAAATTTT |
| | GCTTTGGAGT | TAAAAATGAA | GCAAGTCAAA | GGCTAACAGT | TGTGTCAAGA | GAACACATTG |
| | GTCATAGTGA | ATACCCTCTT | CCACCAACAC | GAGATGACTC | TGTACATGGA | CATCAGCAGA |
| | TGATCAACAC | TGAAATTGGA | TAGATTATAT | TCTTTGCAGC | CAAAGATGGA | GAGACTGTAT |
| 3600 | ATAGTCAGTA | AAAAATAAGA | CCTGGAGCTG | ACTGTGGCTA | AGATCTTGAG | CTCCTTATTG |
| | CAAAATTCAG | GCTTAAAAAG | AAAATGAAGA | AACCATTGAA | TGGACATTGA | AAATTGAATG |
| | GACATTCACT | ATGACCTAAT | CAAATCCCTT | ATGATTATAC | AGTAGAGGTG | ATGAATAGAT |
| | TCAAAGGATT | AGATCTGGCT | ATTACATTGT | ACAGGAGGCA | GTGACCAACA | CTATTCCAAA |
| | GTGGGGGTGG | GCGGAAATCC | AGAAGTTAAA | GTGGTTATCT | GAGAAGGCTT | TACAAATAGT |
| 3900 | TGAGAAAAGA | AGAAAGAAAA | TAGAAAAAGA | AAAGAAAAGA | AAGAGAAGCA | AAAGACAAAG |
| | ACAAAGGAGA | AAGGGGAAGC | TATACCCAAC | TGAATGCAGA | GTTCCAGAAA | ATAGCAAGAG |
| | AGAATGAGAA | GGCCTTCTTA | AATGAACAAT | GCAAAGAAGT | AGAGGAAAAC | AATAGAATGA |
| | GAAAGACTAG | AGATCTCTTC | AAGAAAACTA | CAGCTGTCGT | GGGAATATTT | CACAAGGGAA |
| | TATTTCCCAC | TTCCCAAGAC | CTTCCACCAG | GGATCTTCCC | AACCCAGATG | GGCATGAAAA |
| 4200 | AGGAGAGAAA | TAAAAAGGAC | TTAACAGAAG | CAGAAGAAAT | TAAGAAGAGG | TGGCAAGAAT |
| | AGTATTACAG | AAGAACTGTA | TTTAAAAGAT | CTTAATGACC | CAGATAGCCA | CAGTTGTGTA |
| | GTCTCTCATC | TACAGCTTAA | AACTCAATGT | TCAAAAAACT | AAGTTCATAG | CATACTGCCC |
| | CATCACTTCA | TGGAAAATAG | TGGGGGAGGG | GGAGAAGGTG | GAAGTAGTGT | CAGATTTTAT |
| | TTTCTTGGAC | TCAAAATCAC | TGCAGACAGT | GATTATAGCC | ATGAAATTAA | ATGACGCTTA |

TABLE II-continued

| | | | | | | | |
|---|---|---|---|---|---|---|---|
| 4500 | CTCCTTGAAA | AGAAAGTTCT | GAAAAACCTA | GACAACATAT | TAAAAAGCAG | TGACATCACT | |
| | TTACTGATAA | GTGTCTTTAT | ACTCAAAGCT | ATGGTTTTTC | CAGTAGCCAT | GTACAGATGT | |
| | GAGAATTGGA | CTATGAAGAA | GGATGAGTGT | CAAAGGACTG | ATGTTTTCAA | ATTGTGGTGG | |
| | ATACACTCCT | TTGCATGCGT | GCTAAGTCAT | TTCAGTCATG | TCCAACTCTT | TGCAACCCAG | |
| | TGGACTGTCG | TCTGCCAGGT | TCCTCTGTCC | ATGGGATTCT | CCAGGCAAGA | GCAACGGAGT | |
| 4800 | GGGTTGTCAT | TTCCTCCACC | AGGGGATCTT | CCCAATCCAG | ATATTGAACC | TGCATCTCTA | |
| | ATGTTTCCTG | CATTGGCAGG | CAGGTTCTTT | ACCACTAGTG | CCACCTGGAA | AGTCCGGATA | |
| | CACTCCTGGG | AAAGACAAAA | GTAGAGTATT | ACAATGCAGC | AAGGATTTTT | GTTCTCAGCT | |
| | CCTTGAATAA | ATTATAGTGA | ATAGAAAACA | TTAGTATCTT | GTTGAAATTG | ATGTGAAACA | |
| | GATAGTAAGG | AAGATAATAT | CTAAAGAAAA | CTTCAATATG | GGAAATTATA | GTCTTTTCTA | |
| 5100 | TCTTCAAAGT | GGACAGCCTG | AACAGTTTTG | AAATTTCTTT | TAATACAAAA | TAATGTTCCT | |
| | GTCATACAAC | TGTGAATACA | CTGAAAATAT | CACTATAGAT | TTTTTAAAGT | ATATAATATG | |
| | ATTCCTTTCT | TATAAACAAT | GAGTTGCAAT | CAACAAGTTT | TTAAAGCTCT | CACTTGTATA | |
| | GATTTATTTT | TAGCACATAA | TATTTTTCTA | CAATGTACAA | TGCCAGTTAA | TTCTAGGAGT | |
| | ACAATTAAGA | ATTGGAGAGA | TAGGAATTTT | TTTCTTTTAC | TTGTTTACTT | TAAAAGATGG | |
| 5400 | AAAATCAGAG | TTATGGTTTA | TTTTTCGCAA | TATTTAAAAA | TTATAATTCT | TGAATAACTA | |
| | TTAATTTTAA | TTAAATAATC | TGTAATGAGA | ATCCTCCTAC | CAATGTAGGA | GACGTGAGTT | |
| | TGACTCCCGG | GTAGGGAAGA | TACCCTGCAG | AAGGAAATGG | CAACCCACTC | CAATATTATT | |
| | ACTTGGGAAA | TCCCATGGAC | AGAGGAGACT | GGCAGGCTGC | AGTCCATGGG | GGTCACAAAG | |
| | AACTGGACAC | GACTTAGAAA | CTAAACAACA | ACAATTTATA | CCAGAATGAA | TGAACTAGTT | |
| 5700 | ACCACAACTA | GTACACCCAA | AATGAACAAA | AAATAGCTTG | GTGGTATAAT | TAAAATGCCA | |
| | CCAAAATTTA | TACAATAATT | ATATTTTCTT | TTTGCAGGAA | AAAGATTAGA | CCACATATAA | |
| | TGTAACTTAT | TTCACAAGGT | AAATAATTAT | AATAAATAAT | ATGGATTAAC | TGAGTTTTAA | |
| | AAGGTGAAAT | AAATAATGAA | TTCTTCTCAT | GGTCTTGTAT | GTTAATAAAA | ATTGAAAAAT | |
| | TTTGAAGACC | CCATTTTGTC | CCAAGAATTT | CATTTACAGG | TATTGAATTT | TTCAAAGGTT | |
| 6000 | ACAAAGGAAA | TTTTATTGAT | ATAATAAATG | CATGTTCTCA | TAATAACCAT | AAATCTAGGG | |
| | TTTTGTTGGG | GTTTTTTTGT | TTGTTAATTT | AGAACAATGC | CATTCCATTT | CCTGTATAAT | |
| | GAGTCACTTC | TTTGTTGTAA | ACTCTCCTTA | GAATTTCTTG | GGAGAGGAAC | TGAACAGAAC | |
| | ATTGATTTCC | TATGTGAGAG | AATTCTTAGA | ATTTAAATAA | ACCTGTTGGT | TAAACTGAAA | |
| | CCACAAAATT | AGCATTTTAC | TAATCAGTAG | GTTTAAATAG | CTTGGAAGCA | AAAGTCTGCC | |
| 6300 | ATCACCTTGA | TCATCAACCC | atcgataggc | ct | | | exon 1 |

Computer Systems for Storing Sequence Data

Figure 5A:
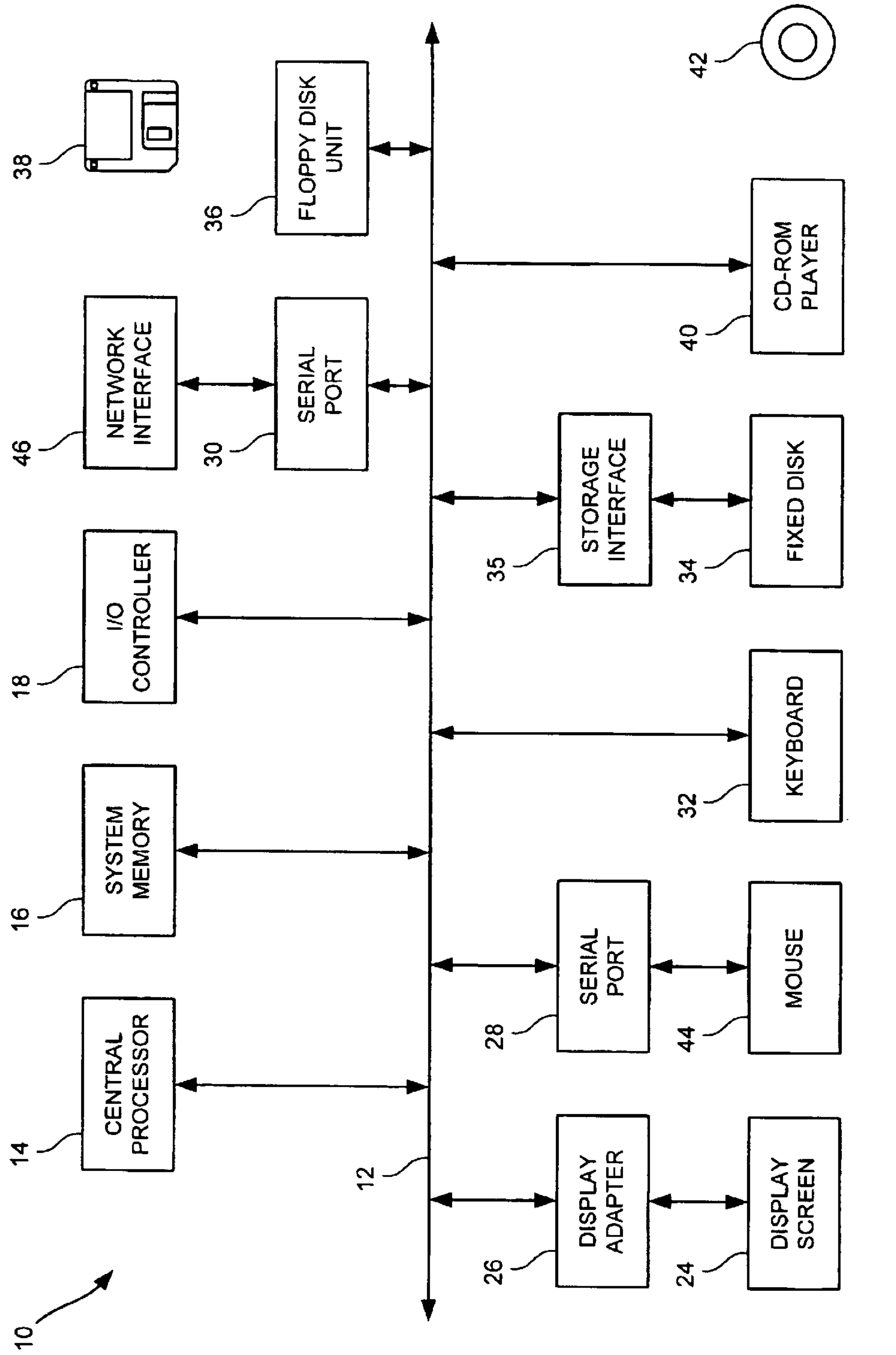
FIGS. 5A and 5B: Depict computer systems suitable for storing and transmitting information relating to the sequences of the invention.

FIG. 5A depicts a block diagram of a computer system 10 suitable for implementing the present invention. Computer system 10 includes a bus 12 which interconnects major subsystems such as a central processor 14, a system memory 16 (typically RAM), an input/output (I/O) controller 18, an external device such as a display screen 24 via a display adapter 26, serial ports 28 and 30, a keyboard 32, a fixed disk drive 34 via a storage interface 35 and a floppy disk drive 36 operative to receive a floppy disk 38, and a CD-ROM (or DVD-ROM) device 40 operative to receive a CD-ROM 42. Many other devices can be connected such as a user pointing device, e.g., a mouse 44 connected via serial port 28 and a network interface 46 connected via serial port 30.

Many other devices or subsystems (not shown) may be connected in a similar manner. Also, it is not necessary for all of the devices shown in FIG. X to be present to practice the present invention, as discussed below. The devices and subsystems may be interconnected in different ways from that shown in FIG. 5A. The operation of a computer system such as that shown in FIG. 5A is well known. Databases storing sequence information according to the present invention can be stored, e.g., in system memory 16 or on storage media such as fixed disk 34, floppy disk 38, or CD-ROM 42. An application program to access such databases can be operably disposed in system memory 16 or sorted on storage media such as fixed disk 34, floppy disk 38, or CD-ROM 42.

Figure 5B:
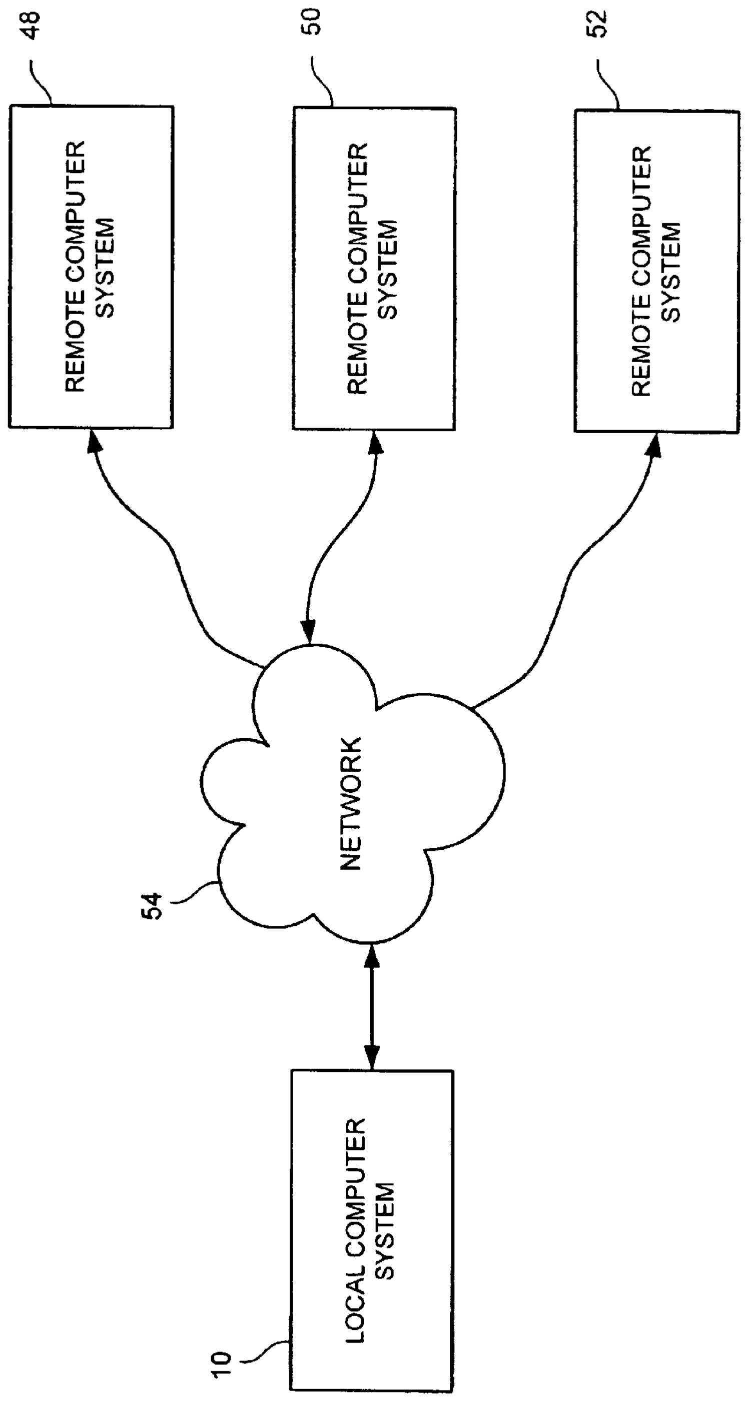

FIG. 5B depicts the interconnection of computer system 10 to remote computers 48, 50, and 52. FIG. 5B depicts a network 54 interconnecting remote servers 48, 50, and 52. Network interface 46 provides the connection from client computer system 10 to network 54. Network 54 can be, e.g., the Internet. Protocols for exchanging data via the Internet and other networks are well known. Information identifying thesequences described herein can be transmitted across network 54 embedded in signals capable of traversing the physical media employed by network 54.

The sequences shown in Tables I and II or subsequences of at least 15, 20, 100, 500, 1000, or 10,000 bases therefrom are stored in computer redable medium, optionally as a database. Sequences can be stored in the form of DNA or RNA. In the latter case, T's shown in the sequences shown in Tables I and II should be read as U's. Different subsequences can be recorded as different records. Sequences can be retrieved from storage for use in transgene design, design of hybridization probes, or comparative sequence analysis. For example, the computer can be used to assembled different combinations of sequences from different sources, revealing the presence of restriction sites in the combined fragment, the reading frame, transcription start site and other notable features useful for transgene design.

Sequence data can also be retrieved and analyzed for probe design. The computer can be programmed to compare different sequences for suitability as probes based on lack of self-annealing, and melting temperature and specificity. Probes can be used in isolating allelic or species variant sequences, or for determining the presence of a human alpha-glucosidase polynucleotide, for example, in a transformed cell or transgenic animal. Hybridization probes are typically 10–100 nucleotides long, and are often from 20–50 nuleotides long. Probe hybridizations are typically performed under stringent hybridization conditions. The phrase "stringent hybridization conditions" refers to conditions under which a probe will hybridize to its target subsequence, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50%/o of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents as formamide.

The disclosed sequences are also useful for comparative sequence analysis with other sequences. One example of algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Comparative sequence analysis is useful for identifying families of related genes. Such genes may be allelic or species variants or nonallelic. Comparative sequence analysis is also useful for identifying common regioins within otherwise unrelated genes. Such regions may be conserved, for example, due to a common regulatory role in different genes. Such regulatory sequences are useful in vector and transgene design.

EXAMPLES

Example 1

Construction of Transgenes (a) cDNA Construct

Construction of an expression vector containing cDNA encoding human acid α-glucosidase started with the plasmid p16,8hlf3 (see DeBoer et al. (1991) & (1993), supra) This plasmid includes bovine αS1-casein regulatory sequences. The lactoferrin cDNA insert of the parent plasmid was exchanged for the human acid α-glucosidase cDNA (Hoefsloot et al. EMBO J. 7,1697–1704 (1988)) at the ClaI site and SalI site of the expression cassette as shown in FIG. 1. To obtain the compatible restriction sites at the ends of the α-glucosidase cDNA fragment, plasmid pSHAG2 (id.) containing the complete cDNA encoding human α-glucosidase was digested with EcoRI and SphI and the 3.3 kb cDNA-fragment was subcloned in pKUN7ΔC a pKUN1 derivative (Konings et al., Gene 46, 269–276 (1986)), with a destroyed ClaI site within the vector nucleotide sequences and with a newly designed polylinker: HindIII ClaI EcoRI SphI XhoI EcoRI SfiI SfiI/SmaI NotI EcoRI*(*=destroyed site). From the resulting plasmid pαgluCESX, the 3.3-kb cDNA-fragment could be excised by ClaI and XhoI. This fragment was inserted into the expression cassette shown in FIG. 1 at the ClaI site (SEQ ID NO:5) and XhoI-compatible SalI site (SEQ ID NO:4). As a result, the expression plasmid p16, 8αglu consists of the cDNA sequence encoding human acid α-glucosidase flanked by bovine αS1-casein sequences as shown in FIG. 1. The 27.3-kb fragment containing the complete expression cassette can be excised by cleavage with NotI (see FIG. 1).

(b) Genomic Constructs

Figures 2A, 2B, 2C:
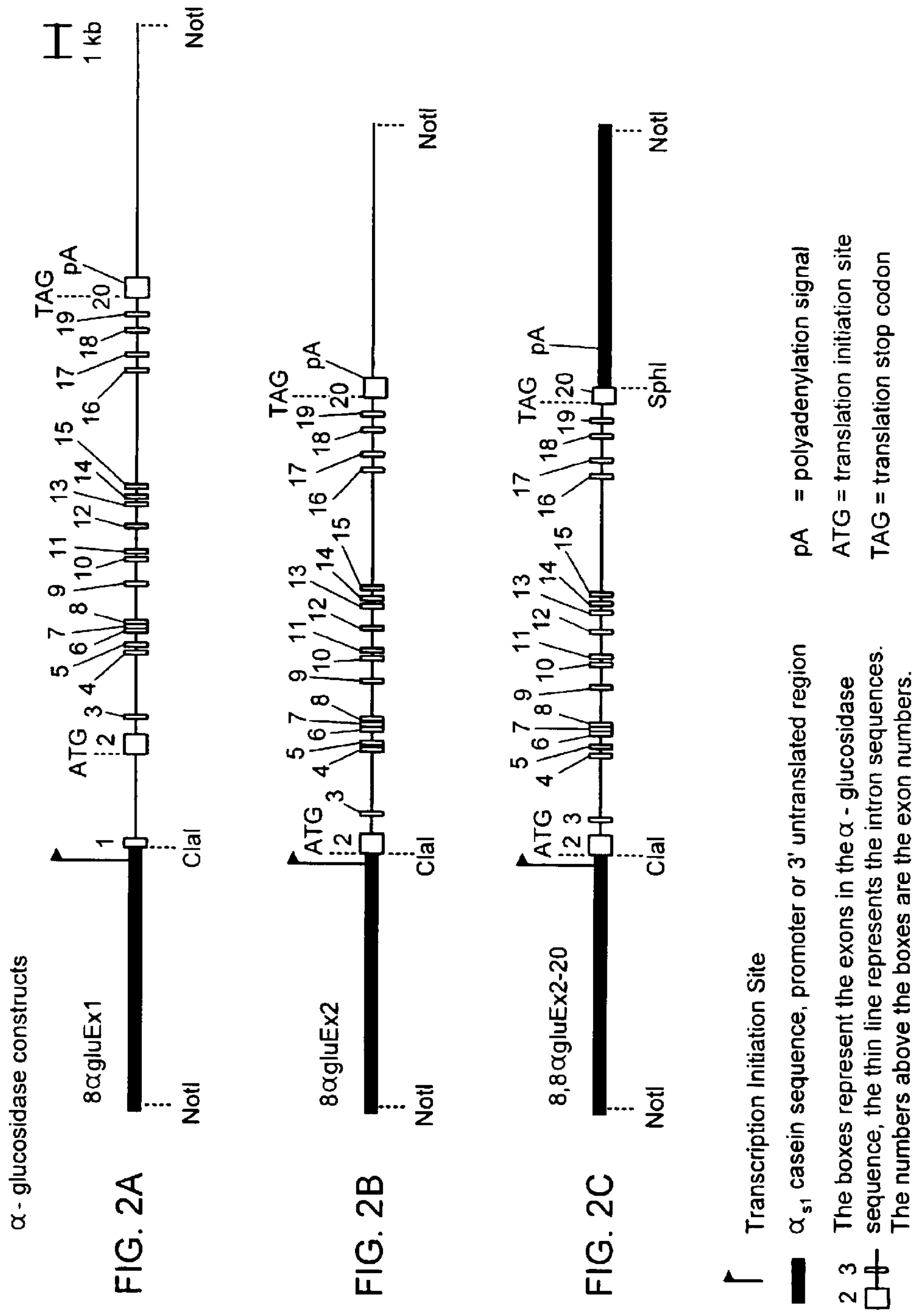
FIG. 2 (Panels A, B, C): Three transgenes containing acid α-glucosidase genomic DNA. Dark shaded areas are αs1 casein sequences, open boxes represent acids α-glucosidase exons, and the thin line between the open boxes represents α-glucosidase introns. Other symbols are the same as in FIG. 1.

Construct c8αgluex1 contains the human acid α-glucosidase gene (Hoefsloot et al., Biochem. J. 272, 493–497 (1990)); starting in exon 1 just downstream of its transcription initiation site (see FIG. 2, panel A). Therefore, the construct encodes almost a complete 5' UTR of the human acid α-glucosidase gene. This fragment was fused to the promoter sequences of the bovine αS1-casein gene. The αS1-casein initiation site is present 22 bp upstream of the αS1-casein/acid α-glucosidase junction. The construct has the human acid α-glucosidase polyadenylation signal and 3' flanking sequences. Construct c8αgluex2 contains the bovine αS1-casein promoter immediately fused to the translation initiation site in exon 2 of the human acid α-glucosidase gene (see FIG. 2, panel B). Thus, the αS1-casein transcription initiation site and the α-glucosidase translation initiation site are 22-bp apart in this construct. Therefore no α-glucosidase 5' UTR is preserved. This construct also contains the human acid α-glucosidase polyadenylation signal and 3' flanking sequences as shown in FIG. 2, panel B.

Construct c8,8αgluex2–20 differs from construct c8αgluex2 only in the 3' region. A SphI site in exon 20 was used to fuse the bovine αS1-casein 3' sequence to the human acid α-glucosidase construct. The polyadenylation signal is located in this 3' αS1-casein sequence (FIG. 2, panel C).

Methods for Construction of Genomic Constructs

Three contiguous BglII fragments containing the human acid α-glucosidase gene were isolated by Hoefsloot et al., supra. These fragments were ligated in the BglII-site of pKUN8ΔC, a pKUN7ΔC derivative with a customized polylinker: HindIII ClaI StuI SstI BglII PvnI NcoI EcoRI SphI XhoI EcoRI*SmaI/SfiI NotI EcoRI*(*=destroyed site). This ligation resulted in two orientations of the fragments generating plasmids p7.3αgluBES, p7.3αgluBSE, p8.5αgluBSE, p8.5αgluBES, p10αgluBSE and p10αgluBES.

Because unique NotI-sites at the ends of the expression cassette are used subsequently for the isolation of the fragments used for microinjection, the intragenic NotI site in intron 17 of human acid α-glucosidase had to be destroyed. Therefore, p10αugluBES was digested with ClaI and XhoI; the fragment containing the 3' α-glucosidase end was isolated. This fragment was inserted in the ClaI and XhoI sites of pKUN10ΔC, resulting in p10αgluΔNV. Previously pKUN10ΔC (i.e., a derivative of pKUN8ΔC) was obtained by digesting pKUN8ΔC with NotI, filling in the sticky ends with Klenow and subsequently, annealing the plasmid by blunt-ended ligation. Finally, p10αgluΔNV was digested with NotI. These sticky ends were also filled with Klenow and the fragment was ligated, resulting in plasmid p10αgluΔNotI.

Construction of c8αgluex1

Since the SstI site in first exon of the α-glucosidase gene was chosen for the fusion to the bovine αS1-casein sequence, p8.5αgluBSE was digested with BglII followed by a partial digestion with SstI. The fragment containing exon 1–3 was isolated and ligated into the BglII and SstI sites of pKUN8ΔC. The resulting plasmid was named: p5αgluex1 (see FIG. 3, panel A).

The next step (FIG. 3, panel B) was the ligation of the 3' part to p5'αgluex1. First, p10αglu_N was digested with BglII and BamHI. This fragment containing exon 16–20 was isolated. Second, p5'αgluex1 was digested with BglII and to prevent self-ligation, and treated with phosphorylase (BAP) to dephosphorylate the sticky BglII ends. Since BamHI sticky ends are compatible with the BglII sticky ends, these ends ligate to each other. The resulting plasmid, i.e., p5'3'αgluex1, was selected. This plasmid has a unique BglII site available for the final construction step (see FIG. 3, panels B and C).

Figure 3A:
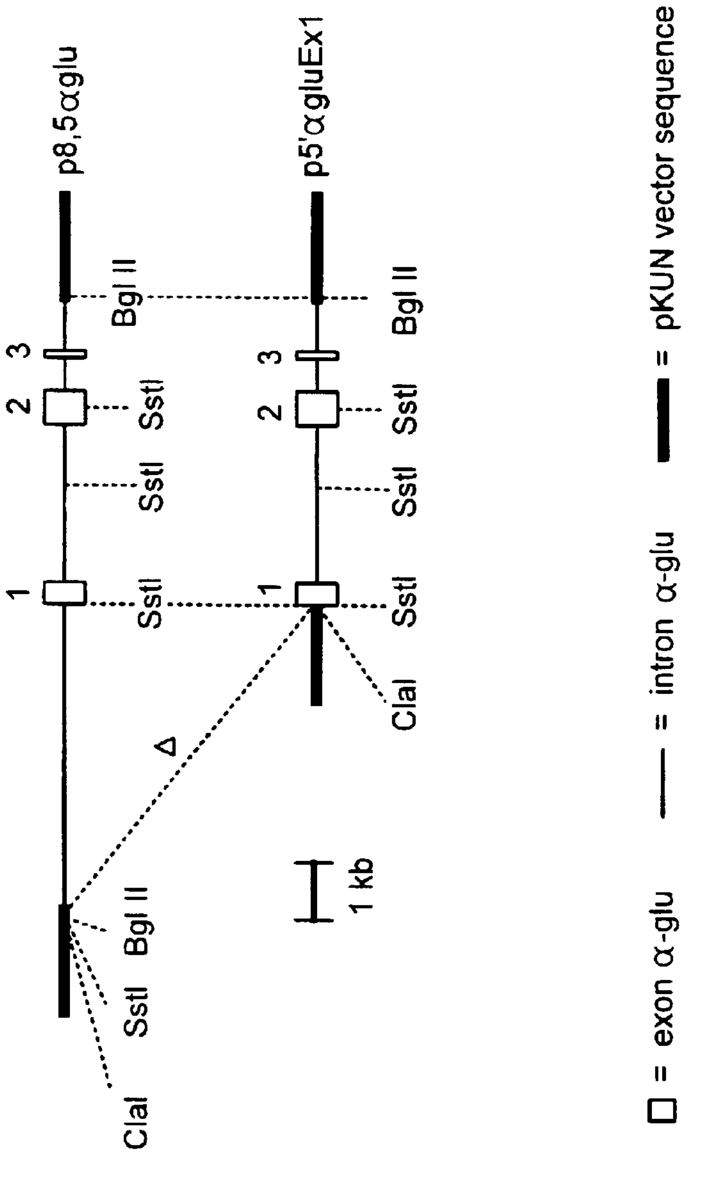
FIG. 3 (Panels A, B, C): Construction of genomic transgenes. The α-glucosidase exons are represented by open boxes; the α-glucosidase introns and nontranslated sequences are indicated by thin lines. The pKUN vector sequences are represented by thick line s.
Figure 3B:
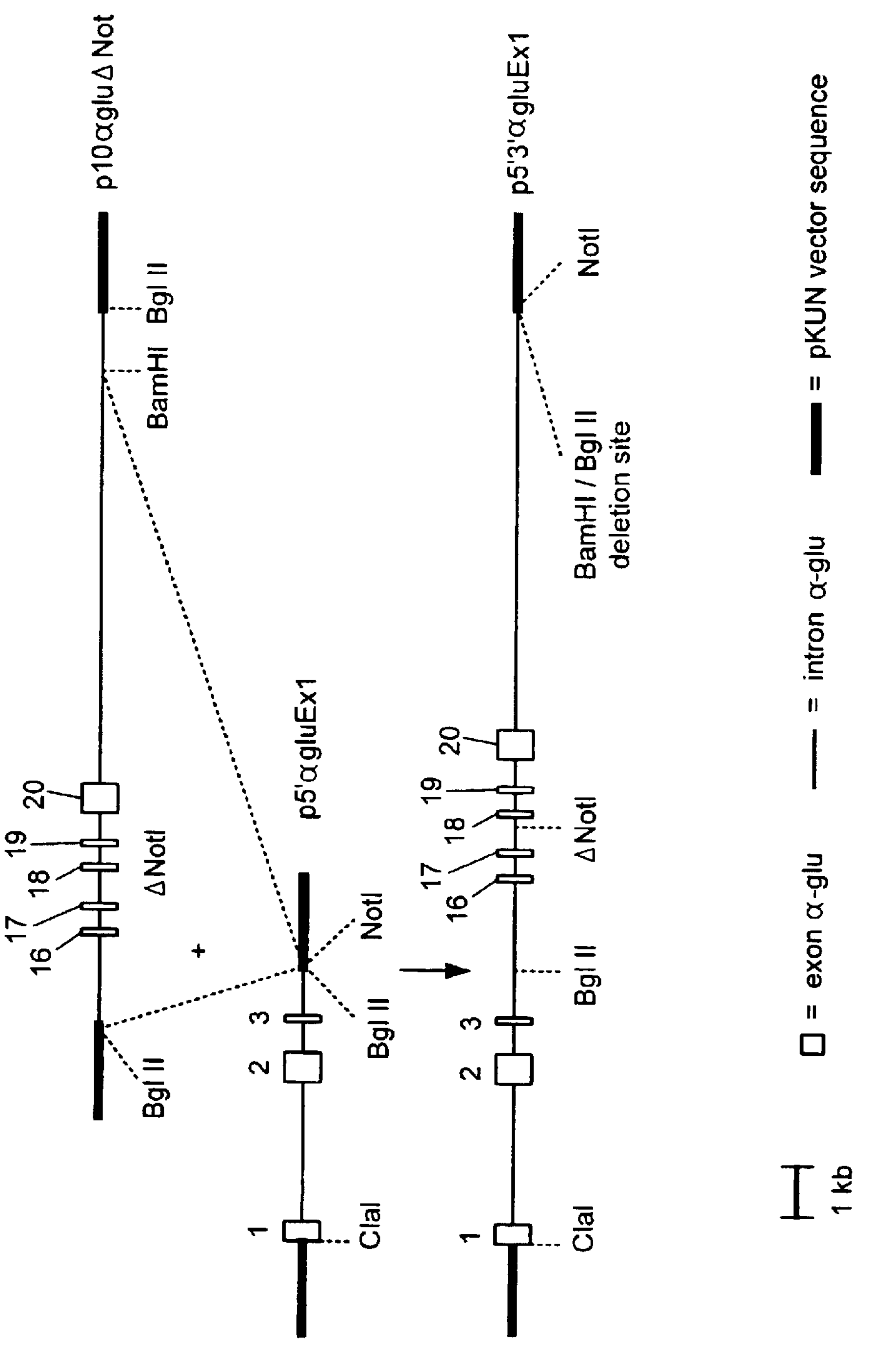
Figure 3C:
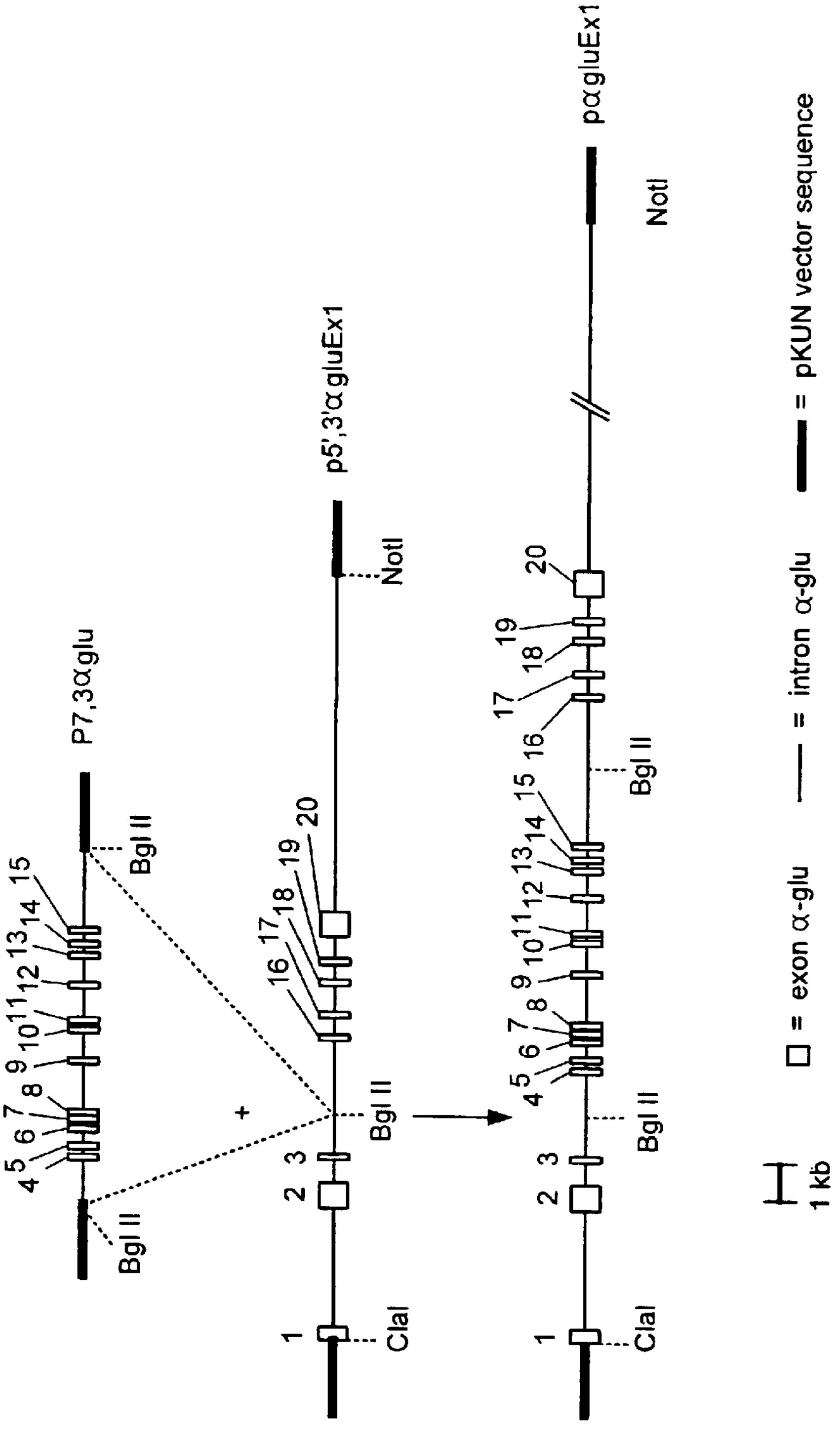

The middle part of the α-glucosidase gene was inserted into the latter construct. For this step, p7.3αgluBSE was digested with BglII, the 8.5-kb fragment was isolated and ligated to the BglII digested and dephosphorylated p5'3'αgluex1 plasmid. The resulting plasmid is pαgluex1 (FIG. 3, panel C).

The bovine αS1-casein promoter sequences were incorporated in the next step via a ligation involving three fragments. The pWE15 cosmid vector was digested with NotI and dephosphorylated. The bovine αS1-casein promoter was isolated as an 8 Rb NotI-ClaI fragment (see de Boer et al., 1991, supra). The human acid α-glucosidase fragment was isolated from pαgluex1 using the same enzymes. These three fragments were ligated and packaged using the Stratagene GigapackII kit in 1046 *E.coli* host cells. The resulting cosmid c8αgluex1 was propagated in *E.coli* strain DHSα. The vector was linearized with NotI before microinjection.

Construction of c8αgluex2 and c8,8αgluex2–20

The construction of the other two expression plasmids (FIG. 2, panels B and C) followed a similar strategy to that of c8αgluex1. The plasmid p5'αgluStuI was derived from p8,5αgluBSE by digestion of the plasmid with StuI, followed by self-ligation of the isolated fragment containing exon 2–3 plus the vector sequences. Plasmid p5'αgluStuI was digested with PglII followed by a partial digestion of the linear fragment with NcoI resulting in several fragments. The 2.4 kb fragment, containing exon 2 and 3, was isolated and ligated into the NcoI and BglII sites of vector pKUN12αC, resulting in p5'αgluex2. Note that pKUN12ΔC is a derivative of pKUN8ΔC containing the polylinker: ClaI NcoI BglII HindIII EcoRI SphI XhoI SmaI/SfiI NotI.

The plasmid p10αgluΔNotI was digested with BglII and HindIII. The fragment containing exons 16–20 was isolated and ligated in p5'αgluex2 digested with BglIII and HindIII. The resulting plasmid was p5'3'αgluex2. The middle fragment in p5'3'αgluex2 was inserted as for pαgluex1. For this, p7.3αglu was digested with BglII. The fragment was isolated and ligated to the BglII-digested and dephosphorylated p5'3'αgluex2. The resulting plasmid, pαgluex2, was used in construction of c8αgluex-20 and c8,8αgluex2–20 (FIG. 2, panels B and C).

For the construction of third expression plasmid c8,8α gluex2–20 (FIG. 2, panel C) the 3' flanking region of α-glucosidase was deleted. To achieve this, pαgluex2 was digested with SphI. The fragment containing exon 2–20 was isolated and self-ligated resulting in pαgluex2–20. Subsequently, the fragment containing the 3' flanking region of bovine αs1-casein gene was isolated from p16,8αglu by digestion with SphI and NotI. This fragment was inserted into pαgluex2–20 using the SphI site and the NotI site in the polylinker sequence resulting in pαgluex2–20-3αS1.

The final step in generating c8,8αgluex2–20 was the ligation of three fragments as in the final step in the construction leading to c8αgluex1. Since the ClaI site in pαgluex2–20-3'αS1 and pαgluex2 appeared to be uncleavable due to methylation, the plasmids had to be propagated in the *E. coli* DAM(−) strain ECO343. The pαgluex2–20-3'αS1 isolated from that strain was digested with ClaI and NotI. The fragment containing exons 2–20 plus the 3' αS1-casein flanking region was purified from the vector sequences. This fragment, an 8 kb NotI-ClaI fragment containing the bovine αs1 promoter (see DeBoer (1991) & (1993), supra) and NotI-digested, dephosphorylated pWE15 were ligated and packaged. The resulting cosmid is c8,8αgluex2–20.

Cosmid c8αgluex2 (FIG. 2, panel B) was constructed via a couple of different steps. First, cosmid c8,8αgluex2–20 was digested with SalI and NotI. The 10.5-kb fragment containing the αS1-promoter and the exons 2–6 part of the acid α-glucosidase gene was isolated. Second, plasmid pαgluex2 was digested with SalI and NotI to obtain the fragment containing the 3' part of the acid α-glucosidase gene. Finally, the cosmid vector pWE15 was digested with NotI and dephosphorylated. These three fragments were ligated and packaged. The resulting cosmid is c8αgluex2.

Example 2

Transgenesis

The cDNA and genomic constructs were linearized with NotI and injected in the pronucleus of fertilized mouse oocytes which were then implanted in the uterus of pseudopregnant mouse foster mothers. The offspring were analyzed for the insertion of the human α-glucosidase cDNA or genomic DNA gene construct by Southern blotting of DNA isolated from clipped tails. Transgenic mice were selected and bred.

Example 3

Analysis of Acid α-Glucosidase in the Milk of Transgenic Mice

Figure 4A:
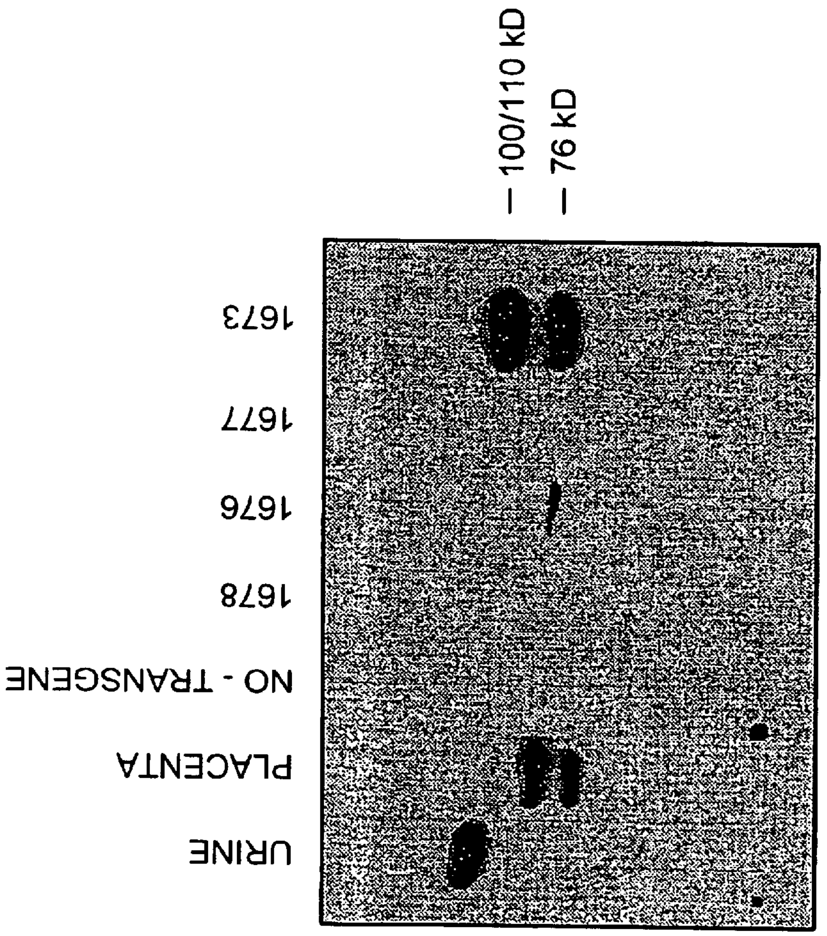
FIG. 4: (Panel A, B) Detection of acid α-glucosidase in milk of transgenic mice by Western blotting.
Figure 4B:
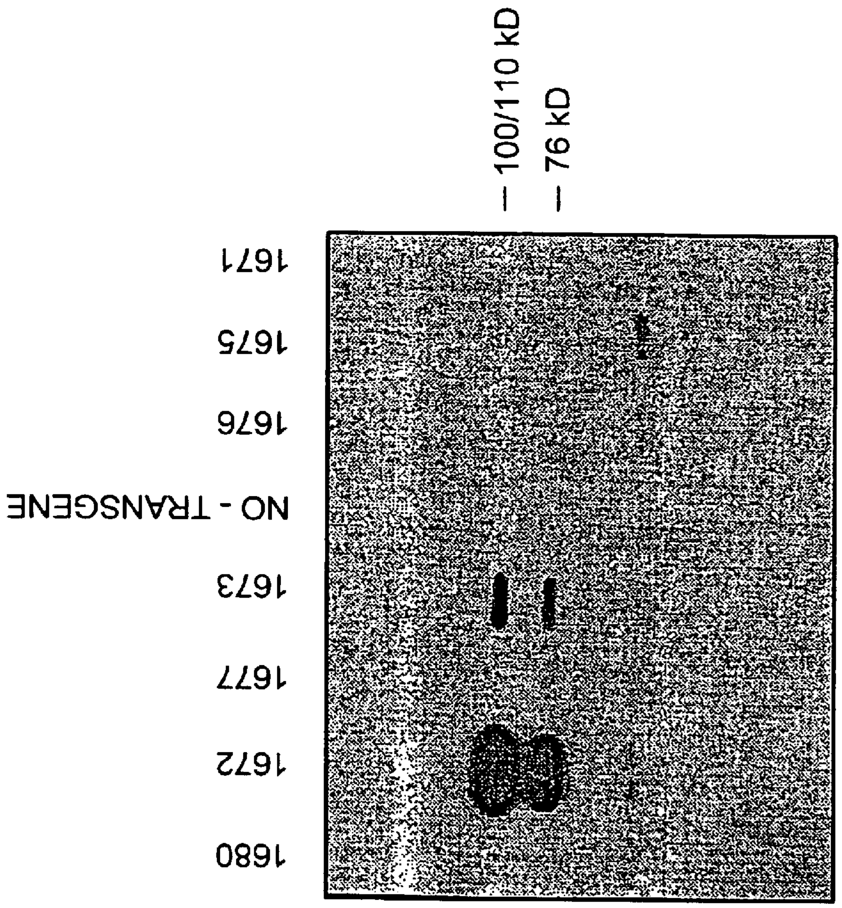

Milk from transgenic mice and nontransgenic controls was analyzed by Western Blotting. The probe was mouse antibody specific for human acid α-glucosidase (i.e, does not bind to the mouse enzyme). Transgenes 1672 and 1673 showed expression of human acid α-glucosidase in milk (FIG. 4). Major and minor bands at 100–110 kD and 76 kD were observed as expected for α-glucosidase. In milk from non-transgenic mice, no bands were observed.

The activity of human acid α-glucosidase was measured with the artificial substrate 4-methylumbelliferyl-α-D-glucopyranoside in the milk of transgenic mouse lines (See Galiaard, Genetic Metabolic Disease, Early Diagnosis and Prenatal Analysis, Elsevier/North Holland, Amsterdam, pp. 809–827 (1980)). Mice containing the cDNA construct (FIG. 1) varied from 0.2 to 2 μmol/ml per hr. The mouse lines containing the genomic construct (FIG. 2, panel A) expressed at levels from 10 to 610 μmol/ml per hr. These figures are equivalent to a production of 1.3 to 11.3 mg/l (cDNA construct) and 0.05 to 3.3 g/l (genomic construct) based on an estimated specific activity of the recombinant enzyme of 180 μmol/mg (Van der Ploeg et al., J. Neurol. 235:392–396 (1988)).

The recombinant acid α-glucosidase was isolated from the milk of transgenic mice, by sequential chromatography of milk on ConA-Sepharose™ and Sephadex™ G200. 7 ml milk was diluted to 10 ml with 3 ml Con A buffer consisting of 10 mM sodium phosphate, pH 6.6 and 100 mM NaCl. A 1:1 suspension of Con A sepharose in Con A buffer was then added and the milk was left overnight at 4□C with gentle shaking. The Con A sepharose beads were then collected by centrifugation and washed 5 times with Con A buffer, 3 times with Con A buffer containing 1 M NaCl instead of 100 mM, once with Con A buffer containing 0.5 M NaCl instead of 100 mM and then eluted batchwise with Con A buffer containing 0.5 M NaCl and 0.1 M methyl-α-D-mannopyranoside. The acid α-glucosidase activity in the eluted samples was measured using the artificial 4-methyl-umbelliferyl-α-D-glycopyranoside substrate (see above). Fractions containing acid α-glucosidase activity were pooled, concentrated and dialyzed against Sephadex buffer consisting of 20 mM Na acetate, pH 4.5 and 25 mM NaCl, and applied to a Sephadex™ 200 column. This column was run with the same buffer, and fractions were assayed for acid α-glucosidase activity and protein content. Fractions rich in acid α-glucosidase activity and practically free of other proteins were pooled and concentrated. The method as described is essentially the same as the one published by Reuser et al., Exp. Cell Res. 155:178–179 (1984). Several modifications of the method are possible regarding the exact composition and pH of the buffer systems and the choice of purification steps in number and in column material.

Acid α-glucosidase purified from the milk was then tested for phosphorylation by administrating the enzyme to cultured fibroblasts from patients with GSD II (deficient in endogenous acid α-glucosidase). In this test mannose 6-phosphate containing proteins are bound by mannose 6-phosphate receptors on the cell surface of fibroblasts and are subsequently internalized. The binding is inhibited by free mannose 6-phosphate (Reuser et al., Exp. Cell Res. 155:178–189 (1984)). In a typical test for the e phosphorylation of acid α-glucosidase isolated from milk of transgenic mice, the acid α-glucosidase was added to 104–106 fibroblasts in 500 μl culture medium (Ham F10, supplied with 10% fetal calf serum and 3 mM Pipes) in an amount sufficient to metabolize 1 μmole 4-methyl-umbelliferyl-α-D-glucopyranoside per hour for a time If period of 20 hours. The experiment was performed with or without 5 mM mannose 6-phosphate as a competitor, essentially as described by Reuser et al., supra (1984). Under these conditions acid α-glucosidase of the patient fibroblasts was restored to the level measured in fibroblasts from healthy individuals. The restoration of the endogenous acid α-glucosidase activity by acid α-glucosidase isolated from mouse milk was as efficient as restoration by acid α-glucosidase purified from bovine testis, human urine and medium of transfected CHO cells. Restoration by α-glucosidase form milk was inhibited by 5 mM mannose 6-phosphate as observed for α-glucosidase from other sources. (Reuser et al., supra; Van der Ploeg et al., (1988), supra; Van der Ploeg et al., Ped. Res. 24:90–94 (1988).

As a further demonstration of the authenticity of α-glucosidase produced in the milk, the N-terminal amino acid sequence of the recombinant α-glucosidase produced in the milk of mice was shown to be the same as that of α-glucosidase precursor from human urine as published by Hoefsloot et al., EMBO J. 7:1697–1704 (1988) which starts with AHPGRP (SEQ ID NO:3).

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A recombinant polynucleotide comprising an alpha S1-casein promoter (nucleotides 22–6299 of SEQ ID NO: 2) operably linked to a heterologous coding sequence.

2. A recombinant polynucleotide comprising an alpha glucosidase promoter (nucleotides 1–776 of SEQ ID NO:1) operably linked to a heterologous coding sequence.

3. The recombinant polynucleotide of claim 2, wherein the heterologous coding sequence encodes a lysosomal enzyme.

4. The recombinant polynucleotide of claim 1, wherein the heterologous coding sequence encodes a lysosomal enzyme.

5. The recombinant polynucleotide of claim 4, wherein the lysosomal enzyme is alpha glucosidase.

* * * * *